(12) United States Patent
Aebersold et al.

(10) Patent No.: US 7,183,118 B2
(45) Date of Patent: Feb. 27, 2007

(54) METHODS FOR QUANTITATIVE PROTEOME ANALYSIS OF GLYCOPROTEINS

(75) Inventors: Rudolf H. Aebersold, Mercer Island, WA (US); Hui Zhang, Seattle, WA (US)

(73) Assignee: The Institute for Systems Biology, Seattle, WA (US)

( * ) Notice: Subject to any disclaimer, the term of this patent is extended or adjusted under 35 U.S.C. 154(b) by 336 days.

(21) Appl. No.: 10/454,375

(22) Filed: Jun. 3, 2003

(65) Prior Publication Data

US 2004/0023306 A1    Feb. 5, 2004

Related U.S. Application Data

(60) Provisional application No. 60/385,707, filed on Jun. 3, 2002, provisional application No. 60/469,361, filed on May 9, 2003.

(51) Int. Cl.
*G01N 24/00* (2006.01)
(52) U.S. Cl. .................. 436/173; 436/518; 436/175
(58) Field of Classification Search .................. 435/6, 435/7.1, 7.92–7.94, 962, 973; 436/501, 518, 436/524, 63, 173, 174, 175, 825
See application file for complete search history.

(56) References Cited

U.S. PATENT DOCUMENTS

| 5,753,454 | A | * | 5/1998 | Lee .......................... 435/18 |
| 6,325,989 | B1 | * | 12/2001 | Duke-Cohan et al. ..... 424/9.34 |
| 2002/0037532 | A1 | | 3/2002 | Regnier et al. |
| 2002/0055186 | A1 | * | 5/2002 | Barry et al. ................ 436/518 |
| 2003/0077616 | A1 | * | 4/2003 | Lomas ........................ 435/6 |
| 2003/0129769 | A1 | * | 7/2003 | Regnier ...................... 436/518 |
| 2004/0110186 | A1 | * | 6/2004 | Aebersold et al. ............. 435/6 |
| 2005/0250152 | A1 | * | 11/2005 | Haugland et al. .............. 435/6 |

FOREIGN PATENT DOCUMENTS

| WO | WO 00/11208 | 3/2000 |
| WO | WO 02/052259 | 7/2004 |

OTHER PUBLICATIONS

Adam et al., "Proteomic profiling of mechanistically distinct enzyme classes using a common chemotype," *Nat. Biotechnol,* 20(8):805-809 (2002).
Adkins et al., "Toward a human blood serum proteome: analysis by multidimensional separation coupled with mass spectrometry," *Mol. Cell. Proteomics* 1(12):947-955 (2002).
Aebersold and Goodlett, "Mass spectrometry in proteomics," *Chem. Rev.* 101(2):269-295 (2001).
Aebi and Hennet, "Congenital disorders of glycosylation: genetic model systems lead the way," *Trends Cell Biol.* 11(3):136-141 (2001).
Anderson and Anderson, "The human plasma proteome: history, character, and diagnostic prospects," *Mol. Cell. Proteomics* 1(11):845-867 (2002).
Anderson and Anderson, "High resolution two-dimensional electrophoresis of human plasma proteins," *Proc. Natl. Acad. Sci. USA* 74(12):5421-5425 (1977).
Baumann et al., "Crystal structure of cleaved human alpha 1-antichymotrypsin at 2.7 A resolution and its comparison with other serpins," *J. Mol. Biol.* 218(3):595-606 (1991).
Bayer et al., "Biocytin hydrazide—a selective label for sialic acids, galactose, and other sugars in glycoconjugates using avidin-biotin technology," *Anal. Biochem.* 170(2):271-281 (1988).
Bergquist et al., "Identification of nuclei associated proteins by 2D-gel electrophoresis and mass spectrometry," *J. Neurosci. Methods* 109(1):3-11 (2001).
Bobbitt, "Periodate oxidation of carbohydrates," *Adv. Carbohydr. Chem.* (48)11:1-41 (1956).
Cohen and Ziy Adeh, "Role of Amadori-modified nonenzymatically glycated serum proteins in the pathogenesis of diabetic nephropathy," *J. Am. Soc. Nephrol.* 7(2):183-190 (1996).
Cramer et al., "Analysis of Phospho- and glycopolypeptides with Infrared Matrix-Assisted Laser Desorption and Ionization," *Analytical Chemistry*, 70(23):4939-4944 (1998).
Durand and Seta, "Protein glycosylation and diseases: blood and urinary oligosaccharides as markers for diagnosis and therapeutic monitoring," *Clin. Chem.* 46(6 Pt 1):795-805 (2000).
Eng et al., *J. Am. Soc. Mass. Spectrom.* 5:976-989 (1994).
Eisen et al., "Cluster analysis and display of genome-wide expression patterns," *Proc. Natl. Acad. Sci. USA* 95(25):14863-14868 (1998).
Ficarro et al., "Phosphoproteome analysis by mass spectrometry and its application to *Saccharomyces cerevisiae*," *Nat. Biotechnol.* 20(3):301-305 (2002).
Fountoulakis et al., "The rat liver mitochondrial proteins," *Electrophoresis* 23(2):311-328 (2002).
Freeze, "Update and perspectives on congenital disorders of glycosylation," *Glycobiology* 11(12):129R-143R (2001).
Geng et al., "Proteomics of glycoproteins based on affinity selection of glycopeptides from tryptic digests," *Journal of chromatography B*, 752(2):293-306 (2001).

(Continued)

*Primary Examiner*—Long V. Le
*Assistant Examiner*—Gary W. Counts
(74) *Attorney, Agent, or Firm*—McDermott Will & Emery LLP

(57) ABSTRACT

The invention provides a method for identifying and quantifying polyglycopeptides in a sample. The method can include the steps of immobilizing glycopolypeptides to a solid support; cleaving the immobilized glycopolypeptides, thereby releasing non-glycosylated peptides and retaining immobilized glycopeptides; releasing the glycopeptides from the solid support; and analyzing the released glycopeptides. The method can further include the step of identifying one or more glycopeptides, for example, using mass spectrometry.

10 Claims, 34 Drawing Sheets

OTHER PUBLICATIONS

Geoghegan and Stroh, "Site-directed conjugation of nonpeptide groups to peptides and proteins via periodate oxidation of a 2-amino alcohol. Application to modification at N-terminal serine," *Bioconjug. Chem.* 3(2):138-146 (1992).

Glazer et al., *Laboratory Techniques in Biochemistry and Molecular Biology: Chemical Modification of Proteins*, Chapter 3, pp. 68-120, Elsevier Biomedical Press, New York (1975).

Goodlett et al., "Protein identification with a single accurate mass of a cysteine-containing peptide and constrained database searching," *Anal. Chem.* 72(6):1112-1118 (2000).

Gygi et al., "Quantitative analysis of complex protein mixtures using isotope-coded affinity tags," *Nat. Biotechnol.* 17(10):994-999 (1999).

Han et al., "Quantitative profiling of differentiation-induced microsomal proteins using isotope-coded affinity tags and mass spectrometry," *Nat. Biotechnol.* 19(10):946-951 (2001).

Haystead et al., "γ-phosphate-linked ATP-sepharose for the affinity purification of protein kinases. Rapid purification to homogeneity of skeletal muscle mitogen-activated protein kinase kinase," *Eur. J. Biochem.* 214(2):459-467 (1993).

Helenius and Aebi, "Intracellular functions of N-linked glycans," *Science* 291(5512):2364-2369 (2001).

Hermanson, *Bioconjugate Techniques*, pp. 3-166, Academic Press, San Diego (1996).

Horoszewicz et al., "The LNCaP cell line—a new model for studies on human prostatic carcinoma," *Prog. Clin. Biol. Res.* 37:115-132 (1980).

Keller et al., "Empirical statistical model to estimate the accuracy of peptide identifications made by MS/MS and database search," *Anal. Chem.* 74(20):5383-5392 (2002).

Kolarich and Altmann, "N-glycan Analysis by <atrix-Assisted Laser Desorption/Ionization Mass Spectrometry of Electrphoretically Separated Nonmammalian Proteins: Application to Peanut Allergan Ara h 1 and Olive Pollen Allergen Ole e 1," *Anal. Biochem.* 285(1):64-75 (2000).

Link et al., "Direct analysis of protein complexes using mass spectrometry," *Nat. Biotechnol.* 17(7):676-682 (1999).

Liu et al., "Analysis and sorting of prostate cancer cell types by flow cytometry," *Prostate* 40(3):192-199 (1999).

Maley et al., "Characterization of glycoproteins and their associated oligosaccharides through the use of endoglycosidases," *Anal. Biochem.* 180(2):195-204 (1989).

Mills et al., "Analysis by matrix assisted laser desorption/ionisation-time of flight mass spectrometry of the post-translational modifications of alpha 1-antitrypsin isoforms separated by two-dimensional polyacrylamide gel electrophoresis," *Proteomics* 1(6):778-786 (2001).

Oda et al., "Enrichment analysis of phosphorylated proteins as a tool for probing the phosphoproteome," *Nat. Biotechnol.* 19(4):379-382 (2001).

Oda et al., "Accurate quantitation of protein expression and site-specific-phosphorylation," *Proc. Natl. Acad. Sci. USA* 96(12):6591-6596 (1999).

Petricoin et al., "Use of proteomic patterns in serum to identify ovarian cancer," *Lancet*, 359(9306):572-577 (2002).

Rappsilber et al., "Large-scale proteomic analysis of the human spliceosome," *Genome Res.* 12(8):1231-1245 (2002).

Roth, "Protein N-glycosylation along the secretory pathway: relationship to organelle topography and function, protein quality control, and cell interactions," *Chem. Rev.* 102(2):285-303 (2002).

Rout et al., "The yeast nuclear pore complex: composition, architecture, and transport mechanism," *J. Cell Biol.* 148(4):635-651 (2000).

Rudd et al., "Glycosylation and the immune system," *Science* 291(5512):2370-2376 (2001).

Schneider and Stephens, "Sequence logos: a new way to display consensus sequences," *Nucleic Acids Res.* 18(20):6097-6100 (1990).

Spahr et al., "Simplification of complex peptide mixtures for proteomic analysis: reversible biotinylation of cysteinyl peptides," *Electrophoresis* 21(9):1635-1650 (2000).

Spiro, "Protein glycosylation: nature, distribution, enzymatic formation, and disease implications of glycopeptide bonds," *Glycobiology* 12(4):43R-56R (2002).

Veenstra et al., "Proteome analysis using selective incorporation of isotopically labeled amino acids," *J. Am. Soc. Mall. Spectrom.* 11(1):78-82 (2000).

Yates et al., "Automated protein identification using microcolumn liquid chromatography-tandem mass spectrometry," *Methods Mol. Biol.* 112:553-569 (1999).

Yates, "Mass spectrometry and the age of the proteome," *J. Mass Spect.* 33(1):1-19 (1998).

Yi et al., "Approaching complete peroxisome characterization by gas-phase fractionation," *Electrophoresis* 23(18):3205-3216 (2002).

Yoshioka et al., "The complete amino acid sequence of the A-chain of human plasma alpha 2HS-glycoprotein," *J. Biol. Chem.* 261(4):1665-1676 (1986).

Zhang et al., "Identification and quantification of N-liked glycoproteins using hydrazide chemistry, stable isotope labeling and mass spectrometry," *Nat. Biotechnol.* 21(6):660-666 (2003).

Zhou et al., "a systematic approach to the analysis of protein phosphorylation," *Nat. Biotechnol.* 19(4):375-378 (2001).

Zhou et al., "Comprehensive proteomic analysis of the human spliceosome," *Nature* 419(6903):182-185 (2002).

\* cited by examiner 8 unique proteins; 6 single hits

| | | | | | | | | | | |
|---|---|---|---|---|---|---|---|---|---|---|
| 1. | 0.9914 | 283 | ./051402a.0830_0830.2 | 1796.1 (+0.6) | 2.7967 | 0.163 | 1183.3 | 1 | 17/24 | GPN:BC022986_1 | +2 | K.NSTLC*DLC*IGI |
| 2. | 0.9938 | 324 | ./051402a.0924_0924.2 | 2392.8 (+0.1) | 3.8459 | 0.347* | 902.7 | 1 | 17/36 | PIR2:I56481 | | L.M#HDYLGNAIAVP |
| 3. | 0.9998 | 279 | ./051402a.0822_0822.2 | 1876.1 (+0.9) | 3.7204 | 0.378 | 1121.3 | 1 | 20/30 | PIR2:JH0494 | +3 | K.YTGNASALFLPE |
| 4. | 0.9957 | 254 | ./051402a.0782_0782.2 | 2479.8 (+1.8) | 3.1847 | 0.235 | 604.6 | 1 | 19/36 | SW:APOH_MOUSE | +2 | K.DYPSAGMNSLYC |
| 5. | 0.9950 | 194 | ./051402a.0700_0700.2 | 1908.1 (+1.9) | 2.7744 | 0.259 | 1287.4 | 1 | 17/24 | SW:CFAH_MOUSE | | K.LIEFTNSTH#DY |
| 6. | 0.9999 | 246 | ./051402a.0772_0772.2 | 2159.5 (+0.1) | 4.6248 | 0.402 | 1128.8 | 1 | 22/30 | SW:COT*_MOUSE | +2 | K.NLINDYVSNQIQG |
| 7. | 0.9987 | 260 | ./051402a.0792_0792.2 | 1842.1 (+1.3) | 3.6408 | 0.254 | 1056.8 | 1 | 19/30 | SW:CUTR_MOUSE | +6 | K.YTGNASALLILPE |
| 8. | 0.9999 | 287 | ./051402a.0838_0838.2 | 2045.5 (+0.1) | 4.7472 | 0.301 | 1998.5 | 1 | 23/30 | SW:HPT_MUSSA | +1 | K.VVLHPNHSVVDIG |
| 9. | 0.9999 | 231 | ./051402a.0752_0752.2 | 1737.0 (+1.3) | 4.3536 | 0.433 | 3162.3 | 1 | 23/24 | SW:HPT_MUSSA | +1 | K.NLIMHSRTASAF |
| 10. | 0.9968 | 188 | ./051402a.0690_0690.2 | 2102.2 (+1.9) | 4.6955 | 0.420 | 1748.6 | 1 | 22/30 | SW:KNG_MOUSE | +1 | K.HSIEHFNNNTDHS |

Figure 10

| | | | | | |
|---|---|---|---|---|---|
| 3.9298 | 0.272* | 1497.8 | 1 | 32/ 80 | IPI:IPI00007221.1 | R.VVGVPYQGNGRTALF#ILPSEGK.M |
| 4.4259 | 0.297* | 1178.7 | 1 | 21/ 40 | IPI:IPI00007221.1 | R.VVGVPYQGNGRTALF#ILPSEGK.M |
| 2.9818 | 0.133 | 914.0 | 1 | 27/ 96 | IPI:IPI00007222.1 | K.GVTSVSQIFHSPDLAIRDTFV*N@RSR.T |
| 4.0143 | 0.382* | 1860.5 | 1 | 34/ 80 | IPI:IPI00007240.1 | K.HGVIISSTVDTYRN@GSSV*EYR.C |
| 4.9100 | 0.453* | 1952.7 | 6 | 25/ 40 | IPI:IPI00007240.1 | K.HGVIISSTVDTYRN@GSSV*EYR.C |
| 3.3810 | 0.115* | 711.5 | 1 | 31/ 84 | IPI:IPI00010234.1 | K.GPSTPLPEDPMUN@V*TEFHTTPK.M |
| 3.4283 | 0.303* | 1361.0 | 1 | 22/ 28 | IPI:IPI00020091.1 | P.QWQCFYNSSYLNV*QR.E |
| 3.9313 | 0.326* | 2485.2 | 1 | 33/ 68 | IPI:IPI00022395.1 | R.AVN@ITTSENLIDDVV*SLIR.G |
| 2.8455 | 0.224* | 820.8 | 6 | 17/ 34 | IPI:IPI00022395.1 | R.AVN@ITTSEN@LIDDV*VSLIR.G |
| 4.1656 | 0.406* | 1927.5 | 1 | 24/ 38 | IPI:IPI00024416.1 | K.TDNSLLDQALQN@DTV*FLNMR.G |
| 4.9909 | 0.191* | 2058.3 | 1 | 32/ 72 | IPI:IPI00032179.1 | K.SLIFN@ETYQDISELV*YGAK.L |
| 4.2321 | 0.439* | 1852.5 | 1 | 23/ 36 | IPI:IPI00032179.1 | K.SLIFNETYQDISELV*YGAK.L |
| 5.3725 | 0.306* | 1781.2 | 1 | 38/ 80 | IPI:IPI00032220.1 | R.VYIHPFHLV*IHN@ESTCEQLAK.A |
| 4.1820 | 0.337* | 1796.7 | 1 | 24/ 40 | IPI:IPI00032220.1 | R.VYIHPFHLV*IHN@ESTCEQLAK.A |

Figure 26

| | | | | | | |
|---|---|---|---|---|---|---|
| 2.7417 | 0.161* | 620.4 | 1 | 16/24 | IPI:IPI00004608.1 | +1 | K.TKPREQFNSTER.V |
| 3.3107 | 0.211* | 977.3 | 1 | 17/20 | IPI:IPI00004608.1 | +1 | K.PREQFN#STER.V |
| 3.2942 | 0.270* | 728.1 | 1 | 16/20 | IPI:IPI00004638.1 | +2 | K.YKM#NSDISSTR.G |
| 2.0628 | 0.166 | 668.5 | 1 | 13/16 | IPI:IPI00004641.1 | | K.TPLTAM#ITK.S |
| 3.3788 | 0.341* | 545.3 | 1 | 17/42 | IPI:IPI00006662.1 | | R.ADGTVNQIEGEATPVNLTEPAK.L |
| 3.7782 | 0.403* | 765.0 | 1 | 20/42 | IPI:IPI00006662.1 | | R.ADGTVNQIEGEATPVNLTEPAK.L |
| 4.4292 | 0.312* | 978.6 | 1 | 18/36 | IPI:IPI00007222.1 | | R.VLSMNSDANLELINTUVAK.N |
| 3.8572 | 1.000* | 1054.7 | 2 | 19/36 | IPI:IPI00007222.1 | | R.VLSMN#SDANLELINTUVAK.N |
| 4.1419 | 0.335* | 1051.3 | 1 | 20/36 | IPI:IPI00007222.1 | | R.VLSMNSDANLELINTUVAK.N |
| 2.7875 | 0.139 | 195.2 | 90 | 26/124 | IPI:IPI00013441.1 | | R.AGEN#DFSIMYSTRKRSAQLWLGPAAPIM#HDCK.P |
| 1.1511 | 0.157* | 132.4 | 156 | 7/10 | IPI:IPI00013712.1 | | R.FSIVMN#.E |
| 2.7042 | 0.160* | 1206.6 | 1 | 16/20 | IPI:IPI00019570.1 | +2 | L.FLN#HSEN#ATAK.D |
| 2.2302 | 0.170* | 885.6 | 1 | 15/20 | IPI:IPI00019570.1 | +2 | L.FLN#HSEMATAK.D |
| 2.6114 | 0.253* | 267.9 | 3 | 15/46 | IPI:IPI00019570.1 | +2 | K.M*VSHHNLTTGATLINEQWLLTTAK.N |

Figure 27

| | | | | | | |
|---|---|---|---|---|---|---|
| 2.1575 | 1.000* | | 21 | 21/ 68 | IPI:IPI00006142.1 | M.N#N#LSEN#YENQGRLQVYM*.N |
| 3.5797 | 0.345* | 538.9 | 1 | 20/ 40 | IPI:IPI00007222.1 | K.VGQLQLSHN#LSLVLVPQMLK.H |
| 3.2974 | 0.211* | 963.4 | 4 | 15/ 36 | IPI:IPI00007222.1 | R.VLSN#NSDANLELINTWVAK.N |
| | | 659.1 | | | | |
| 6.0560 | 0.354* | 1460.7 | 2 | 31/ 92 | IPI:IPI00019570.1 +2 | K.MVSHHN#LTTGATLINEQWLLTTAK.N |
| 5.3020 | 0.401* | 2024.6 | 1 | 25/ 46 | IPI:IPI00019570.1 +2 | K.IVSHHN#LTTGATLINEQWLLTTAK.N |
| 5.1176 | 0.337* | 1874.1 | 4 | 35/ 92 | IPI:IPI00019570.1 +2 | K.M*VSHHNLTTGATLINEQWLLTTAK.N |
| 4.7354 | 0.473* | 824.7 | 1 | 24/ 46 | IPI:IPI00019570.1 +2 | K.M*VSHHN#LTTGATLINEQWLLTTAK.N |
| 4.4349 | 0.310* | 1071.3 | 1 | 32/ 96 | IPI:IPI00019570.1 +2 | K.NLFLNHSEN#HATAKDIAPTLTLYVGK.K |
| 2.7879 | 0.302* | 1194.7 | 3 | 16/ 20 | IPI:IPI00019570.1 +2 | L.FLN#HS.ENATAK.D |
| 3.3246 | 0.344* | 1119.0 | 1 | 19/ 26 | IPI:IPI00021002.1 | K.GAFISNFSM*TVDGK.T |
| 5.5646 | 1.000* | 3308.3 | 3 | 38/ 84 | IPI:IPI00022431.1 | K.AAL&AFNAQWN#G-SNFQLEEISR.A |
| 5.5260 | 0.346* | 2636.1 | 4 | 40/ 92 | IPI:IPI00022463.1 | K.ILRQQHLFGSN#VTDCSGNFCLFR.S |
| 4.4199 | 0.320* | 1579.6 | 2 | 29/ 80 | IPI:IPI00022463.1 | R.QQQHLFGSN#VTDCSGNFCLFR.S |
| 3.2547 | 0.352* | 937.1 | 2 | 14/ 26 | IPI:IPI00022463.1 | G.SN#VTDCSGNFCLFR.S |
| 2.5890 | 0.217* | 512.2 | 3 | 17/ 40 | IPI:IPI00022463.1 | R.QQQHLFGSNVTDCSGNFCLFR.S |
| 4.2571 | 0.308* | 1747.0 | 1 | 22/ 38 | IPI:IPI00023590.1 | K.M*LNTSSLLEQLNEQFNWVSR.L |
| 3.6581 | 0.347* | 1037.1 | 2 | 19/ 26 | IPI:IPI00023590.1 | R.LAN#HLTQGEDQYYLR.V |
| 2.0746 | 0.140* | 191.0 | 192 | 11/ 52 | IPI:IPI00024901.1 | K.AKEN#DEN#CCPITTVFVGN#LSEKASDML.I |
| 3.6310 | 0.164* | 700.6 | 1 | 28/ 64 | IPI:IPI00027265.1 +1 | R.FSDCLESN#SSTQFEVKK.Y |
| 5.8257 | 0.237* | 1155.6 | 2 | 42/120 | IPI:IPI00032180.1 | K.ADTHDEILEGLNFN#LTEIPEAQIHGRQELL.R |
| 6.2152 | 0.413* | 2539.8 | 1 | 46/124 | IPI:IPI00032180.1 | K.ADTHDEILEGLN#FNLTEIPEAQIHGRQELL.T |
| 4.7681 | 0.422* | 486.6 | 2 | 20/ 62 | IPI:IPI00032180.1 | K.ADIHDEILEGLNFN#LTEIPEAQIHGRQELL.T |
| 5.0103 | 0.453* | 1250.1 | 3 | 31/116 | IPI:IPI00032180.1 | R.QLAHQSNSTNIFFSPVSIATAFAM*LSLGTK.A |

METHODS FOR QUANTITATIVE PROTEOME ANALYSIS OF GLYCOPROTEINS

This application claims the benefit of priority of U.S. Provisional application Ser. No. 60/385,707, filed Jun. 3, 2002, and U.S. Provisional application Ser. No. 60/469,361, filed May 9, 2003, each of which the entire contents is incorporated herein by reference.

BACKGROUND OF THE INVENTION

The present invention relates generally to the field of proteomics and more specifically to quantitative analysis of glycoproteins.

Complete genomic sequences and large partial (EST) sequence databases potentially identify every gene in a species. However, the sequences alone do not explain the mechanism of biological and clinical processes because they do not explain how the genes and their products cooperate to carry out a specific process or function. Furthermore, the gene sequence does not predict the amount or the activity of the protein products nor does it answer the questions of whether, how, and at what position(s) a protein may be modified.

Quantitative protein profiling has been recognized as an important approach for profiling the physiological state or pathological state of cells or organisms. Specific expectations of quantitative protein profiles include the possibility to detect diagnostic and prognostic disease markers, to discover proteins as therapeutic targets or to learn about basic biological mechanisms.

Not only do the amounts and type of proteins expressed vary in different pathological states, post-translational modifications of proteins also vary depending on the physiological or pathological state of cells or organisms. Thus, it is important to be able to profile the amount and types of expressed proteins as well as protein modifications.

Glycosylation has long been recognized as the most common post-translational modification affecting the functions of proteins, such as protein stability, enzymatic activity and protein-protein interactions. Differential glycosylation is a major source of protein microheterogeneity. Glycoproteins play key roles in cell communications, signaling and cell adhesion. Changes in carbohydrates in cell surface and body fluid are demonstrated in cancer and other disease states and highlights their importance. However, studies on protein glycosylation have been complicated by the diverse structure of protein glycans and the lack of effective tools to identify the glycosylation site(s) on proteins and of glycan structures. Oligosaccharides can be linked to serine or threonine residues (O-glycosylation) or to asparagine residues (N-glycosylation), and glycoproteins can have different oligosaccharides attached to any given possible site(s).

Among the many post-translation modifications of proteins, glycosylation is a modification that is common to proteins that are exposed to an extracellular environment. For example, proteins expressed on the surface of a cell are exposed to the external environment such as blood or surrounding tissue. Similarly, proteins that are secreted from a cell, for example, into the bloodstream, are commonly glycosylated.

Among the diverse types of proteins expressed by cells, proteins that are integral to or associated with lipid membranes perform a wide range of essential cellular functions. Pores, channels, pumps and transporters facilitate the exchange of membrane impermeable molecules between cellular compartments and between the cell and its extracellular environment. Transmembrane receptors sense changes in the cellular environment and, typically via associated proteins, initiate specific intracellular responses. Cell adhesion proteins mediate cell-specific interactions with other cells and the extracellular matrix. Lipid membranes also provide a hydrophobic environment for biochemical reactions that is dramatically different from that of the cytoplasm and other hydrophilic cellular compartments.

Membrane proteins, in particular those spanning the plasma membrane, are also of considerable diagnostic and therapeutic importance, which is further reinforced due to their easy accessibility. Antisera to proteins that are selectively expressed on the surface of a specific cell type have been used extensively for the classification of cells and for their preparative isolation by fluorescent activated cell sorting or related methods. Membrane proteins, as exemplified by Her2/neu, the abundance of which is modulated in the course of certain diseases such as breast cancer, are commonly used as diagnostic indicators and, less frequently, as therapeutic targets. A humanized monoclonal antibody (Herceptin, Genentech, Palo Alto, Calif.) that specifically recognizes Her2/neu receptors is the basis for a successful therapy of breast cancer, and antibodies to other cell surface proteins are also undergoing clinical trials as anticancer agents. Moreover, the majority of current effective therapeutic agents for diseases such as hypertension and heart disease are receptor antagonists that target and selectively modify the activity of specific membrane proteins. It is therefore apparent that a general technique capable of systematically identifying membrane proteins and of accurately detecting quantitative changes in the membrane protein profiles of different cell populations or tissues would be of considerable importance for biology and for applied biomedical research.

In addition to membrane bound proteins, proteins secreted by cells or shed from the cell surface, including hormones, lymphokines, interferons, transferrin, antibodies, proteases, protease inhibitors, and other factors, perform critical functions with respect to the physiological activity of an organism. Examples of physiologically important secreted proteins include the interferons, lymphokines, protein and peptide hormones. Aberrant availability of such proteins can have grave clinical consequences. It is therefore apparent that the ability to precisely quantitatively profile secreted proteins would be of great importance for the discovery of the mechanisms regulating a wide variety of physiological processes in health and disease and for diagnostic or prognostic purposes. Such secreted proteins are present in body fluids such as blood serum and plasma, cerebrospinal fluid, urine, lung lavage, breast milk, pancreatic juice, and saliva. For example, the presence of increased levels of prostate-specific antigen has been used as a diagnostic marker for prostate cancer. Furthermore, the use of agonists or antagonists or the replacement of soluble secreted proteins is an important mode of therapy for a wide range of diseases.

Quantitative proteomics requires the analysis of complex protein samples. In the case of clinical diagnosis, the ability to obtain appropriate specimens for clinical analysis is important for ease and accuracy of diagnosis. As discussed above, a number of biologically important molecules are secreted and are therefore present in body fluids such as blood and serum, cerebrospinal fluid, saliva, and the like. In addition to the presence of important biological molecules, body fluids also provide an attractive specimen source because body fluids are generally readily accessible and available in reasonable quantities for clinical analysis. It is therefore apparent that a general method for the quantitative analysis of the proteins contained in body fluids in health and disease would be of great diagnostic and clinical importance.

A key problem with the proteomic analysis of serum and many other body fluids is the peculiar protein composition of these specimens. The protein composition is dominated by a few proteins that are extraordinarily abundant, with albumin alone representing 50% of the total plasma proteins. Due to the abundance of these major proteins as well as the presence of multiple modified forms of these abundant proteins, the large number of protein species of lower abundance are obscured or inaccessible by traditional proteomics analysis methods such as two-dimensional electrophoresis (2DE).

The classes of proteins described above, membrane proteins, secreted proteins, and proteins in body fluids have in common that they have a high propensity for being glycosylated, that is, modified post translationally with a carbohydrate structure of varying complexity at one or several amino acid residues. Thus, the analysis of glycoproteins allows characterization of important biological molecules.

Thus, there exists a need for methods of high throughput and quantitative analysis of glycoproteins and glycoprotein profiling. The present invention satisfies this need and provides related advantages as well.

SUMMARY OF THE INVENTION

The invention provides a method for identifying and quantifying polyglycopeptides in a sample. The method can include the steps of immobilizing glycopolypeptides to a solid support; cleaving the immobilized glycopolypeptides, thereby releasing non-glycosylated peptides and retaining immobilized glycopeptides; releasing the glycopeptides from the solid support; and analyzing the released glycopeptides. The method can further include the step of identifying one or more glycopeptides, for example, using mass spectrometry.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10 shows isotopic labeling with Phe and identification of glycopeptides (SEQ ID NOS: 1–10) using MS/MS. The glycopeptides were isolated from 1 µl of mouse ascites fluid.

FIG. 26 shows sequences of heavy isotope labeled synthetic peptide standards (SEQ ID NOS: 11–19) identified by mass spectrometry. V* is the heavy valine and F# is the heavy phenylalanine.

FIG. 27 shows peptides (SEQ ID NOS: 20–29) identified from a series of enzymatic cleavages to release O-linked glycopeptides from hydrazide resin after N-linked glycopeptides were released.

FIG. 28 shows identified N-linked glycopeptides (SEQ ID NOS: 30–48), with the consensus NXT/S motif highlighted.

FIG. 29 shows peptides (SEQ ID NOS: 49–63) identified with O-linked oligosaccharides. These were generated by the removal of the O-linked oligosaccharide chains in the electrospray source. The site of carbohydrate attachment is characterized by a loss of water at Ser or Thr to which the O-linked oligosaccharides were linked. The serine or threonine residues with the 18 Dalton water loss are circled.

DETAILED DESCRIPTION OF THE INVENTION

Figure 1:
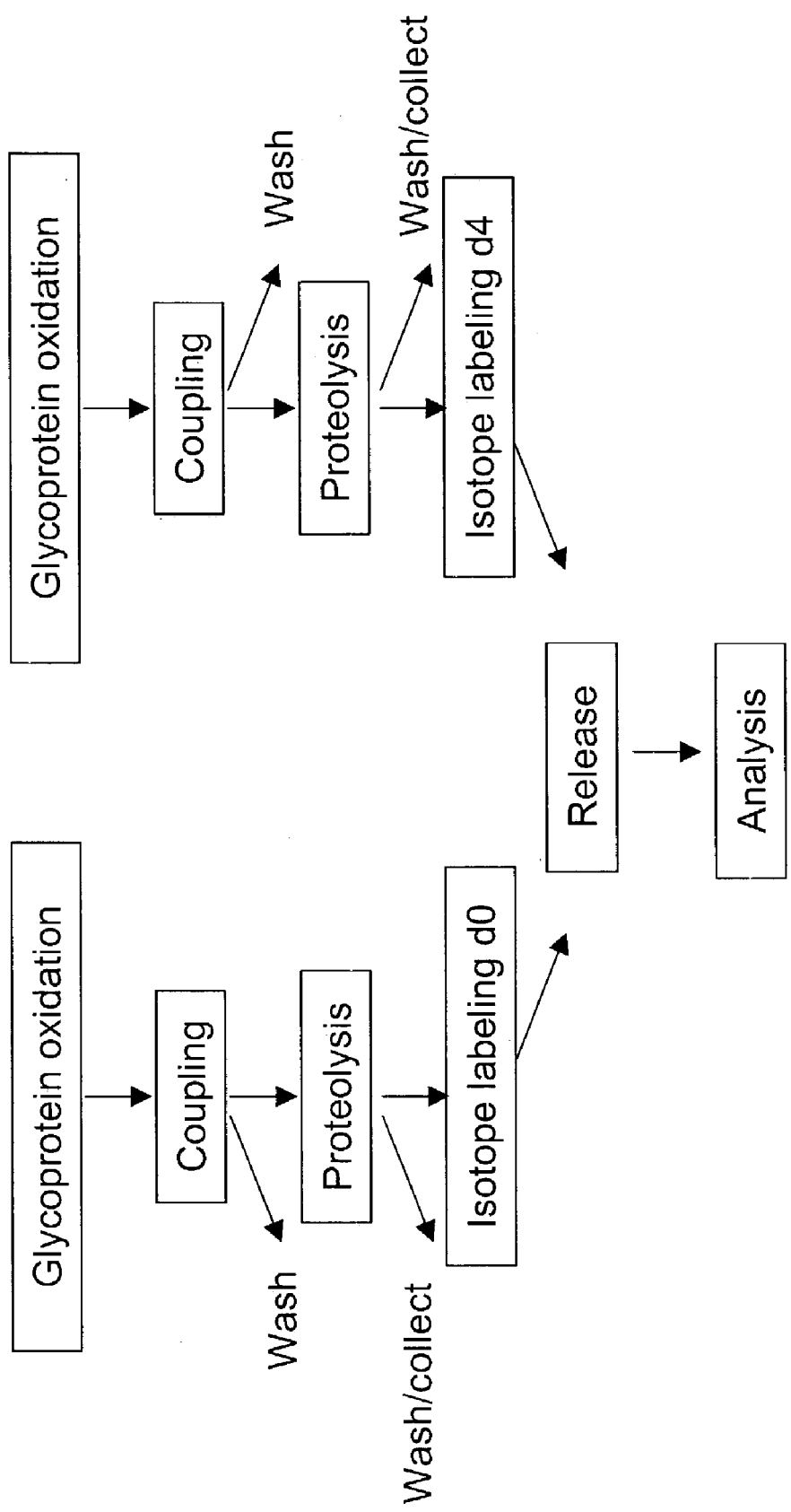
FIG. 1 shows a schematic diagram of an exemplary method of identifying and quantifying glycopolypeptides/glycoproteins and for determining quantitative changes in the glycosylation state of proteins.

The invention provides methods for quantitative profiling of glycoproteins and glycopeptides on a proteome-wide scale. The methods of the invention allow the identification and quantification of glycoproteins in a complex sample and determination of the sites of glycosylation. The methods of the invention can be used to determine changes in the abundance of glycoproteins and changes in the state of glycosylation at individual glycosylation sites on those glycoproteins that occur in response to perturbations of biological systems and organisms in health and disease.

The methods of the invention can be used to purify glycosylated proteins or peptides and identify and quantify the glycosylation sites. Because the methods of the invention are directed to isolating glypolypeptides, the methods also reduce the complexity of analysis since many proteins and fragments of glycoproteins do not contain carbohydrate. This can simplify the analysis of complex biological samples such as serum (see below). The methods of the invention are advantageous for the determination of protein glycosylation in glycome studies and can be used to isolate and identify glycoproteins from cell membrane or body fluids to determine specific glycoprotein changes related to certain disease states or cancer. The methods of the invention can be used for detecting quantitative changes in protein samples containing glycoproteins and to detect their extent of glycosylation. The methods of the invention are applicable for the identification and/or characterization of diagnostic biomarkers, immunotherapy, or other diagnostic or therapeutic applications. The methods of the invention can also be used to evaluate the effectiveness of drugs during drug development, optimal dosing, toxicology, drug targeting, and related therapeutic applications.

In one embodiment, the cis-diol groups of carbohydrates in glycoproteins can be oxidized by periodate oxidation to give a di-aldehyde, which is reactive to a hydrazide gel with an agarose support to form covalent hydrazone bonds. The immobilized glycoproteins are subjected to protease digestion followed by extensive washing to remove the non-glycosylated peptides. The immobilized glycopeptides are released from beads by chemicals or glycosidases. The isolated peptides are analyzed by mass spectrometry (MS), and the glycopeptide sequence and corresponding proteins are identified by MS/MS combined with a database search. The glycopeptides can also be isotopically labeled, for example, at the amino or carboxyl termini to allow the quantities of glycopeptides from different biological samples to be compared.

The methods of the invention are based on selectively isolating glycosylated peptides, or peptides that were glycosylated in the original protein sample, from a complex sample. The sample consists of peptide fragments of proteins generated, for example, by enzymatic digestion or chemical cleavage. A stable isotope tag is introduced into the isolated peptide fragments to facilitate mass spectrometric analysis and accurate quantification of the peptide fragments.

The invention provides a method for identifying and quantifying glycopolypeptides in a sample. The method can include the steps of derivatizing glycopolypeptides in a polypeptide sample, for example, by oxidation; immobilizing the derivatized glycopolypeptides to a solid support; cleaving the immobilized glycopolypeptides, thereby releasing non-glycosylated peptide fragments and retaining immobilized glycopeptide fragments; optionally labeling the immobilized glycopeptide fragments with an isotope tag; releasing the glycopeptide fragments from the solid support, thereby generating released glycopeptide fragments; analyzing the released glycopeptide fragments or their de-glycosylated counterparts using mass spectrometry; and quantifying the amount of the identified glycopeptide fragment. The released glycopolypeptides can be released with the carbohydrate still attached (the glycosylated form) or with the carbohydrate removed (the de-glycosylated form).

An embodiment of the present invention is depicted in FIG. 1. A sample containing glycopolypeptides is chemically modified so that carbohydrates of the glycopolypeptides in the sample can be selectively bound to a solid support. For example, the glycopolypeptides can be bound covalently to a solid support by chemically modifying the carbohydrate so that the carbohydrate can covalently bind to a reactive group on a solid support. In the embodiment depicted in FIG. 1, the carbohydrates of the sample glycopolypeptides are oxidized. The carbohydrate can be oxidized, for example, to aldehydes. The oxidized moiety, such as an aldehyde moiety, of the glycopolypeptides can react with a solid support containing hydrazide or amine moieties, allowing covalent attachment of glycosylated polypeptides to a solid support via hydrazine chemistry. The sample glycopolypeptides are immobilized through the chemically modified carbohydrate, for example, the aldehyde, allowing the removal of non-glycosylated sample proteins by washing of the solid support. If desired, the immobilized glycopolypeptides can be denatured and/or reduced. The immobilized glycopolypeptides are cleaved into fragments using either protease or chemical cleavage. Cleavage results in the release of peptide fragments that do not contain carbohydrate and are therefore not immobilized. These released non-glycosylated peptide fragments optionally can be further characterized, if desired.

Following cleavage, glycosylated peptide fragments (glycopeptide fragments) remain bound to the solid support. To facilitate quantitative mass spectrometry (MS) analysis, immobilized glycopeptide fragments can be isotopically labeled. If it is desired to characterize most or all of the immobilized glycopeptide fragments, the isotope tagging reagent contains an amino or carboxyl reactive group so that the N-terminus or C-terminus of the glycopeptide fragments can be labeled (see FIGS. 1, 3 and 9). The immobilized glycopeptide fragments can be cleaved from the solid support chemically or enzymatically, for example, using glycosidases such as N-glycanase (N-glycosidase) or O-glycanase (O-glycosidase). The released glycopeptide fragments or their deglycosylated forms can be analyzed, for example, using MS.

As used herein, the term "polypeptide" refers to a peptide or polypeptide of two or more amino acids. A polypeptide can also be modified by naturally occurring modifications such as post-translational modifications, including phosphorylation, fatty acylation, prenylation, sulfation, hydroxylation, acetylation, addition of carbohydrate, addition of prosthetic groups or cofactors, formation of disulfide bonds, proteolysis, assembly into macromolecular complexes, and the like. A "peptide fragment" is a peptide of two or more amino acids, generally derived from a larger polypeptide.

As used herein, a "glycopolypeptide" or "glycoprotein" refers to a polypeptide that contains a covalently bound carbohydrate group. The carbohydrate can be a monosaccharide, oligosaccharide or polysaccharide. Proteoglycans are included within the meaning of "glycopolypeptide." A glycopolypeptide can additionally contain other post-translational modifications. A "glycopeptide" refers to a peptide that contains covalently bound carbohydrate. A "glycopeptide fragment" refers to a peptide fragment resulting from enzymatic or chemical cleavage of a larger polypeptide in which the peptide fragment retains covalently bound carbohydrate. It is understood that a glycopeptide fragment or peptide fragment refers to the peptides that result from a particular cleavage reaction, regardless of whether the resulting peptide was present before or after the cleavage reaction. Thus, a peptide that does not contain a cleavage site will be present after the cleavage reaction and is considered to be a peptide fragment resulting from that particular cleavage reaction. For example, if bound glycopeptides are cleaved, the resulting cleavage products retaining bound carbohydrate are considered to be glycopeptide fragments. The glycosylated fragments can remain bound to the solid support, and such bound glycopeptide fragments are considered to include those fragments that were not cleaved due to the absence of a cleavage site.

As disclosed herein, a glycopolypeptide or glycopeptide can be processed such that the carbohydrate is removed from the parent glycopolypeptide. It is understood that such an originally glycosylated polypeptide is still referred to herein as a glycopolypeptide or glycopeptide even if the carbohydrate is removed enzymatically and/or chemically. Thus, a glycopolypeptide or glycopeptide can refer to a glycosylated or de-glycosylated form of a polypeptide. A glycopolypeptide or glycopeptide from which the carbohydrate is removed is referred to as the de-glycosylated form of a polypeptide whereas a glycopolypeptide or glycopeptide which retains its carbohydrate is referred to as the glycosylated form of a polypeptide.

As used herein, the term "sample" is intended to mean any biological fluid, cell, tissue, organ or portion thereof, that includes one or more different molecules such as nucleic acids, polypeptides, or small molecules. A sample can be a tissue section obtained by biopsy, or cells that are placed in or adapted to tissue culture. A sample can also be a biological fluid specimen such as blood, serum or plasma, cerebrospinal fluid, urine, saliva, seminal plasma, pancreatic juice, breast milk, lung lavage, and the like. A sample can additionally be a cell extract from any species, including prokaryotic and eukaryotic cells as well as viruses. A tissue or biological fluid specimen can be further fractionated, if desired, to a fraction containing particular cell types.

As used herein, a "polypeptide sample" refers to a sample containing two or more different polypeptides. A polypeptide sample can include tens, hundreds, or even thousands or more different polypeptides. A polypeptide sample can also include non-protein molecules so long as the sample contains polypeptides. A polypeptide sample can be a whole cell or tissue extract or can be a biological fluid. Furthermore, a polypeptide sample can be fractionated using well known methods, as disclosed herein, into partially or substantially purified protein fractions.

The use of biological fluids such as a body fluid as a sample source is particularly useful in methods of the invention. Biological fluid specimens are generally readily accessible and available in relatively large quantities for clinical analysis. Biological fluids can be used to analyze diagnostic and prognostic markers for various diseases. In addition to ready accessibility, body fluid specimens do not require any prior knowledge of the specific organ or the specific site in an organ that might be affected by disease. Because body fluids, in particular blood, are in contact with numerous body organs, body fluids "pick up" molecular signatures indicating pathology due to secretion or cell lysis associated with a pathological condition. Body fluids also pick up molecular signatures that are suitable for evaluating drug dosage, drug targets and/or toxic effects, as disclosed herein.

Quantitative proteomics, defined as the comparison of relative protein changes in different proteomes, has been recognized as an important component of the emerging science of functional genomics. The technology is expected to facilitate the detection and identification of diagnostic or prognostic disease markers, the discovery of proteins as therapeutic targets and to provide new functional insights into biological processes. Two methods have been used preferentially to generate quantitative profiles of complex protein mixtures. The first and most commonly used is a combination of two-dimensional gel electrophoresis (2DE) and mass spectrometry (MS). The second is a more recently developed technique based on stable isotope tagging of proteins and automated peptide tandem mass spectrometry (Oda et al., *Proc. Natl. Acad. Sci. USA* 96:6591–6596 (1999); Veenstra et al., *J. Am. Soc. Mass. Spectrom.* 11:78–82 (2000); Gygi et al., *Nat. Biotechnol.* 17:994–999 (1999)). To date, neither method has succeeded in determining the complete proteome of any species. This is mainly due to the "top down" mode of operation of either method in which the most abundant proteins are preferentially or exclusively analyzed.

Given the complexities of global proteome analysis, several studies have adopted a "divide and conquer" strategy to handle the "top down" problem by comprehensively analyzing specific subsets of the proteome that are selectively isolated. Such studies include the analysis of functional multiprotein complexes such as the ribosome (Link et al., Nat. Biotechnol. 17:676–682 (1999)), spliceosome (Rapp-silber et al., *Genome Res.* 12:1231–1245 (2002); Zhou et al., *Nature* 419:182–185 (2002)), and nuclear pore complex (Rout et al., *J. Cell Biol.* 148:635–651 (2000)), or organelles, such as mitochondria (Fountoulakis et al., *Electrophoresis* 23:311–328 (2002)), peroxisomes (Yi et al., *Electrophoresis* 23:3205–3216 (2002)), microsomes (Han et al., *Nat. Biotechnol.* 19:946–951 (2001)) and nuclei (Bergquist et al., *J. Neurosci. Methods* 109:3–11 (2001)). Alternatively, proteins that contain common distinguishing structural features, such as phosphate ester groups ((Ficarro et al., *Nat. Biotechnol.* 20:301–305 (2002); Oda et al., *Nat. Biotechnol.* 19:379–382 (2001); Zhou et al., *Nat. Biotechnol.* 19:375–378 (2001)), cysteine residues (Gygi et al. supra (1999); Spahr et al., *Electrophoresis* 21:1635–1650 (2000)) or have the ability to specifically bind to certain compounds (Haystead et al., *Eur. J. Biochem.* 214:459–467 (1993); Adam et al., *Nat. Biotechnol.* 20:805–809 (2002)) have been selectively enriched prior to MS analysis. These strategies have in common that they focus on the in-depth analysis of sub-proteomes of rich biological context, thus minimizing the repeated analyses of abundantly expressed proteins.

The methods of the invention utilize the selective isolation of glycopolypeptides coupled with chemical modification to facilitate MS analysis. Proteins are glycosylated by complex enzymatic mechanisms, typically at the side chains of serine or threonine residues (O-linked) or the side chains of asparagine residues (N-linked). N-linked glycosylation sites generally fall into a sequence motif that can be described as N—X—S/T, where X can be any amino acid except proline. Glycosylation plays an important function in many biological processes (reviewed in Helenius and Aebi, *Science* 291:2364–2369 (2001); Rudd et al., *Science* 291: 2370–2375 (2001)).

Protein glycosylation has long been recognized as a very common post-translational modification. As discussed above, carbohydrates are linked to serine or threonine residues (O-linked glycosylation) or to asparagine residues (N-linked glycosylation) (Varki et al. *Essentials of Glycobiology* Cold Spring Harbor Laboratory (1999)). Protein glycosylation, and in particular N-linked glycosylation, is prevalent in proteins destined for extracellular environments (Roth, *Chem. Rev.* 102:285–303 (2002)). These include proteins on the extracellular side of the plasma membrane, secreted proteins, and proteins contained in body fluids, for example, blood serum, cerebrospinal fluid, urine, breast milk, saliva, lung lavage fluid, pancreatic juice, and the like. These also happen to be the proteins in the human body that are most easily accessible for diagnostic and therapeutic purposes.

Due to the ready accessibility of body fluids exposed to the extracellular surface of cells and the presence of secreted proteins in these fluids, many clinical biomarkers and therapeutic targets are glycoproteins. These include Her2/neu in breast cancer, human chorionic gonadotropin and α-fetoprotein in germ cell tumors, prostate-specific antigen in prostate cancer, and CA125 in ovarian cancer. The Her2/neu receptor is also the target for a successful immunotherapy of breast cancer using the humanized monoclonal antibody Herceptin (Shepard et al., *J. Clin. Immunol.* 11:117–127 (1991)). In addition, changes in the extent of glycosylation and the carbohydrate structure of proteins on the cell surface and in body fluids have been shown to correlate with cancer and other disease states, highlighting the clinical importance of this modification as an indicator or effector of pathologic mechanisms (Durand and Seta, *Clin. Chem.* 46:795–805 (2000); Freeze, *Glycobiology* 11:129R–143R (2001); Spiro, *Glycobiology* 12:43R–56R (2002)). Therefore, a method for the systematic and quantitative analysis of glycoproteins would be of significance for the detection of new potential diagnostic markers and therapeutic targets.

Disclosed herein is a method for quantitative glycoprotein profiling. In one embodiment, the method is based on the conjugation of glycoproteins to a solid support using hydrazide chemistry, stable isotope labeling of glycopeptides, and the specific release of formerly N-linked glycosylated peptides via Peptide-N-Glycosidase F (PNGase F). The recovered peptides are then identified and quantified by tandem mass spectrometry (MS/MS). The method was applied to the analysis of cell surface and serum proteins, as disclosed herein.

To selectively isolate glycopolypeptides, the methods utilize chemistry and/or binding interactions that are specific for carbohydrate moieties. Selective binding of glycopolypeptides refers to the preferential binding of glycopolypeptides over non-glycosylated peptides, as demonstrated in Example II. The methods of the invention can utilize covalent coupling of glycopolypeptides, which is particularly useful for increasing the selective isolation of glycopolypeptides by allowing stringent washing to remove non-specifically bound, non-glycosylated polypeptides.

The carbohydrate moieties of a glycopolypeptide are chemically or enzymatically modified to generate a reactive group that can be selectively bound to a solid support having a corresponding reactive group. In the embodiment depicted in FIG. 2, the carbohydrates of glycopolypeptides are oxidized to aldehydes. The oxidation can be performed, for example, with sodium periodate. The hydroxyl groups of a carbohydrate can also be derivatized by epoxides or oxiranes, alkyl halogen, carbonyldiimidazoles, N,N'-disuccinimidyl carbonates, N-hydroxycuccinimidyl chloroformates, and the like. The hydroxyl groups of a carbohydrate can also be oxidized by enzymes to create reactive groups such as aldehyde groups. For example, galactose oxidase oxidizes terminal galactose or N-acetyl-D-galactose residues to form C-6 aldehyde groups. These derivatized groups can be conjugated to amine- or hydrazide-containing moieties.

The oxidation of hydroxyl groups to aldehyde using sodium periodate is specific for the carbohydrate of a glycopeptide. Sodium periodate can oxidize hydroxyl groups on adjacent carbon atoms, forming an aldehyde for coupling with amine- or hydrazide-containing molecules. Sodium periodate also reacts with hydroxylamine derivatives, compounds containing a primary amine and a secondary hydroxyl group on adjacent carbon atoms. This reaction is used to create reactive aldehydes on N-terminal serine residues of peptides. A serine residue is rare at the N-terminus of a protein. The oxidation to an aldehyde using sodium periodate is therefore specific for the carbohydrate groups of a glycopolypeptide.

Figure 2:
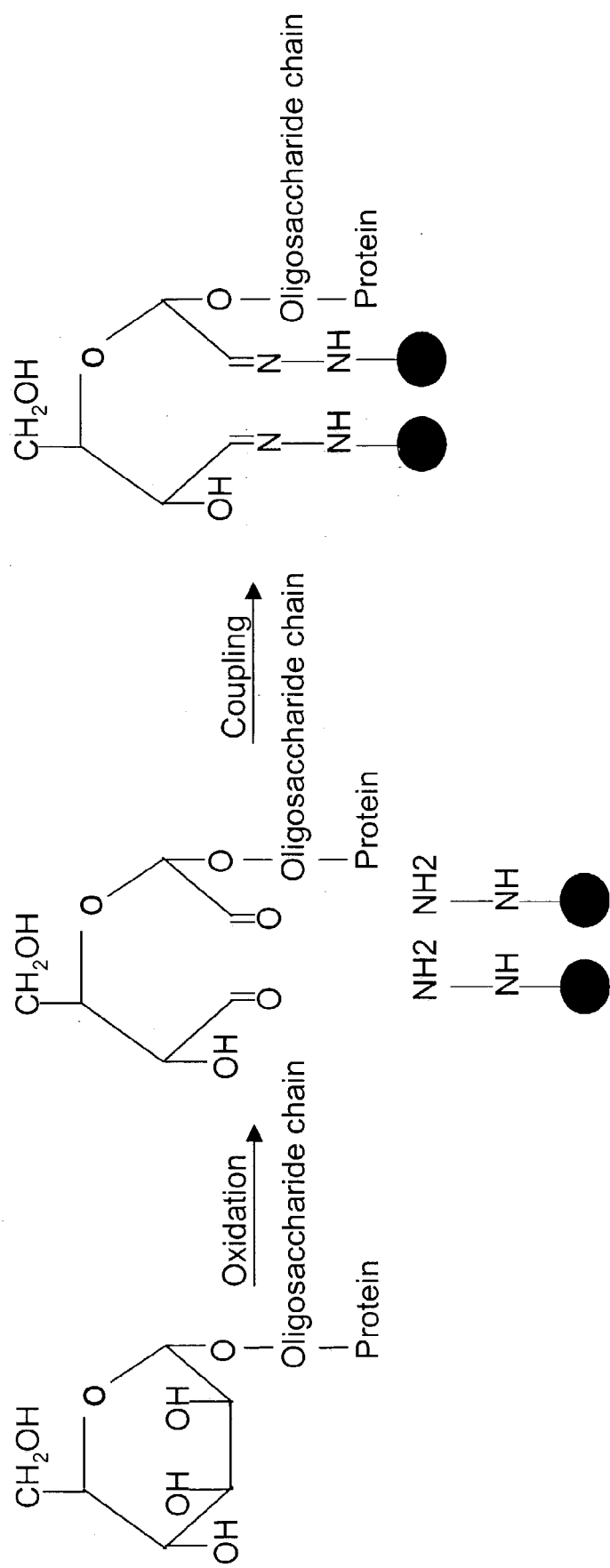
FIG. 2 shows oxidation of a carbohydrate to an aldehyde followed by covalent coupling to hydrazide beads.

Once the carbohydrate of a glycopolypeptide is modified, for example, by oxidition to aldehydes, the modified carbohydrates can bind to a solid support containing hydrazide or amine moieties, such as the hydrazide resin depicted in FIG. 2. Although illustrated with oxidation chemistry and coupling to hydrazide, it is understood that any suitable chemical modifications and/or binding interactions that allows specific binding of the carbohydrate moieties of a glycopolypeptide can be used in methods of the invention. The binding interactions of the glycopolypeptides with the solid support are generally covalent, although non-covalent interactions can also be used so long as the glycopolypeptides or glycopeptide fragments remain bound during the digestion, washing and other steps of the methods.

The methods of the invention can also be used to select and characterize subgroups of carbohydrates. Chemical modifications or enzymatic modifications using, for example, glycosidases can be used to isolate subgroups of carbohydrates. For example, the concentration of sodium periodate can be modulated so that oxidation occurs on sialic acid groups of glycoproteins. In particular, a concentration of about 1 mM of sodium periodate at 0° C. can be used to essentially exclusively modify sialic acid groups.

Glycopolypeptides containing specific monosaccharides can be targeted using a selective sugar oxidase to generate aldehyde functions, such as the galactose oxidase described above or other sugar oxidases. Furthermore, glycopolypeptides containing a subgroup of carbohydrates can be selected after the glycopolypeptides are bound to a solid support. For example, glycopeptides bound to a solid support can be selectively released using different glycosidases having specificity for particular monosaccharide structures.

The glycopolypeptides are isolated by binding to a solid support. The solid support can be, for example, a bead, resin, membrane or disk, or any solid support material suitable for methods of the invention. An advantage of using a solid support to bind the glycopolypeptides is that it allows extensive washing to remove non-glycosylated polypeptides. Thus, in the case of complex samples containing a multitude of polypeptides, the analysis can be simplified by isolating glycopolypeptides and removing the non-glycosylated polypeptides, thus reducing the number of polypeptides to be analyzed.

The glycopolypeptides can also be conjugated to an affinity tag through an amine group, such as biotin hydrazide. The affinity tagged glycopeptides can then be immobilized to the solid support, for example, an avidin or streptavidin solid support, and the non-glycosylated peptides are removed. The glycopeptides immobilized on the solid support can be cleaved by a protease, and the non-glycosylated peptide fragments can be removed by washing. The tagged glycopeptides can be released from the solid support by enzymatic or chemical cleavage. Alternatively, the tagged glycopeptides can be released from the solid support with the oligosaccharide and affinity tag attached (see Example XV and FIGS. 28 and 29).

Another advantage of binding the glycopolypeptides to the solid support is that it allows further manipulation of the sample molecules without the need for additional purification steps that can result in loss of sample molecules. For example, the methods of the invention can involve the steps of cleaving the bound glycopolypeptides as well as adding an isotope tag, or other desired modifications of the bound glycopolypeptides. Because the glycopolypeptides are bound, these steps can be carried out on solid phase while allowing excess reagents to be removed as well as extensive washing prior to subsequent manipulations.

The bound glycopolypeptides can be cleaved into peptide fragments to facilitate MS analysis. Thus, a polypeptide molecule can be enzymatically cleaved with one or more proteases into peptide fragments. Exemplary proteases useful for cleaving polypeptides include trypsin, chymotrypsin, pepsin, papain, *Staphylococcus aureus* (V8) protease, Submaxillaris protease, bromelain, thermolysin, and the like. In certain applications, proteases having cleavage specificities that cleave at fewer sites, such as sequence-specific proteases having specificity for a sequence rather than a single amino acid, can also be used, if desired. Polypeptides can also be cleaved chemically, for example, using CNBr, acid or other chemical reagents. A particularly useful cleavage reagent is the protease trypsin. One skilled in the art can readily determine appropriate conditions for cleavage to achieve a desired efficiency of peptide cleavage.

Cleavage of the bound glycopolypeptides is particularly useful for MS analysis in that one or a few peptides are generally sufficient to identify a parent polypeptide. However, it is understood that cleavage of the bound glycopolypeptides is not required, in particular where the bound glycopolypeptide is relatively small and contains a single glycosylation site. Furthermore, the cleavage reaction can be carried out after binding of glycopolypeptides to the solid support, allowing characterization of non-glycosylated peptide fragments derived from the bound glycopolypeptide. Alternatively, the cleavage reaction can be carried out prior to addition of the glycopeptides to the solid support. One skilled in the art can readily determine the desirability of cleaving the sample polypeptides and an appropriate point to perform the cleavage reaction, as needed for a particular application of the methods of the invention.

If desired, the bound glycopolypeptides can be denatured and optionally reduced. Denaturing and/or reducing the bound glycopolypeptides can be useful prior to cleavage of the glycopolypeptides, in particular protease cleavage, because this allows access to protease cleavage sites that can be masked in the native form of the glycopolypeptides. The bound glycopeptides can be denatured with detergents and/or chaotropic agents. Reducing agents such as β-mercaptoethanol, dithiothreitol, tris-carboxyethylphosphine (TCEP), and the like, can also be used, if desired. As discussed above, the binding of the glycopolypeptides to a solid support allows the denaturation step to be carried out followed by extensive washing to remove denaturants that could inhibit the enzymatic or chemical cleavage reactions. The use of denaturants and/or reducing agents can also be used to dissociate protein complexes in which non-glycosylated proteins form complexes with bound glycopolypeptides. Thus, the use of these agents can be used to increase the specificity for glycopolypeptides by washing away non-glycosylated polypeptides from the solid support.

Treatment of the bound glycopolypeptides with a cleavage reagent results in the generation of peptide fragments. Because the carbohydrate moiety is bound to the solid support, those peptide fragments that contain the glycosylated residue remain bound to the solid support. Following cleavage of the bound glycopolypeptides, glycopeptide fragments remain bound to the solid support via binding of the carbohydrate moiety. Peptide fragments that are not glycosylated are released from the solid support. If desired, the released non-glycosylated peptides can be analyzed, as described in more detail below.

The methods of the invention can be used to identify and/or quantify the amount of a glycopolypeptide present in a sample. A particularly useful method for identifying and quantifying a glycopolypeptide is mass spectrometry (MS). The methods of the invention can be used to identify a glycopolypeptide qualitatively, for example, using MS analysis. If desired, an isotope tag can be added to the bound glycopeptide fragments, in particular to facilitate quantitative analysis by MS.

As used herein an "isotope tag" refers to a chemical moiety having suitable chemical properties for incorporation of an isotope, allowing the generation of chemically identical reagents of different mass which can be used to differentially tag a polypeptide in two samples. The isotope tag also has an appropriate composition to allow incorporation of a stable isotope at one or more atoms. A particularly useful stable isotope pair is hydrogen and deuterium, which can be readily distinguished using mass spectrometry as light and heavy forms, respectively. Any of a number of isotopic atoms can be incorporated into the isotope tag so long as the heavy and light forms can be distinguished using mass spectrometry, for example, $^{13}C$, $^{15}N$, $^{17}O$, $^{18}O$ or $^{34}S$. Exemplary isotope tags include the 4,7,10-trioxa-1,13-tridecanediamine based linker and its related deuterated form, 2,2',3,3',11,11',12,12'-octadeutero-4,7,10-trioxa-1,13-tridecanediamine, described by Gygi et al. (*Nature Biotechnol.* 17:994–999 (1999). Other exemplary isotope tags have also been described previously (see WO 00/11208, which is incorporated herein by reference).

Figure 3:
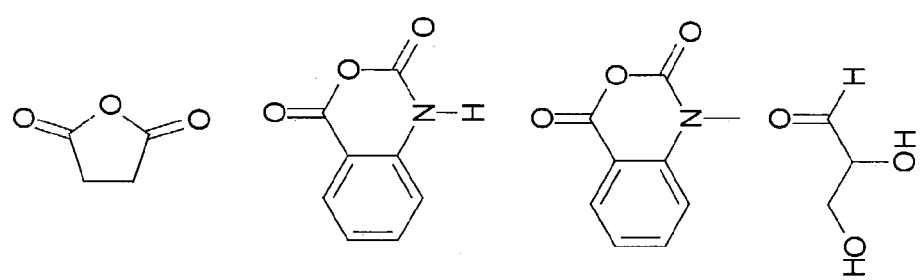
FIG. 3 shows representative chemical reagents that have been tested and proved to be able to label amino groups of glycopeptides. The structures of labeled peptide are listed in the right column.
Figure 3:
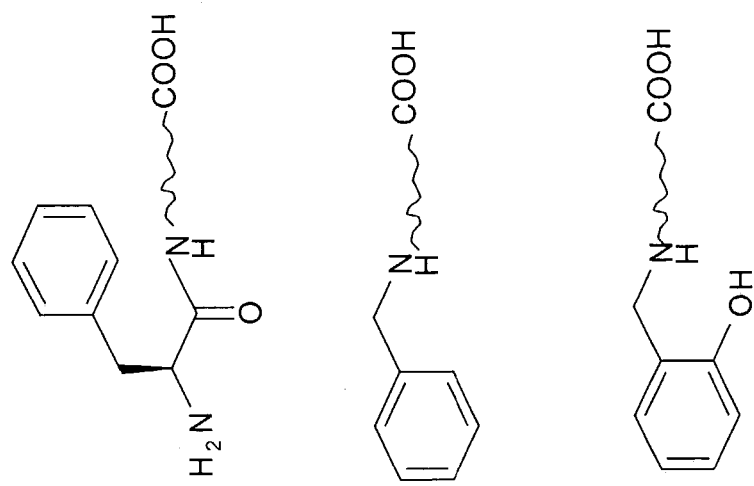
Figure 9:
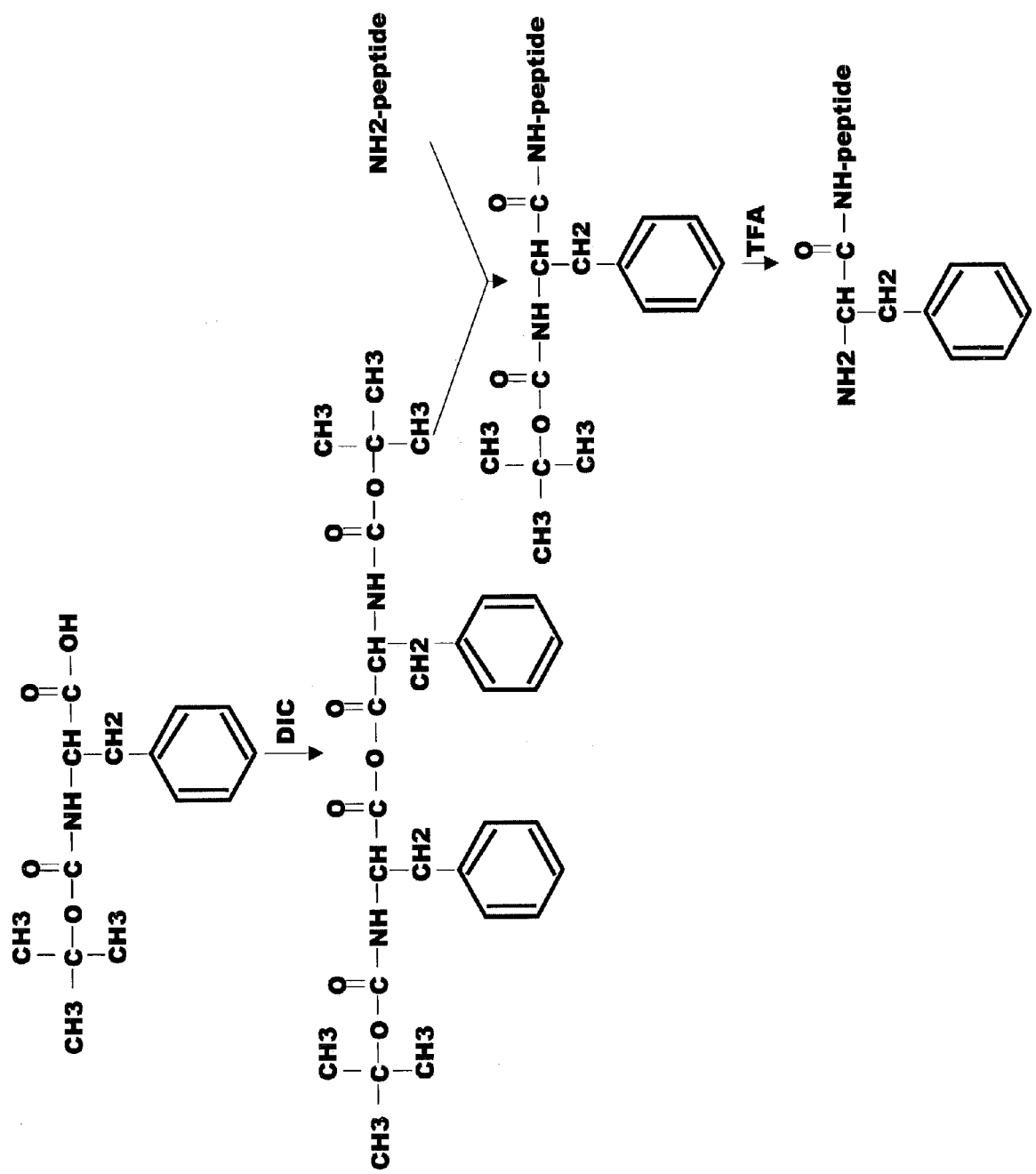
FIG. 9 shows the chemistry and schematic diagram of isotopically labeling the N-termini of the immobilized glycopeptides by attaching differentially isotopically labeled forms of the amino acid phenylalanine (Phe) to their N-termini.

In contrast to these previously described isotope tags related to an ICAT-type reagent, it is not required that an affinity tag be included in the reagent since the glycopolypeptides are already isolated. One skilled in the art can readily determine any of a number of appropriate isotope tags useful in methods of the invention. An isotope tag can be an alkyl, akenyl, alkynyl, alkoxy, aryl, and the like, and can be optionally substituted, for example, with O, S, N, and the like, and can contain an amine, carboxyl, sulfhydryl, and the like (see WO 00/11208). Exemplary isotope tags include succinic anhydride, isatoic-anhydride, N-methyl-isatoic-anhydride, glyceraldehyde, Boc-Phe-OH, benzaldehyde, salicylaldehyde, and the like (FIG. 3). In addition to Phe, as shown in FIGS. 3 and 9, other amino acids similarly can be used as isotope tags. Furthermore, small organic aldehydes, similar to those shown in FIG. 3, can be used as isotope tags. These and other derivatives can be made in the same manner as that disclosed herein using methods well known to those skilled in the art. One skilled in the art will readily recognize that a number of suitable chemical groups can be used as an isotope tag so long as the isotope tag can be differentially isotopically labeled.

The bound glycopeptide fragments are tagged with an isotope tag to facilitate MS analysis. In order to tag the glycopeptide fragments, the isotope tag contains a reactive group that can react with a chemical group on the peptide portion of the glycopeptide fragments. A reactive group is reactive with and therefore can be covalently coupled to a molecule in a sample such as a polypeptide. Reactive groups are well known to those skilled in the art (see, for example, Hermanson, *Bioconjugate Techniques*, pp. 3–166, Academic Press, San Diego (1996); Glazer et al., *Laboratory Techniques in Biochemistry and Molecular Biology: Chemical Modification of Proteins*, Chapter 3, pp. 68–120, Elsevier Biomedical Press, New York (1975); Pierce Catalog (1994), Pierce, Rockford Ill.). Any of a variety of reactive groups can be incorporated into an isotope tag for use in methods of the invention so long as the reactive group can be covalently coupled to the immobilized polypeptide.

To analyze a large number or essentially all of the bound glycopolypeptides, it is desirable to use an isotope tag having a reactive group that will react with the majority of the glycopeptide fragments. For example, a reactive group that reacts with an amino group can react with the free amino group at the N-terminus of the bound glycopeptide fragments. If a cleavage reagent is chosen that leaves a free amino group of the cleaved peptides, such an amino group reactive agent can label a large fraction of the peptide fragments. Only those with a blocked N-terminus would not be labeled. Similarly, a cleavage reagent that leaves a free carboxyl group on the cleaved peptides can be modified with a carboxyl reactive group, resulting in the labeling of many if not all of the peptides. Thus, the inclusion of amino or carboxyl reactive groups in an isotope tag is particularly useful for methods of the invention in which most if not all of the bound glycopeptide fragments are desired to be analyzed.

In addition, a polypeptide can be tagged with an isotope tag via a sulfhydryl reactive group, which can react with free sulfhydryls of cysteine or reduced cystines in a polypeptide. An exemplary sulfhydryl reactive group includes an iodoacetamido group (see Gygi et al., supra, 1999). Other exemplary sulfhydryl reactive groups include maleimides, alkyl and aryl halides, haloacetyls, α-haloacyls, pyridyl disulfides, aziridines, acrylolyls, arylating agents and thiomethylsulfones.

A reactive group can also react with amines such as the α-amino group of a peptide or the ε-amino group of the side chain of Lys, for example, imidoesters, N-hydroxysuccinimidyl esters (NHS), isothiocyanates, isocyanates, acyl azides, sulfonyl chlorides, aldehydes, ketones, glyoxals, epoxides (oxiranes), carbonates, arylating agents, carbodiimides, anhydrides, and the like. A reactive group can also react with carboxyl groups found in Asp or Glu or the C-terminus of a peptide, for example, diazoalkanes, diazoacetyls, carbonyldiimidazole, carbodiimides, and the like. A reactive group that reacts with a hydroxyl group includes, for example, epoxides, oxiranes, carbonyldiimidazoles, N,N'-disuccinimidyl carbonates, N-hydroxycuccinimidyl chloroformates, and the like. A reactive group can also react with amino acids such as histidine, for example, α-haloacids and amides; tyrosine, for example, nitration and iodination; arginine, for example, butanedione, phenylglyoxal, and nitromalondialdehyde; methionine, for example, iodoacetic acid and iodoacetamide; and tryptophan, for example, 2-(2-nitrophenylsulfenyl)-3-methyl-3-bromoindolenine (BNPS-skatole), N-bromosuccinimide, formylation, and sulfenylation (Glazer et al., supra, 1975). In addition, a reactive group can also react with a phosphate group for selective labeling of phosphopeptides (Zhou et al., *Nat. Biotechnol.*, 19:375–378 (2001)) or with other covalently modified peptides, including lipopeptides, or any of the known covalent polypeptide modifications. One skilled in the art can readily determine conditions for modifying sample molecules by using various reagents, incubation conditions and time of incubation to obtain conditions suitable for modification of a molecule with an isotope tag. The use of covalent-chemistry based isolation methods is particularly useful due to the highly specific nature of the binding of the glycopolypeptides.

The reactive groups described above can form a covalent bond with the target sample molecule. However, it is understood that an isotope tag can contain a reactive group that can non-covalently interact with a sample molecule so long as the interaction has high specificity and affinity.

Prior to further analysis, it is generally desirable to release the bound glycopeptide fragments. The glycopeptide fragments can be released by cleaving the fragments from the solid support, either enzymatically or chemically. For example, glycosidases such as N-glycosidases and O-glycosidases can be used to cleave an N-linked or O-linked carbohydrate moiety, respectively, and release the corresponding de-glycosylated peptide(s). If desired, N-glycosidases and O-glycosidases can be added together or sequentially, in either order. The sequential addition of an N-glycosidase and an O-glycosidase allows differential characterization of those released peptides that were N-linked versus those that were O-linked, providing additional information on the nature of the carbohydrate moiety and the modified amino acid residue. Thus, N-linked and O-linked glycosylation sites can be analyzed sequentially and separately on the same sample, increasing the information content of the experiment and simplifying the complexity of the samples being analyzed.

In addition to N-glycosidases and O-glycosidases, other glycosidases can be used to release a bound glycopolypeptide. For example, exoglycosidases can be used. Exoglycosidases are anomeric, residue and linkage specific for terminal monnosaccharides and can be used to release peptides having the corresponding carbohydrate.

In addition to enzymatic cleavage, chemical cleavage can also be used to cleave a carbohydrate moiety to release a bound peptide. For example, O-linked oligosaccharides can be released specifically from a polypeptide via a β-elimination reaction catalyzed by alkali. The reaction can be carried out in about 50 mM NaOH containing about 1 M $NaBH_4$ at about 55° C. for about 12 hours. The time, temperature and concentration of the reagents can be varied so long as a sufficient β-elimination reaction is carried out for the needs of the experiment.

In one embodiment, N-linked oligosaccharides can be released from glycopolypeptides, for example, by hydrazinolysis. Glycopolypeptides can be dried in a desiccator over $P_2O_5$ and NaOH. Anhydrous hydrazine is added and heated at about 100° C. for 10 hours, for example, using a dry heat block.

In addition to using enzymatic or chemical cleavage to release a bound glycopeptide, the solid support can be designed so that bound molecules can be released, regardless of the nature of the bound carbohydrate. The reactive group on the solid support, to which the glycopolypeptide binds, can be linked to the solid support with a cleavable linker. For example, the solid support reactive group can be covalently bound to the solid support via a cleavable linker such as a photocleavable linker. Exemplary photocleavable linkers include, for example, linkers containing o-nitrobenzyl, desyl, trans-o-cinnamoyl, m-nitrophenyl, benzylsulfonyl groups (see, for example, Dorman and Prestwich, *Trends Biotech.* 18:64–77 (2000); Greene and Wuts, *Protective Groups in Organic Synthesis,* 2nd ed., John Wiley & Sons, New York (1991); U.S. Pat. Nos. 5,143,854; 5,986,076; 5,917,016; 5,489,678; 5,405,783). Similarly, the reactive group can be linked to the solid support via a chemically cleavable linker. Release of glycopeptide fragments with the intact carbohydrate is particularly useful if the carbohydrate moiety is to be characterized using well known methods, including mass spectrometry. The use of glycosidases to release de-glycosylated peptide fragments also provides information on the nature of the carbohydrate moiety.

Thus, the invention provides methods for identifying a glycopolypeptide and, furthermore, identifying its glycosylation site. The methods of the invention are applied, as disclosed herein, and the parent glycopolypeptide is identified. The glycosylation site itself can also be identified and consensus motifs determined (Example VII), as well as the carbohydrate moiety, as disclosed herein. The invention further provides glycopolypeptides, glycopeptides and glycosylation sites identified by the methods of the invention.

Glycopolypeptides from a sample are bound to a solid support via the carbohydrate moiety. The bound glycopolypeptides are generally cleaved, for example, using a protease, to generate glycopeptide fragments. As discussed above, a variety of methods can be used to release the bound glycopeptide fragments, thereby generating released glycopeptide fragments. As used herein, a "released glycopeptide fragment" refers to a peptide which was bound to a solid support via a covalently bound carbohydrate moiety and subsequently released from the solid support, regardless of whether the released peptide retains the carbohydrate. In some cases, the method by which the bound glycopeptide fragments are released results in cleavage and removal of the carbohydrate moiety, for example, using glycosidases or chemical cleavage of the carbohydrate moiety. If the solid support is designed so that the reactive group, for example, hydrazide, is attached to the solid support via a cleavable linker, the released glycopeptide fragment retains the carbohydrate moiety. It is understood that, regardless whether a carbohydrate moiety is retained or removed from the released peptide, such peptides are referred to as released glycopeptide fragments.

After isolating glycopolypeptides from a sample and cleaving the glycopolypeptide into fragments, the glycopeptide fragments released from the solid support and the released glycopeptide fragments are identified and/or quantitified. A particularly useful method for analysis of the released glycopeptide fragments is mass spectrometry. A variety of mass spectrometry systems can be employed in the methods of the invention for identifying and/or quantifying a sample molecule such as a released glycopolypeptide fragment. Mass analyzers with high mass accuracy, high sensitivity and high resolution include, but are not limited to, ion trap, triple quadrupole, and time-of-flight, quadrupole time-of-flight mass spectrometeres and Fourier transform ion cyclotron mass analyzers (FT-ICR-MS). Mass spectrometers are typically equipped with matrix-assisted laser desorption (MALDI) and electrospray ionization (ESI) ion sources, although other methods of peptide ionization can also be used. In ion trap MS, analytes are ionized by ESI or MALDI and then put into an ion trap. Trapped ions can then be separately analyzed by MS upon selective release from the ion trap. Fragments can also be generated in the ion trap and analyzed. Sample molecules such as released glycopeptide fragments can be analyzed, for example, by single stage mass spectrometry with a MALDI-TOF or ESI-TOF system. Methods of mass spectrometry analysis are well known to those skilled in the art (see, for example, Yates, *J. Mass Spect.* 33:1–19 (1998); Kinter and Sherman, *Protein Sequencing and Identification Using Tandem Mass Spectrometry,* John Wiley & Sons, New York (2000); Aebersold and Goodlett, *Chem. Rev.* 101:269–295 (2001)).

For high resolution polypeptide fragment separation, liquid chromatography ESI-MS/MS or automated LC-MS/MS, which utilizes capillary reverse phase chromatography as the separation method, can be used (Yates et al., *Methods Mol. Biol.* 112:553–569 (1999)). Data dependent collision-induced dissociation (CID) with dynamic exclusion can also be used as the mass spectrometric method (Goodlett, et al., *Anal. Chem.* 72:1112–1118 (2000)).

Once a peptide is analyzed by MS/MS, the resulting CID spectrum can be compared to databases for the determination of the identity of the isolated glycopeptide. Methods for protein identification using single peptides has been described previously (Aebersold and Goodlett, *Chem. Rev.* 101:269–295 (2001); Yates, *J. Mass Spec.* 33:1–19 (1998)). In particular, it is possible that one or a few peptide fragments can be used to identify a parent polypeptide from which the fragments were derived if the peptides provide a unique signature for the parent polypeptide. Thus, identification of a single glycopeptide, alone or in combination with knowledge of the site of glycosylation, can be used to identify a parent glycopolypeptide from which the glycopeptide fragments were derived. Further information can be obtained by analyzing the nature of the attached tag and the presence of the consensus sequence motif for carbohydrate attachment. For example, if peptides are modified with an N-terminal tag, each released glycopeptide has the specific N-terminal tag, which can be recognized in the fragment ion series of the CID spectra. Furthermore, the presence of a known sequence motif that is found, for example, in N-linked carbohydrate-containing peptides, that is, the consensus sequence NXS/T, can be used as a constraint in database searching of N-glycosylated peptides.

In addition, the identity of the parent glycopolypeptide can be determined by analysis of various characteristics associated with the peptide, for example, its resolution on various chromatographic media or using various fractionation methods. These empirically determined characteristics can be compared to a database of characteristics that uniquely identify a parent polypeptide, which defines a peptide tag.

The use of a peptide tag and related database is used for identifying a polypeptide from a population of polypeptides by determining characteristics associated with a polypeptide, or a peptide fragment thereof, comparing the determined characteristics to a polypeptide identification index, and identifying one or more polypeptides in the polypeptide identification index having the same characteristics (see WO 02/052259). The methods are based on generating a polypeptide identification index, which is a database of characteristics associated with a polypeptide. The polypeptide identification index can be used for comparison of characteristics determined to be associated with a polypeptide from a sample for identification of the polypeptide. Furthermore, the methods can be applied not only to identify a polypeptide but also to quantitate the amount of specific proteins in the sample.

The methods for identifying a polypeptide are applicable to performing quantitative proteome analysis, or comparisons between polypeptide populations that involve both the identification and quantification of sample polypeptides. Such a quantitative analysis can be conveniently performed in two separate stages, if desired. As a first step, a reference polypeptide index is generated representative of the samples to be tested, for example, from a species, cell type or tissue type under investigation, such as a glycopolypeptide sample, as disclosed herein. The second step is the comparison of characteristics associated with an unknown polypeptide with the reference polypeptide index or indices previously generated.

A reference polypeptide index is a database of polypeptide identification codes representing the polypeptides of a particular sample, such as a cell, subcellular fraction, tissue, organ or organism. A polypeptide identification index can be generated that is representative of any number of polypeptides in a sample, including essentially all of the polypeptides potentially expressed in a sample. In methods of the invention directed to identifying glycopolypeptides, the polypeptide identification index is determined for a desired sample such as a serum sample. Once a polypeptide identification index has been generated, the index can be used repeatedly to identify one or more polypeptides in a sample, for example, a sample from an individual potentially having a disease. Thus, a set of characteristics can be determined for glycopeptides that can be correlated with a parent glycopolypeptide, including the amino acid sequence of the glycopeptide, and stored as an index, which can be referenced in a subsequent experiment on a sample treated in substantially the same manner as when the index was generated.

The incorporation of an isotope tag can be used to facilitate quantification of the sample glycopolypeptides. As disclosed previously, the incorporation of an isotope tag provides a method for quantifying the amount of a particular molecule in a sample (Gygi et al., supra, 1999; WO 00/11208). In using an isotope tag, differential isotopes can be incorporated, which can be used to compare a known amount of a standard labeled molecule having a differentially labeled isotope tag from that of a sample molecule, as described in more detail below (see Example XIII). Thus, a standard peptide having a differential isotope can be added at a known concentration and analyzed in the same MS analysis or similar conditions in a parallel MS analysis. A specific, calibrated standard can be added with known absolute amounts to determine an absolute quantity of the glycopolypeptide in the sample. In addition, the standards can be added so that relative quantitation is performed, as described below.

Alternatively, parallel glycosylated sample molecules can be labeled with a different isotopic label and compared side-by-side (see Gygi et al., supra, 1999). This is particularly useful for qualitative analysis or quantitative analysis relative to a control sample. For example, a glycosylated sample derived from a disease state can be compared to a glycosylated sample from a non-disease state by differentially labeling the two samples, as described previously (Gygi et al., supra, 1999). Such an approach allows detection of differential states of glycosylation, which is facilitated by the use of differential isotope tags for the two samples, and can thus be used to correlate differences in glycosylation as a diagnostic marker for a disease (see Examples VIII, IX, XI and XII).

The methods of the invention provide numerous advantages for the analysis of complex biological and clinical samples. From every glycoprotein present in a complex sample, only a few peptides will be isolated since only a few peptides of a glycoprotein are glycosylated. Therefore, by isolating glycopeptide fragments, the composition of the resulting peptide mixture is significantly simplified for mass spectrometric analysis. For example, every protein on average will produce dozens of tryptic peptides but only one to a few tryptic glycosylated peptides. For example, the number of glycopeptides is significantly lower than the number of tryptic peptides or Cys-containing peptides in the major plasma proteins (see Table 1). Thus, analysis of glycopolypeptides or glycopeptides reduces the complexity of complex biological samples, for example, serum.

TABLE 1

Five major plasma proteins represent more than 80% total protein

| Protein | Number of Peptides | | |
|---|---|---|---|
| | Tryptic | Cys | Glyco |
| Albumin (40 mg/ml) | 82 | 27 | 0 |
| α1-antitrypsin (3 mg/ml) | 39 | 2 | 3 |
| α2-macroglobulin | 125 | 24 | 8 |
| Transferrin | 79 | 37 | 2 |
| γ-Globulin | 15 | 4 | 2 |
| Total | 340 | 94 | 15 |

Another advantage of the methods of the invention is the use for analysis of body fluids as a clinical specimen, in particular serum. Five major plasma proteins represent more than 80% of the total protein in plasma, albumin, α1 antitrypsin, α2 macroglobulin, transferrin, and γ-globulins. Of these, albumin is the most abundant protein in blood serum and other body fluids, constituting about 50% of the total protein in plasma. However, albumin is essentially transparent to the methods of the invention due to the lack of N-glycosylation. For example, no tryptic N-glycosylated peptides from albumin were observed when the methods of the invention were applied and a N-glycosidase was used to release the N-linked glycopeptides. This is all the more significant because more than 50 different albumin species have been detected by 2D gel electrophoresis that collectively obscure a significant part of the gel pattern and the analysis of less abundant serum proteins having clinical significance. Therefore, the methods of the invention that allow analysis of glycosylated proteins compensate for the dominance of albumin in serum and allow the analysis of less abundant, glycosylated proteins present in serum. As disclosed herein, the methods of the invention allowed the identification of many more serum proteins compared to conventional methods (see Example II). The methods of the invention also allow the analysis of less abundant serum proteins. These low abundance serum proteins are potential diagnostic markers. Such markers can be readily determined by comparing disease samples with healthy samples, as disclosed herein (see Examples VIII, IX, XI and XII).

Additionally, the known sequence motif for N-glycosylation (N—X—S/T) serves as a powerful sequence database search contraint for the identification of the isolated peptides. This can be used to facilitate the identification of the polypeptide from which the glycopeptide fragment was derived since a smaller number of possible peptides will contain the glycosylation motif.

The methods of the invention are also advantageous because they allow fast throughput and simplicity. Accordingly, the methods can be readily adapted for high throughput analysis of samples, which can be particularly advantageous for the analysis of clinical samples. Furthermore, the methods of the invention can be automated to facilitate the processing of multiple samples (see Example XVI). As disclosed herein, a robotic workstation has been adapted for automated glycoprotein analysis (Example XVI).

In addition to the analysis of body fluids for the reasons described above, the methods of the invention are also advantageous for the analysis of proteins contained in the plasma membrane. The methods of the invention allow for the selective separation of cell surface proteins and secreted proteins based on the fact that the proteins most likely contaminating such specimens, intracellular proteins, are very unlikely to be glycosylated. Thus, the methods of the invention can be used to more accurately reflect proteins representative of the sample rather than contaminants from cell lysis. Such an analysis can be optionally combined with subcellular fractionation for the analysis of glycopolypeptides (Example IV).

As described above, non-glycosylated peptide fragments are released from the solid support after proteolytic or chemical cleavage (see FIG. 1). If desired, the released peptide fragments can be characterized to provide further information on the nature of the glycopolypeptides isolated from the sample. A particularly useful method is the use of the isotope-coded affinity tag (ICAT™) method (Gygi et al., Nature Biotechnol. 17:994–999 (1999) which is incorporated herein by reference). The ICAT™ type reagent method uses an affinity tag that can be differentially labeled with an isotope that is readily distinguished using mass spectrometry. The ICAT™ type affinity reagent consists of three elements, an affinity tag, a linker and a reactive group.

One element of the ICAT™ type affinity reagent is an affinity tag that allows isolation of peptides coupled to the affinity reagent by binding to a cognate binding partner of the affinity tag. A particularly useful affinity tag is biotin, which binds with high affinity to its cognate binding partner avidin, or related molecules such as streptavidin, and is therefore stable to further biochemical manipulations. Any affinity tag can be used so long as it provides sufficient binding affinity to its cognate binding partner to allow isolation of peptides coupled to the ICAT™ type affinity reagent. An affinity tag can also be used to isolate a tagged peptide with magnetic beads or other magnetic format suitable to isolate a magnetic affinity tag. In the ICAT™ type reagent method, or any other method of affinity tagging a peptide, the use of covalent trapping, for example, using a cross-linking reagent, can be used to bind the tagged peptides to a solid support, if desired.

A second element of the ICAT™ type affinity reagent is a linker that can incorporate a stable isotope. The linker has a sufficient length to allow the reactive group to bind to a specimen polypeptide and the affinity tag to bind to its cognate binding partner. The linker also has an appropriate composition to allow incorporation of a stable isotope at one or more atoms. A particularly useful stable isotope pair is hydrogen and deuterium, which can be readily distinguished using mass spectrometry as light and heavy forms, respectively. Any of a number of isotopic atoms can be incorporated into the linker so long as the heavy and light forms can be distinguished using mass spectrometry. Exemplary linkers include the 4,7,10-trioxa-1,13-tridecanediamine based linker and its related deuterated form, 2,2',3,3',11,11',12,12'-octadeutero-4,7,10-trioxa-1,13-tridecanediamine, described by Gygi et al. (supra, 1999). One skilled in the art can readily determine any of a number of appropriate linkers useful in an ICAT™ type affinity reagent that satisfy the above-described criteria, as described above for the isotope tag.

The third element of the ICAT™ type-affinity reagent is a reactive group, which can be covalently coupled to a polypeptide in a specimen. Various reactive groups have been described above with respect to the isotope tag and can similarly be incorporated into an ICAT-type reagent.

The ICAT™ method or other similar methods can be applied to the analysis of the non-glycosylated peptide fragments released from the solid support. Alternatively, the ICAT™ method or other similar methods can be applied prior to cleavage of the bound glycopolypeptides, that is, while the intact glycopolypeptide is still bound to the solid support.

The method generally involves the steps of automated tandem mass spectrometry and sequence database searching for peptide/protein identification; stable isotope tagging for quantification by mass spectrometry based on stable isotope dilution theory; and the use of specific chemical reactions for the selective isolation of specific peptides. For example, the previously described ICAT™ reagent contained a sulf-hydryl reactive group, and therefore an ICAT™-type reagent can be used to label cysteine-containing peptide fragments released from the solid support. Other reactive groups, as described above, can also be used.

The analysis of the non-glycosylated peptides, in conjunction with the methods of analyzing glycosylated peptides, provides additional information on the state of polypeptide expression in the sample. By analyzing both the glycopeptide fragments as well as the non-glycosylated peptides, changes in glycoprotein abundance as well as changes in the state of glycosylation at a particular glycosylation site can be readily determined.

If desired, the sample can be fractionated by a number of known fractionation techniques. Fractionation techniques can be applied at any of a number of suitable points in the methods of the invention. For example, a sample can be fractionated prior to oxidation and/or binding of glycopolypeptides to a solid support. Thus, if desired, a substantially purified fraction of glycopolypeptide(s) can be used for immobilization of sample glycopolypeptides. Furthermore, fractionation/purification steps can be applied to non-glycosylated peptides or glycopeptides after release from the solid support. One skilled in the art can readily determine appropriate steps for fractionating sample molecules based on the needs of the particular application of methods of the invention.

Methods for fractionating sample molecules are well known to those skilled in the art. Fractionation methods include but are not limited to subcellular fractionation or chromatographic techniques such as ion exchange, including strong and weak anion and cation exchange resins, hydrophobic and reverse phase, size exclusion, affinity, hydrophobic charge-induction chromatography, dye-binding, and the like (Ausubel et al., *Current Protocols in Molecular Biology* (Supplement 56), John Wiley & Sons, New York (2001); Scopes, *Protein Purification: Principles and Practice*, third edition, Springer-Verlag, New York (1993)). Other fractionation methods include, for example, centrifugation, electrophoresis, the use of salts, and the like (see Scopes, supra, 1993). In the case of analyzing membrane glycoproteins, well known solubilization conditions can be applied to extract membrane bound proteins, for example, the use of denaturing and/or non-denaturing detergents (Scopes, supra, 1993).

Affinity chromatography can also be used including, for example, dye-binding resins such as Cibacron blue, substrate analogs, including analogs of cofactors such as ATP, NAD, and the like, ligands, specific antibodies useful for immuno-affinity isolation, either polyclonal or monoclonal, and the like. A subset of glycopolypeptides can be isolated using lectin affinity chromatography, if desired. An exemplary affinity resin includes affinity resins that bind to specific moieties that can be incorporated into a polypeptide such as an avidin resin that binds to a biotin tag on a sample molecule labeled with an ICAT™-type reagent. The resolution and capacity of particular chromatographic media are known in the art and can be determined by those skilled in the art. The usefulness of a particular chromatographic separation for a particular application can similarly be assessed by those skilled in the art.

Those of skill in the art will be able to determine the appropriate chromatography conditions for a particular sample size or composition and will know how to obtain reproducible results for chromatographic separations under defined buffer, column dimension, and flow rate conditions. The fractionation methods can optionally include the use of an internal standard for assessing the reproducibility of a particular chromatographic application or other fractionation method. Appropriate internal standards will vary depending on the chromatographic medium or the fractionation method used. Those skilled in the art will be able to determine an internal standard applicable to a method of fractionation such as chromatography. Furthermore, electrophoresis, including gel electrophoresis or capillary electrophoresis, can also be used to fractionate sample molecules.

The invention also provides a method for identifying and quantifying glycopeptides in a sample. The method includes the steps of immobilizing glycopolypeptides to a solid support; cleaving the immobilized glycopolypeptides, thereby releasing non-glycosylated peptides and retaining immobilized glycopeptides; labeling the immobilized glycopeptides with an isotope tag; releasing the glycopeptides from the solid support; and analyzing the released glycopeptides.

The methods of the invention can be used in a wide range of applications in basic and clinical biology. The methods of the invention can be used for the detection of changes in the profile of proteins expressed in the plasma membrane, changes in the composition of proteins secreted by cells and tissues, changes in the protein composition of body fluids including blood and seminal plasma, cerebrospinal fluid, pancreatic juice, urine, breast milk, lung lavage, and the like. Since many of the proteins in these samples are glycosylated, the methods of the invention allow the convenient analysis of glycoproteins in these samples. Detected changes observed in a disease state can be used as diagnostic or prognostic markers for a wide range of diseases, including congenital disorders of glycosylation (Example XI) or any disorder involving aberrant glycosylation; cancer, such as skin, prostate, breast, colon, lung, and others (Examples VIII and IX); metabolic diseases or processes such as diabetes (Example XII) or changes in physiological state (Example X); inflammatory diseases such as rheumatoid arthritis; mental disorders or neurological processes; infectious disease; immune response to pathogens; and the like. Furthermore, the methods of the invention can be used for the identification of potential targets for a variety of therapies including antibody-dependent cell cytotoxicity directed against cell surface proteins and for detection of proteins accessible to drugs.

Thus, the methods of the invention can be used to identify diagnostic markers for a disease by comparing a sample from a patient having a disease to a sample from a healthy individual or group of individuals. By comparing disease and healthy samples, a diagnostic pattern can be determined with increases or decreases in expression of particular glycopolypeptides correlated with the disease, which can be used for subsequent analysis of samples for diagnostic purposes (see Examples VIII, IX, XI and XII). The methods are based on analysis of glycopolypeptides, and such an analysis is sufficient for diagnostic purposes.

Thus, the invention provides a method for identifying diagnostic glycopolypeptide markers by using a method of the invention and comparing samples from diseased individual(s) to healthy individual(s) and identifying glycopolypeptides having differential expression between the two samples, whereby differences in expression indicates a correlation with the disease and thus can function as a diagnostic marker. The invention also provides the diagnostic markers identified using methods of the invention.

Furthermore, glycopolypeptides exhibiting differential expression are potential therapeutic targets. Because they are differentially expressed, modulating the activity of these glycopolypeptides can potentially be used to ameliorate a sign or symptom associated with the disease. Thus, the invention provides a method for identifying therapeutic glycopolypeptide targets of a disease. Once a glycopolypeptide is found to be differentially expressed, the potential target can be screened for potential therapeutic agents that modulate the activity of the therapeutic glycopolypeptide target. Methods of generating libraries and screening the libraries for potential therapeutic activity are well known to those skilled in the art. Methods for producing pluralities of compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art (see, for example, in Huse, U.S. Pat. No. 5,264,563; Francis et al., *Curr. Opin. Chem. Biol.* 2:422–428 (1998); Tietze et al., *Curr. Biol.,* 2:363–371 (1998); Sofia, Mol. Divers. 3:75–94 (1998); Eichler et al., *Med. Res. Rev.* 15:481–496 (1995); Gordon et al., J. Med. Chem. 37: 1233–1251 (1994); Gordon et al., *J. Med. Chem.* 37: 1385–1401 (1994); Gordon et al., *Acc. Chem. Res.* 29:144–154 (1996); Wilson and Czarnik, eds., *Combinatorial Chemistry: Synthesis and Application,* John Wiley & Sons, New York (1997)). The invention additionally provides glycopolypeptide therapeutic targets identified by methods of the invention.

The methods can be used for a variety of clinical and diagnostic applications. Known therapeutic methods effected through glycopolypeptides can be characterized by methods of the invention. For example, therapies such as Enbrel™ and Herceptin function through glycoproteins. The methods of the invention allow characterization of individual patients with respect to glycoprotein expression, which can be used to determine likely efficacy of therapy involving glycoproteins.

Thus, the methods of the invention can be used in a variety of applications including, but not limited to, the following applications. The methods of the invention can be used, for example, for blood serum profiling for the detection of prognostic and diagnostic protein markers (see Examples VIII, IX, XI and XII). The methods of the invention can also be used for quantitative profiling of cell surface proteins for the detection of diagnostic/prognostic protein markers and the detection of potential targets of therapy (Example IV). For example, the methods of the invention can be used for antibody-dependent cellular cytotoxicity (ADCC) or other types of therapy. The methods of the invention are applicable in clinical and diagnostic medicine, veterinary medicine, agriculture, and the like. For example, the methods of the invention can be used to identify and/or validate drug targets and to evaluate drug efficacy, drug dosing, and/or drug toxicity. In such a case, the blood proteome, that is serum, can be analyzed using the methods disclosed herein to look for changes in serum glycopolypeptide profiles associated with drug administration and correlated with the effects of drug efficacy, dosing and/or toxicity, and/or validation of drug targets. Such a correlation can be readily determined by collecting serum samples from one or more individuals administered various drug doses, experiencing drug toxicity, experiencing a desired efficacy, and the like. In addition, a serum profile can be generated in combination with the analysis of drug targets as a way to rapidly and efficiently validate a particular target with the administration of a drug or various drug doses, toxicity, and the like. Thus, serum (blood samples) provide a surrogate marker for the status of an individual and his or her ability to respond to a pharmacological intervention.

The methods of the invention can additionally be used for quantitative protein profiling in various body fluids in addition to blood plasma, including CSF, pancreatic juice, lung lavage fluid, seminal plasma, urine, breast milk, and the like. The methods of the invention can also be used for quantitative protein profiling of proteins secreted by cells or tissues for the detection of new protein and peptide hormones and other factors. Thus, the invention provides a method to generate quantitative profiles of glycoproteins. The invention also provides a method for quantifying a glycopolypeptide in a sample, as disclosed herein. The invention further provides a method for the detection of prognostic or diagnostic patterns in blood serum and other body fluids. The invention additionally provides a method for the detection of secreted protein hormones and regulatory factors. Thus, the invention provides a method for profiling glycopolypeptides from body fluids, secreted proteins and cell surface proteins.

The methods of the invention are also applicable to the detection of changes in the state of glycosylation of proteins based on the concurrent application of protein abundance measurement and measurement of protein glycosylation on the same sample. Thus, the invention provides a method to detect quantitative changes in the glycosylation pattern of specific proteins.

The invention also provides a method for the systematic detection of glycosylation sites on proteins. Because the methods of the invention allow the identification of peptide fragments that are glycosylated, this also serves as the identification of the site of glycosylation (Example VII).

Although the methods disclosed herein have generally been described for the analysis of glycopolypeptides, similar methods are also applicable to the analysis of other carbohydrate-containing molecules. Because the methods are based on the specific binding of carbohydrate moieties, the methods of modification and/or isolation can similarly be applied to other carbohydrate-containing molecules. For example, method steps analogous to those disclosed herein can be applied to the identification and quantification of glycosylated molecules such as glycolipids, glycosphingolipids, and the like.

The invention also provides reagents and kits for isolating and quantifying glycopolypeptides. The kit can contain, for example, hydrazide resin or other suitably reactive resin for solid phase capture of glycopolypeptides, a reagent for modification of carbohydrate moieties, for example, an oxidizing reagent such as periodate, and a set of two or more differentially labeled isotope tags for coupling to two different samples, which are particularly useful for quantitative analysis using mass spectrometry. In one embodiment, the invention provides a kit comprising a hydrazide resin, periodate, and a pair of differentially labeled isotope tags. The contents of the kit of the invention, for example, any resins or labeling reagents, are contained in suitable packaging material, and, if desired, a sterile, contaminant-free environment. In addition, the packaging material contains instructions indicating how the materials within the kit can be employed to label sample molecules. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

The methods of the invention can be facilitated by the use of combinations of hardware and software suitable for analysis of methods of the invention. For example, a robotics workstation was developed to facilitate automated glycopeptide analysis (Example XVI). A computer program can be used to find patterns of proteins and/or peptides that are specifically present or present at specific abundances in a sample from a person with a specific disease (see Examples). For example, a number of serum samples can be analyzed and compared to serum samples from healthy individuals. An algorithm is used to find those peptides and/or proteins that are either individually or collectively diagnostic for the disease or the stage of the disease being examined.

In another embodiment, the invention provides a method for identifying and quantifying glycopeptides in a sample. The method can include the steps of immobilizing glycopolypeptides to a solid support; cleaving the immobilized glycopolypeptides, thereby releasing non-glycosylated peptides and retaining immobilized glycopeptides; releasing the glycopeptides from the solid support; and analyzing the released glycopeptides. The method can further include the step of identifying one or more glycopeptides, for example, using mass spectrometry.

In still another embodiment, the invention provides a method of identifying a diagnostic marker for a disease. The method can include the steps of immobilizing glycopolypeptides from a test sample to a first solid support; immobilizing glycopolypeptides from a control sample to a second solid support; cleaving the immobilized glycopolypeptides, thereby releasing non-glycosylated peptides and retaining immobilized glycopeptides; labeling the immobilized glycopeptides on the first and second supports with differential isotope tags on the respective supports; releasing the glycopeptides from the solid supports; analyzing the released glycopeptides; and identifying one or more glycosylated polypeptides having differential glycosylation between the test sample and the control sample. Alternatively, the test and control samples can be run in parallel and analyzed separately. In such a case, the glycopeptides are identified and compared without using differential isotope tagging.

The test sample can be, for example, a specimen from an individual having a disease. The control sample can be, for example, a corresponding specimen obtained from a healthy individual. The sample can be, for example, serum or a tissue biopsy, as described herein. Differential glycosylation can be a qualitative difference, for example, the presence or absence of a glycopolypeptide in the test sample compared to the control sample. Differential glycosylation can also be a quantitative difference. The determination of quantitative differences can be facilitated by the labeling with differential isotope tags such that the samples can be mixed and compared side-by-side, as disclosed herein and described in Gygi et al., supra, 1999. One or more glycopolypeptides exhibiting differential glycosylation are potential diagnostic markers for the respective disease. Such a method provides a glycopolypeptide disease profile, which can be used subsequently for diagnostic purposes. Accordingly, rather than using one or a few diagnostic markers, the methods of the invention allow the identification of a profile of diagnostic markers, which can provide more detailed information on the type of disease, the stage of disease, and/or the prognosis of a disease by determining profiles correlated with the type, stage and/or prognosis of a disease.

In yet another embodiment, the invention provides a method of diagnosing a disease. The method can include the steps of immobilizing glycopolypeptides from a test sample to a solid support; cleaving the immobilized glycopolypeptides, thereby releasing non-glycosylated peptides and retaining immobilized glycopeptides; releasing the glycopeptides from the solid support; analyzing the released glycopeptides; and identifying one or more diagnostic markers associated with a disease, for example, as determined by methods of the invention, as described above.

A test sample from an individual to be tested for a disease or suspected of having a disease can be processed as described for glycopeptide analysis by the methods disclosed herein. The resulting glycopeptide profile from the test sample can be compared to a control sample to determine if changes in glycosylation of diagnostic markers has occurred, as discussed above. Alternatively, the glycopeptide profile can be compared to a known set of diagnostic markers or a database containing information on diagnostic markers.

In another embodiment, the method of diagnosing a disease can include the step of generating a report on the results of the diagnostic test. For example, the report can indicate whether an individual is likely to have a disease or is likely to be disease free based on the presence of a sufficient number of diagnostic markers associated with a disease. The invention further provides a report of the outcome of a method of diagnosing a disease. Similar reports and preparation of such reports are provided for other methods of the invention.

It is understood that the methods of the invention can be performed in any order suitable for glycopolypeptide analysis. One skilled in the art can readily determine an appropriate order of carrying out steps of methods of the invention suitable for glycopeptide analysis.

It is understood that modifications which do not substantially affect the activity of the various embodiments of this invention are also provided within the definition of the invention provided herein. Accordingly, the following examples are intended to illustrate but not limit the present invention.

EXAMPLE I

Quantitative Analysis of Glycopeptides

This example describes purification of glycopeptides and differential labeling with isotope tags.

An embodiment of a method of the invention is schematically illustrated in FIG. 1. The method can include the following steps: (1) Glycoprotein oxidation: Oxidation, for example, with periodate, converts the cis-diol groups of carbohydrates to aldehydes (FIG. 2); (2) Coupling: The aldehydes react with hydrazide groups immobilized on a solid support to form covalent hydrazone bonds (FIG. 2). Non-glycosylated proteins are removed; (3) Proteolysis: The immobilized glycoproteins are proteolyzed on the solid support. The non-glycosylated peptides are removed by washing and can be optionally collected for further analysis, whereas the glycosylated peptides remain on the solid support; 4) Isotope labeling: The α amino groups of the immobilized glycopeptides are labeled with isotopically light (d0, contains no deuteriums) or heavy (d4, contains four deuteriums) forms of succinic anhydride after the ε-amino groups of lysine are converted to homoarginine (FIG. 3); (5) Release: Formerly N-linked glycopeptides are released from the solid-phase by PNGase F treatment; (6) Analysis: The isolated peptides are identified and quantified using microcapillary high performance liquid chromatography electrospray ionization tandem mass spectrometry (µLC-ESI-MS/MS) or µLC separation followed by matrix-assisted laser desorption/ionization (MALDI) MS/MS. The data are analyzed by a suite of software tools.

Proteins from a sample, for example, a complex biological sample, were changed to buffer containing 100 mM NaAc, 150 mM NaCl, pH 5.5 (coupling buffer). Sodium periodate solution at 15 mM was added to the samples. The cap was secured and the tube was covered with foil. The sample was rotated end-over-end for 1 hour at room temperature. The sodium periodate was removed from the samples using a desalting column (Econo-Pac 10 DG column). Hydrazide resin (Bio-Rad; Hercules Calif.) equilibrated in coupling buffer was added to the sample (1 ml gel/5 mg protein). The sample and resin were capped securely and rotated end-over-end for 10–24 hours at room temperature.

After the coupling reaction was complete, the resin was spun down at 1000×g for 10 min, and non-glycoproteins were washed away extensively by washing the resin 3 times with an equal volume of 8M urea/0.4M $NH_4HCO_3$. The proteins on the resin were denatured in 8M urea/0.4M NH$_4$HCO$_3$ at 55° C. for 30 min, followed by 3 washes with the urea solution. After the last wash and removal of the urea buffer, the resin was diluted 4 times with water. Trypsin was added at a concentration of 1 μg of trypsin/100 μg of protein and the bound proteins digested at 37° C. overnight. If desired, the peptides can be reduced by adding 8 mM TCEP (Pierce, Rockford Ill.) at room temperature for 30 min, and alkylated by adding 10 mM iodoacetamide at room temperature for 30 min. The trypsin released peptides were removed and collected for labeling with ICAT™ reagent or other tagging reagent, if desired. The resin was washed with an equal volume of 1.5 M NaCl 3 times, 80% acetonitrile (MeCN)/0.1% trifluoroacetic acid (TFA) 3 times, 100% methanol 3 times, and 0.1 M NH$_4$HCO$_3$ 6 times. N-linked glycopeptides were released from the resin by digestion with peptide-N-glycosidase F (PNGase F) overnight. The resin was spun and the supernatant was saved. O-linked glycopeptides can be released from the resin by using combination of neuraminidase/O-glycosidase. The resin was washed twice with 80% MeCN/0.1% TFA and combined with the supernatant. The peptides were dried and resuspended in 0.4% acetic acid for LC-MS/MS analysis.

Alternatively, the glycopeptides can be released from the resin chemically. The N-linked glycopeptide can be released by hydrazinolysis. Glycopeptides are dried in a desiccator over P$_2$O$_5$ and NaOH. The reaction is carried out in an air-tight screw-cap tube using anhydrous hydrazine. The reaction is carried out at 100° C. for about 10 hours using a dry heat block. The release of O-linked glycopeptide is carried out in 50 mM NaOH containing 1 M NaBH$_4$ at 55° C. for about 18 h.

For isotopic labeling of glycopeptides with succinic anhydride (FIG. 3), the glycopeptides on the beads were washed twice with 15% NH$_4$OH in water (pH>11). Methylisourea at 1 M in 15% NH$_4$OH (NH$_4$OH/H$_2$O=15/85 v/v) was added in 100 fold molar excess over amine groups and incubated at 55° C. for 10 minutes. Beads were then washed twice with water, twice with dimethylformamide (DMF)/pyridine/H$_2$O=50/10/40 (v/v/v) and resuspended in DMF/pyridine/H$_2$O=50/10/40 (v/v/v). Succinic anhydride solution was added to a final concentration of 2 mg/ml. The sample was incubated at room temperature for 1 hour, followed by washing three times with DMF, three times with water, and six times with 0.1M NH$_4$HCO$_3$. The peptides were released from the beads using PNGase F as describe above.

Alternatively, the glycopeptides can be labeled with other reagents at amine groups of glycopeptides while the peptides are still conjugated to the hydrazide beads. A list of chemicals that have been tested and proved to be able to label the amino groups is listed in FIG. 3. The structures of labeled peptide are listed at the right column. Once the glycopeptides were labeled isotopically, PNGase F was added to release the peptides from the solid support and analyzed by mass spectrometry.

For isotopic labeling of glycopeptides with Phe (see FIG. 9), 0.22 M of Boc-d0-Phe-OH (Nova Biochem) or Boc-d5-Phe-OH (CDN Isotopes) were dissolved in anhydrous, N,N-dimethyformamide. 1,3-Diisopropylcarbodiimide was added to a final concentration of 0.2 M. The reaction was carried out at room temperature for 2 hours. The glycopeptides on the beads were washed with 0.5 M NaHCO$_3$ three times and resuspended to a 50% slurry. The same volume of Boc-Phe-anhydride was added to the glycopeptides on the beads, and the beads were incubated at room temperature for 30 min. The beads were washed with 80% MeCN/0.1% TFA three times and dried. The Boc protection group was removed by incubating with TFA for 30 min at room temperature. The beads were washed with glycosidase buffer, followed by release of the labeled glycopeptides with glycosidases, as described above.

This example describes purification of glycopeptides and differential labeling with an isotope tag.

EXAMPLE II

Quantitative Glycopeptide Profiling in Human Blood Serum

This example describes profiling of glycoproteins in human blood serum.

To assess the potential of the glycopeptide capture method for serum protein profiling, the specificity and efficiency of conjugation was first determined. Human serum proteins were coupled to the hydrazide beads. Identical aliquots (1 μl) were removed from the sample before ("−beads") or after capture of glycoproteins to hydrazide resin ("+beads"). The samples were separated by 9% sodium dodecyl sulfate-polyacrylamide gel electrophoresis (SDS-PAGE) and stained with silver (total protein stain) or with a glycoprotein-staining reagent (FIG. 4).

Isolation of glycopolypeptides was performed essentially as described in Example I. For analysis of serum samples, 2.5 ml of human serum (200 mg total protein) were changed to buffer containing 100 mM NaAc, 150 mM NaCl, pH 5.5 using a desalting column (Bio-Rad). Sodium periodate solution at 15 mM was added to the samples. The cap was secured and the tube was covered with foil. The sample was rotated end-over-end for 1 hour at room temperature. The sodium periodate was removed from the samples using a desalting column. A 50 μl aliquot of the sample was taken before coupling the sample. To the sample was added 8 ml of coupling buffer equilibrated hydrazide resin (Bio-Rad). The sample and resin were capped securely and rotated end-over-end for 10–24 hours at room temperature. After the coupling reaction was complete, the resin was spun down at 1000×g for 10 min, and non-glycoproteins in the supernatant were removed. A 50 μl aliquot of the post conjugation sample was taken.

A portion of each of the aliquots taken before and after coupling (1 μl) was analyzed on a 9% sodium dodecyl sulfate-polyacrylamide gel electrophoresis (SDS-PAGE) gel and stained. For total proteins and glycoproteins, silver staining or GelCode Glycoprotein staining reagent, respectively, were used to determine the specificity and efficiency of glycoprotein isolation.

Figure 4:
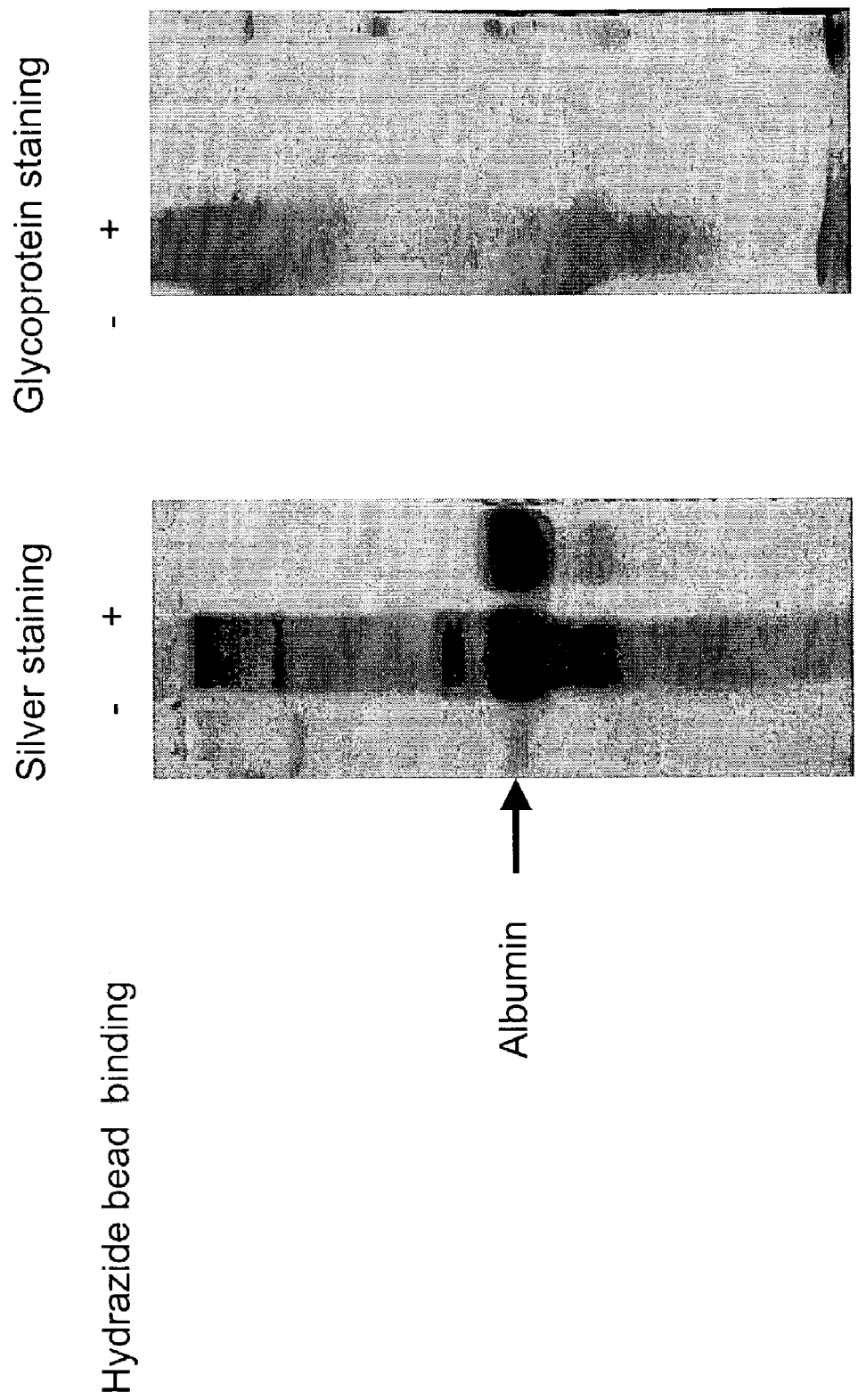
FIG. 4 shows total protein staining or glycoprotein staining of crude serum before (−) and after immobilization (+) of glycoproteins to hydrazide resin. Proteins were separated by SDS-PAGE and stained with silver (left) or Gel Code Blue glycoprotein staining reagent (right).

As shown in FIG. 4, the supernatant prior to addition to the beads (−) contains a number of proteins, many of which stain as glycoproteins (right panel, "−" lane). After addition and incubation with the beads, most of the glcyopolypeptides are removed (left and right panels, "+" lanes). These results show that the hydrazide beads efficiently bind the glcyopolypeptides from the serum sample. Note that the major serum protein, albumin, remained in the supernatant (left panel, "+" lane) and was not stained with the glycoprotein stain (right panel, "−" lane). Thus, albumin does not appear to be glycosylated. Since albumin is the major serum protein (>50%), the use of carbohydrate-specific binding provides a method to efficiently analyze low abundance, glycosylated polypeptides present in serum.

The following is apparent from the experiment shown in FIG. 4. First, as expected, the serum sample contains a considerable amount of glycosylated proteins (glycoprotein stain, "−beads" lane). Second, the majority of the protein bands were essentially depleted by the coupling reaction (silver stained bands "+/−beads" lanes). Third, as far as could be determined from the different staining intensities of the two staining methods used, glycosylated proteins were quantitatively depleted and bands containing glycosylated proteins were preferentially removed by the coupling reaction. Fourth, the major band representing serum albumin was not depleted by the coupling reaction and did not stain with the glycoprotein-staining reagent. Collectively, these results show that the hydrazide beads bind the oxidized glycoproteins from the serum sample efficiently and specifically. They also show that the major serum protein, albumin, predominantly remained in the supernatant (left panel, "+beads" lane) and was not stained with the glycoprotein stain (right panel, "+/−beads" lane). The use of carbohydrate-specific isolation of serum glycoproteins therefore provides a more economical, simpler and more reproducible method for serum albumin removal than the affinity depletion methods commonly used. Since the present method is also compatible with the immobilization of denatured proteins, it reduces the possibility that the selective removal of albumin also removes albumin-associated proteins.

Non-specific proteins bound to the resin were washed away extensively by washing the resin 3 times with an equal volume of 8M urea/0.4M $NH_4HCO_3$. The proteins on the resin were denatured in 8M urea/0.4M $NH_4HCO_3$ at 55° C. for 30 min, followed by 3 washes with the urea solution. After the last wash and removal of the urea buffer, the resin was diluted 4 times with water. Trypsin was added at a concentration of 1 μg of trypsin/100 μg of protein and digested at 37° C. overnight. The trypsin released peptides were removed by washing the resin with an equal volume of 1.5 M NaCl for 3 times, 80% MeCN/0.1% TFA for 3 times, 100% methanol for 3 times, and 0.1 M $NH_4HCO_3$ for 6 times. N-linked glycopeptides were released from the resin by digestion with PNGase F at 37° C. overnight. The resin was spun and the supernatant saved. The resin was washed twice with 80% MeCN/0.1% TFA and combined with the supernatant. The resin was saved for O-linked glycopeptide release later.

Figure 5:
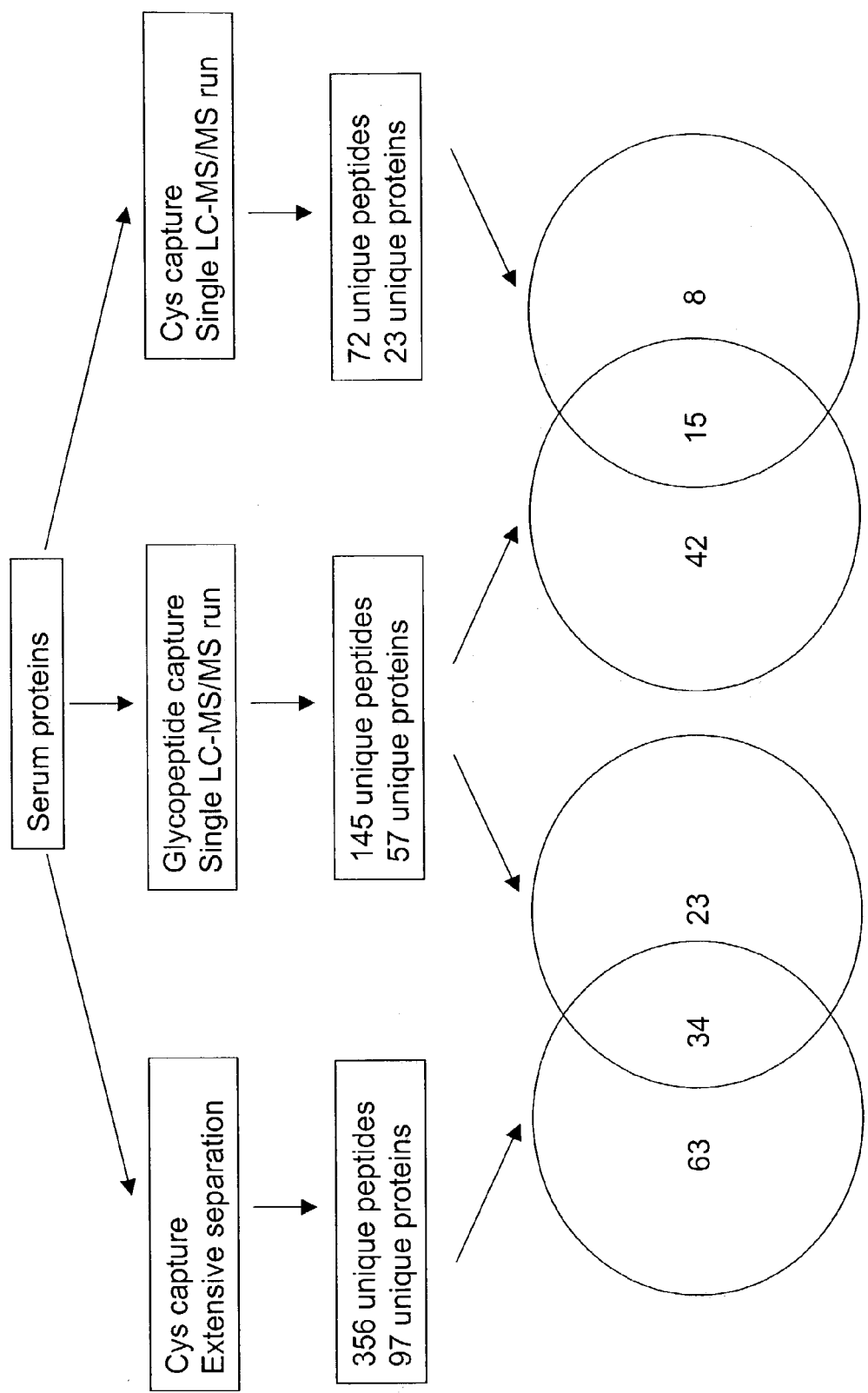
FIG. 5 shows an outline and comparison of the results of glycopeptide analysis of serum proteins observed with three methods: cysteine capture with extensive separation, glycopeptide capture and single liquid chromatography-mass spectrometry/mass spectrometry (LC-MS/MS), and cysteine capture and single LC-MS/MS.

The peptides were dried in 17 tubes, and one tube was resuspended 50 μl of 0.4% acetic acid. A 3 μl aliquot of the sample (from 9 μl of serum) was loaded on a capillary column for μLC-MS/MS analysis. CID spectra were searched against a human database using SEQUEST (Eng et al., *J. Am. Soc. Mass. Spectrom.* 5:976–989 (1994)) to identify the glycopeptides and glycoproteins (FIG. 5, middle panel).

To determine whether the reduced peptide sample complexity achieved by glycopeptide capture and release allowed the identification of more serum proteins compared to conventionally prepared control samples if comparable μLC-MS/MS protocols were applied, the number of glycopeptides and glycoproteins identified as described above was compared to the number of serum proteins identified from other methods using the same μLC-MS/MS protocols. Control samples were generated by selectively isolating cysteine-containing peptides using the ICAT reagent method (Gygi et al., *Nat. Biotechnol.* 17:994–999 (1999)). These were analyzed either using the same μLC-ESI-MS/MS method as for the analysis of the peptides isolated by the glycopeptide capture method (FIG. 5, right panel) or via extensive, three dimensional (cation exchange/biotin affinity/reverse phase liquid chromatography (RP-LC)) in which the peptide mixture was fractionated into 17 cation exchange fractions that were sequentially analyzed by μLC-ESI-MS/MS (FIG. 5, left panel; Han et al., *Nat. Biotechnol.* 19:946–951 (2001)).

Using a single μLC-ESI-MS/MS run requiring approximately two hours of mass spectrometer time, 145 unique peptides mapping to 57 unique serum proteins were identified with the glycopeptide capture method (2.5 peptides/protein). When comparable MS methods were applied for the analysis of cysteine tagged peptides, 72 unique peptides mapping to 23 unique proteins were identified, of which 15 were also identified via the glycopeptide capture method (FIG. 5, right panel). Using the extensive peptide separation protocol for the analysis of cysteine tagged peptides that required approximately 34 hours of mass spectrometer time, 356 unique peptides mapping to 97 serum proteins were identified. Of the 57 proteins isolated by the glycopeptide capture method and identified by single dimensional LC-MS/MS, 23 proteins were not seen by the extensive μLC-ESI-MS/MS based protocol of cysteine tagged peptides (FIG. 5, left panel). These data demonstrate the increased efficiency of serum analysis provided by the glycopeptide capture method.

As the current "gold standard method" for serum protein analysis is based on high resolution two-dimensional electrophoresis (2DE) and MS, the number of proteins identified by a single LC-MS/MS analysis of peptides isolated by the glycopeptide capture method was also related with the number of proteins that are annotated in the most up-to-date 2DE plasma protein map on SWISS-2DPAGE (us.expasy-.org/cgi-bin/get-ch2d-table.pl). The 2DE map identifies 58 unique proteins from 626 detected spots. Of these, 270 spots represent 8 different forms of immunoglobulin chains. Glycopeptide capture and single dimensional LC-MS/MS analysis identified 57 proteins, of which 7 are different immunoglobulin chains and 16 proteins are not included in SWISS-2DPAGE. Four major conclusions can be drawn that are relevant for assessing the potential of each method for serum protein profiling, even though, for reasons of sample and experimental variability, the data obtained from the three methods are not directly comparable. First, both the 2DE/MS based method and the cysteine tagging method are substantially limited by the presence of a number of high abundance proteins (that is, the "top down" problem in its extreme), which include the five major plasma proteins representing more than 80% of the total plasma protein mass (albumin, α-1-antitrypsin, β-2-macroglobulin, transferrin, and γ-globulins). When the cysteine tagged peptides were analyzed, the mass spectrometer spent over one third of the acquisition time on CID spectra of albumin (39% of peptides identified by the cysteine tagging method were from albumin). In contrast, the glycopeptide capture method selected against albumin with only 1% of peptides identified from albumin.

Second, proteins that were not identified by either of the traditional methods were readily identified following glycopeptide capture (FIG. 5). This attests to the potential of the glycopeptide capture method to achieve deeper serum protein coverage within a dramatically reduced data acquisition time. The limited diversity of the proteins analyzed by the traditional methods is further illustrated by the observation that of the 63 proteins that were only identified using cysteine reactive tags, 18 were different immunoglobulins. The glycopeptide capture method identified only peptides from the constant region of immunoglobulin and thus limited the number of immunoglobulin-derived peptides (7 immunoglobulin chains identified by the glycopeptide capture method, which were also identified by the cysteine tagging method).

Third, the glycopeptide capture method reduced the sample complexity; an average of 2.5 peptides per protein were detected. Fourth, the presence of the N-glycosylation sequence motif in the identified peptides provided further validation of specific isolation and increased the confidence in database searching results. Therefore, the reduction in sample complexity achieved by the glycopeptide capture method provides a substantial advance for the analysis of blood serum and other body fluids of similar protein composition.

Peptides isolated from 2.5 ml of serum using the glycopeptide capture method were further separated by cation exchange fractionation (Han et al. *Nat. Biotechnol.* 19:946–951 (2001)). Four of seventeen tubes containing peptides released from hydrazide resin as described above (equivalent of 600 μl serum) were separated by cation exchange chromatography to 38 fractions and resuspended in 20 μl of 0.4% acetic acid solution. A 5 μl aliquot of each fraction was loaded on a capillary column for μLC-MS/MS analysis. CID spectra were searched against a human database using SEQUEST (Eng et al., *J. Am. Soc. Mass. Spectrom.* 5:976–989 (1994)) to identify the glycopeptides and glycoproteins.

A large number of glycoproteins and their glycopeptides from a human serum sample were released with PNGase F. A total 1011 proteins identified had a protein probability score of at least 0.5. Based on the distribution of sensitivity and error rate at different protein and peptide probability score (Keller et al., *Anal. Chem.* 74:5383–5392 (2002)), there were 832 correctly identified proteins with a protein probability score of at least 0.5 (Table 2).

TABLE 2

Estimated sensitivity, error rates, number of correct and incorrect proteins with different protein probability score.

| Minimum probability | sensitivity | error rate | Number of correct proteins | Number of incorrect proteins |
|---|---|---|---|---|
| 1.00 | 0.264 | 0.000 | 288 | 0 |
| 0.99 | 0.291 | 0.001 | 318 | 0 |
| 0.98 | 0.315 | 0.002 | 344 | 1 |
| 0.97 | 0.331 | 0.004 | 362 | 1 |
| 0.96 | 0.344 | 0.005 | 375 | 2 |
| 0.95 | 0.356 | 0.007 | 388 | 3 |
| 0.90 | 0.417 | 0.019 | 455 | 9 |
| 0.80 | 0.522 | 0.049 | 570 | 29 |
| 0.70 | 0.607 | 0.084 | 662 | 61 |
| 0.60 | 0.684 | 0.126 | 746 | 108 |
| 0.50 | 0.762 | 0.177 | 832 | 179 |
| 0.40 | 0.835 | 0.235 | 911 | 279 |
| 0.30 | 0.907 | 0.304 | 990 | 432 |
| 0.20 | 1.000 | 0.406 | 1091 | 746 |

These results show that the glycopeptide capture method also removes albumin from the analysis of serum proteins, thereby allowing the analysis of less abundant serum proteins. The methods allowed the identification of a number of serum proteins that were not easily identified with other methods.

Blood serum is a complex body fluid that contains enormous information about body health. When blood circulates through the body, proteins secreted from cells, shredded from cell surface proteins, and released from dead cells from all tissues are deposited to the blood serum. Blood serum is also the most easily accessible specimen for diagnostic purpose. DNA array technology is not capable of analyzing serum samples since there is not a particular tissue sample from which to extract RNA. The analysis of plasma or serum proteins has also been a focus of proteomics. The two-dimensional electrophoretic technique has been used in the analysis of human plasma proteins since 1977 (Anderson and Anderson, *Proc. Natl. Acad. Sci. USA* 74:5421–5425 (1977)). To date, 289 plasma proteins have been identified using the 2DE method (Anderson and Anderson, *Mol. Cell. Proteomics* 1:845–687 (2002)). Recently, direct analysis of serum proteins with mass spectrometry was used to analyze proteins in human serum. In this analysis, abundant immunoglobulin proteins were first affinity depleted from serum sample. The resulting peptides were separated by strong cation exchange chromatography into distinct fractions prior to analysis. 490 serum proteins were identified by on-line reversed-phase microcapillary liquid chromatography coupled with ion trap mass spectrometry (Adkins et al., *Mol. Cell. Proteomics* 1947–1955 (2002)).

While the use of more extensive separation protocols for the formerly N-glycosylated peptides will increase the depth of serum protein coverage, tryptic peptides that are too short or too long to fall within the detection range of the mass spectrometer used will not be identified. This can be overcome, at least in part, by the use of proteases with cleavage specificities different from that of trypsin.

The increased number of serum proteins identified using the glycopeptide capture method compared to other proteomics methods so far shows that the glycopeptide method is an efficient method to analyze serum proteins and has the capacity to identify low abundance proteins as disease biomarkers in serum.

EXAMPLE III

Quantitative Profiling of Glycoproteins Secreted by Macrophages

This example describes the preparation of secreted protein sample from stimulated RAW 264.7 mouse monocyte/macrophage cell line.

Briefly, $10^9$ RAW cells were used. On day 1, cells were plated at a density of $2.5\times10^5$ cells/cm$^2$ with 10 nM phorbol 12-myristate-13-acetate (PMA). On day 2, the media was removed, and new media was added without PMA. On day 3, the cells were washed three times with serum-free media.

Lipopolysaccharide (LPS) was added as stimulant to the experimental cells with serum-free, PMA-free media. The cells were incubated at 37° C. for 4 hours. The supernatant was removed, and the cells were centrifuged at 3,000×g for 5 minutes to remove cells and large debris. The supernatant was centrifuged at 100,000×g for 1 hour to remove debris.

The supernatant was concentrated with an 80 mL Centricon concentrator, with 300 mL concentrated to <1 mL for each condition. The final concentration of proteins was at least 2 mg/mL.

One mg of proteins secreted from unstimulated and stimulated macrophages was changed to buffer containing 100 mM NaAc, 150 mM NaCl, pH 5.5, using a desalting column (Bio-Rad). Sodium periodate solution at 15 mM was added to the samples. The cap was secured and the tube covered with foil. The sample was rotated end-over-end for 1 hour at room temperature. Sodium periodate was removed from the samples using a desalting column. A 50 μl aliquot of the sample was taken before coupling the sample. To the sample was added 0.2 ml of coupling buffer equilibrated hydrazide resin (Bio-Rad). The resin and sample were capped securely and rotated end-over-end for 10–24 hours at room temperature. After the coupling reaction was complete, the resin was spun down at 1000×g for 10 min, and non-glycoproteins in the supernatant were removed. An aliquot of 50 µl of the post conjugation sample was taken. An aliquot of the samples before and after binding to the resin were analyzed on a 9% SDS-PAGE gel and stained for total proteins using silver staining reagent to determine the specificity and efficiency of glycoprotein isolation.

Non-specific proteins bound to the resin were washed away extensively by washing the resin 3 times with an equal volume of 8M urea/0.4M $NH_4HCO_3$. The proteins on the resin were denatured in 8M urea/0.4M $NH_4HCO_3$ at room temperature for 30 min, followed by 3 washes with the urea solution. After the last wash and removal of the urea buffer, the resin was diluted 4 times with water. Trypsin was added at a concentration of 1 µg of trypsin/100 µg of protein and digested at 37° C. overnight. The trypsin released peptides were removed by washing the resin with an equal volume of 1.5 M NaCl for 3 times, 80% MeCN/0.1% TFA for 3 times, 100% methanol for 3 times, 0.1 M $NH_4HCO_3$ for 6 times. N-linked glycopeptides were released from the resin by digest with N-glycosidase at 37° C. overnight. The resin was spin and the supernatant was saved. The resin was washed twice with 80% MeCN/0.1% TFA and combined with the supernatant. The resin was saved for O-linked glycopeptide release later.

The peptides were dried and resuspended in 50 µl of 0.4% acetic acid. 3 µl of sample was loaded on a capillary column for µLC-MS/MS analysis. CID spectra were searched against a mouse database using SEQUEST to identify the glycopeptides and glycoproteins.

Figure 6:
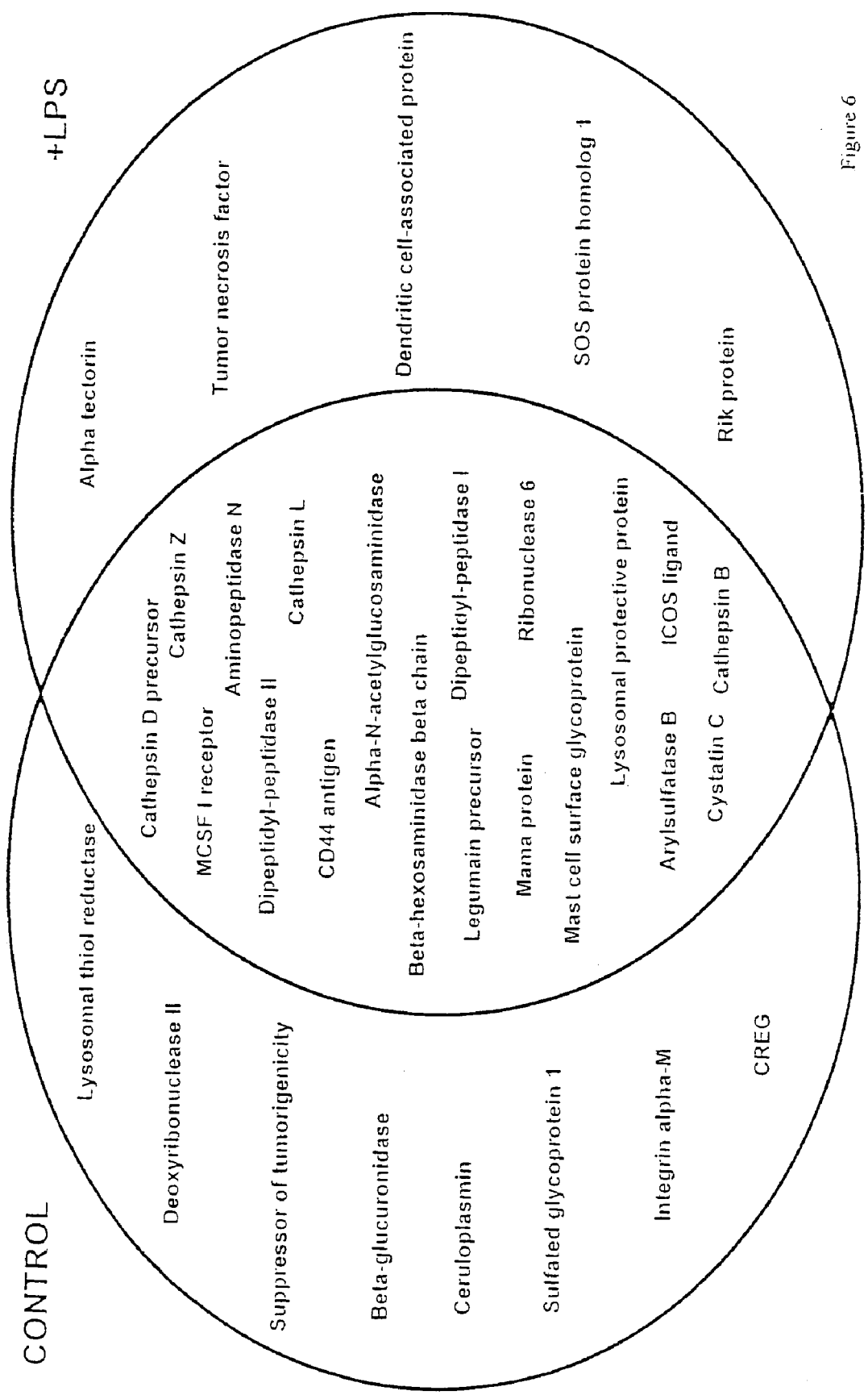
FIG. 6 shows identification of glycosylated proteins secreted from macrophages. Glycoproteins were identified from secreted proteins of untreated or LPS-treated RAW macrophage cells.

FIG. 6 shows glycoproteins identified from secreted proteins of untreated or LPS-treated RAW macrophage cells. A total of 32 proteins were identified. Nineteen secreted glycosylated proteins were identified in both untreated and treated cells. Eight proteins were identified in untreated cells, and five proteins were identified in treated cells. One of the known macrophage secreted proteins, tumor necrosis factor (TNF), was positively identified in media from RAW cells after LPS treatment. These results show that glycopolypeptides can be selectively isolated from a secreted proteins from cells in an efficient and specific manner.

For isotopic labeling of glycopeptides with succinic anhydride (FIG. 3), the dried peptides released from hydrazide resin were resuspended in DMF/pyridine/$H_2O$=50/10/40 (v/v/v). Succinic anhydride solution was added to a final concentration of 2 mg/ml. The sample was incubated at room temperature for 1 hour, followed by purification of peptides using C18 column. Labeled peptides are analyzed by mass spectrometry.

These results demonstrate that glycosylated secreted proteins can be isolated, identified and quantified.

EXAMPLE IV

Quantitative Glycopeptide Profiling of Cell Surface Proteins

This example describes profiling of cell surface glycoproteins.

To assess the potential of the glycopeptide capture method for the analysis of cell surface proteins, a crude membrane fraction from the LNCaP prostate cancer epithelial cell line was used to select and identify peptides containing N-linked glycosylation sites (Horoszewicz et al., Prog. Clin. Biol. Res. 37:115–132 (1980)). The released peptides isolated from 60 µg of a crude membrane fraction were analyzed by single dimension µLC-MS/MS and the data were processed.

Briefly, glycopolypeptides were isolated essentially as described in Example I. For the analysis of cell surface proteins, 4 mg of crude membrane fraction from the prostate cancer cell line, LNCaP (grown in RPMI medium supplemented with 10% fetal bovine serum), were dissolved in 1% NP40, 6 M urea, 100 mM Tris buffer, pH 8.3. The buffer was changed to coupling buffer containing 100 mM NaAc, 150 mM NaCl, pH 5.5, using a desalting column (Bio-Rad; Hercules Calif.). Sodium periodate solution was added at 15 mM to the samples. The cap was secured and the tube was covered with foil. The sample was rotated end-over-end for 1 hour at room temperature. The sodium periodate was removed from the samples using a desalting column. A 50 µl aliquot was taken before coupling the sample. To the sample was added 1 ml of coupling buffer equilibrated hydrazide resin (Bio-Rad). The resin and sample were capped securely and rotated end-over-end for 10–24 hours at room temperature.

After the coupling reaction was complete, the resin was spun down at 1000×g for 10 min, and non-glycoproteins were washed away extensively by washing the resin 3 times with an equal volume of 8M urea/0.4M $NH_4HCO_3$. The proteins on the resin were denatured in 8M urea/0.4M $NH_4HCO_3$ at 55° C. for 30 min, followed by 3 washes with the urea solution. After the last wash and removal of the urea buffer, the resin was diluted 4 times with water. Trypsin was added at a concentration of 1 µg of trypsin/100 µg of protein and digested at 37° C. overnight. The trypsin released peptides were removed by washing the resin with an equal volume of 1.5 M NaCl for 3 times, 80% MeCN/0.1% TFA for 3 times, 100% methanol for 3 times, and 0.1 M $NH_4HCO_3$ for 6 times. N-linked glycopeptides were released from the resin by digestion with N-glycosidase overnight. The resin was spun and the supernatant saved. The resin was washed twice with 80% MeCN/0.1% TFA and combined with the supernatant. The resin was saved for O-linked glycopeptide release later.

The peptides were dried in 4 tubes, and one tube was resuspended in 50 µl of 0.4% acetic acid. An aliguot of 3 µl of sample (from 60 µg original microsomal proteins) was loaded on a capillary column for µLC-MS/MS analysis. CID spectra were searched against a human database using SEQUEST (Eng et al., supra, 1994) to identify the glycopeptides and glycoproteins (see FIGS. 7 and 8 and Table 3).

Figure 7:
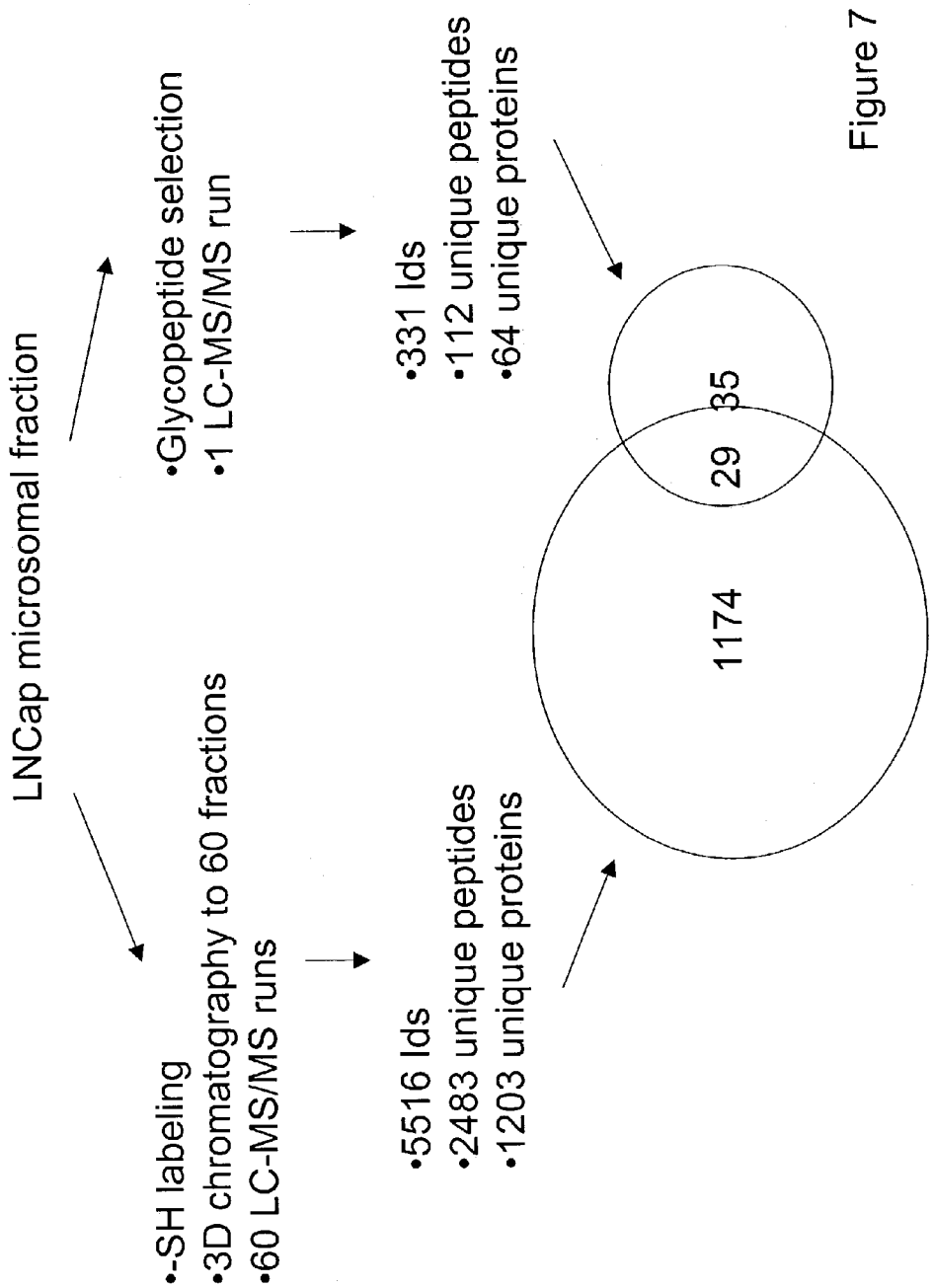
FIG. 7 shows comparison of protein/peptide identification from the microsomal fraction of the prostate cancer cell line LNCaP using an ICAT™ reagent or selective isolation of N-glycosylated peptides.

As shown in FIG. 7, 1203 unique proteins were identified from the microsomal fraction of LNCaP cells using ICAT reagent followed by intensive 3D chromatography to fractionate the peptide mixture. Using glycopeptide analysis, 64 unique proteins were identified. Of these, 35 glycopolypeptides were identified that were not identified from the total microsome fraction analysis. Table 3 shows glycoproteins and glycopeptides (SEQ ID NOS: 64–174) as well as the subcellular localization from a crude membrane fraction of the prostate cancer cell line LNCaP. The glycopeptides contain the conserved N-linked glycosylation motif (NXS/T)(indicated in bold).

Figure 8:
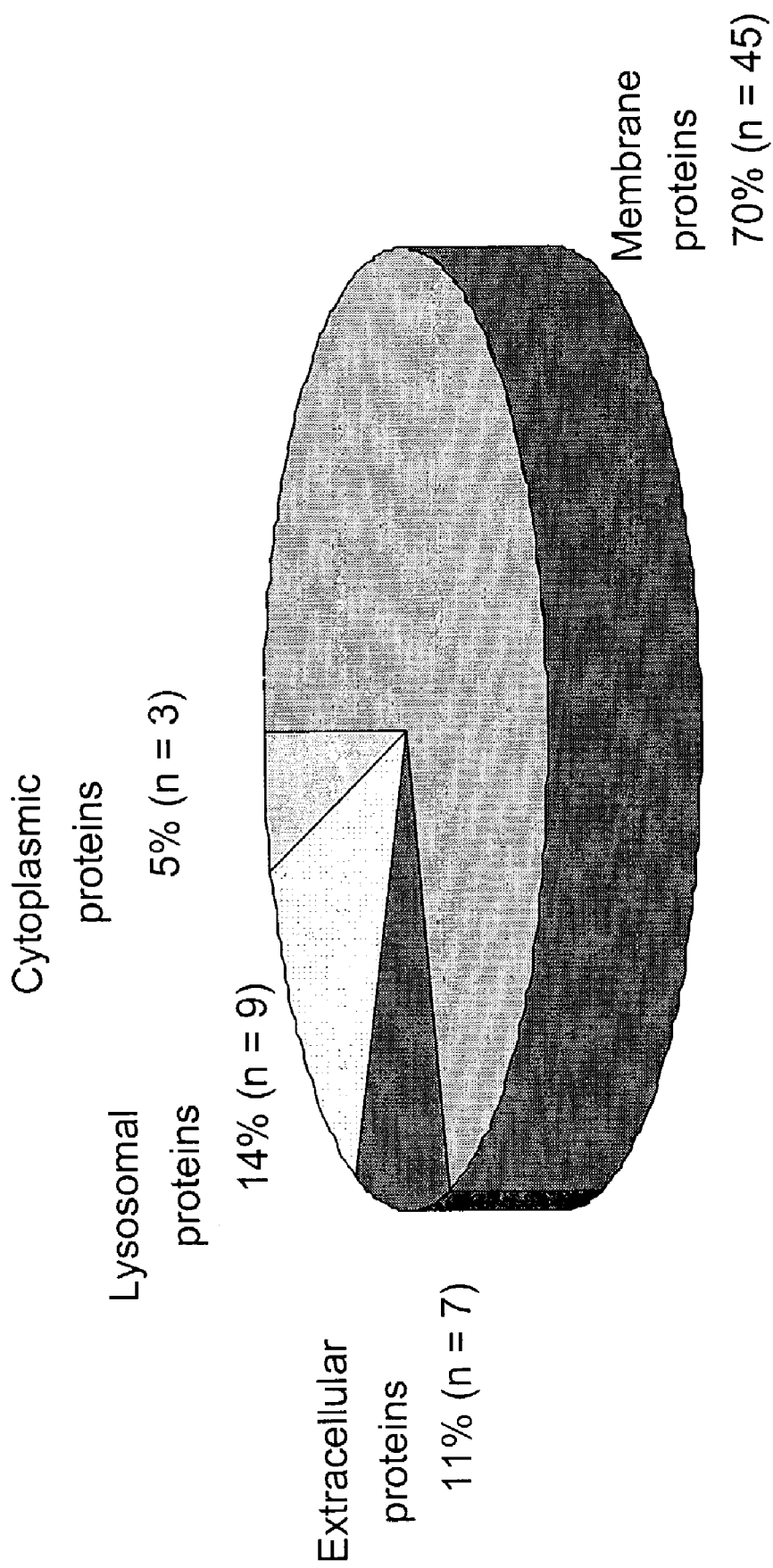
FIG. 8 shows subcellular location of glycoproteins identified from a crude microsomal fraction of LNCaP prostate epithelial cells.

The subcellular localization of the identified proteins was further analyzed using information from SWISS-PROT database (www.expasy.org/sprot/) or prediction tool, PSORT II (psort.ims.u-tokyo.ac.jp/). As shown in FIG. 8, of a total of 64 identified glycoproteins, 45 (70%) were bona fide or predicted transmembrane proteins. The non-transmembrane proteins were mostly designated as either extracellular (7 proteins, 11%) or lysosomal (9 proteins, 14%), two cellular compartments known to be enriched for glycoproteins. Only three proteins were assigned as cytoplasmic proteins (5%). Interestingly, two previously identified antigens, melanoma-associated antigen ME491 (CD63) and prostate-specific membrane antigen I (FOH1) were also identified in this experiment. These data indicate a marked improvement in selectivity for cell surface proteins over the analysis of crude microsomal fractions. Over 40% of the proteins identified were not membrane proteins in analysis of crude microsomal fraction (Han et al., *Nat. Biotechnol.* 19:946–951 (2001)). The data also indicate that proteins of high molecular weight and extreme pI, typically underrepresented in analyses performed using 2DE, are readily identified by this method. This is exemplified by the identification of basement membrane-specific heparan sulfate proteoglycan core protein (gene name SW: PGBM), a 470 kDa extracellular protein, and the acidic (pI=4.39) transmembrane protein signal sequence receptor α subunit (gene name SW: SSRA). These results indicate that the glycopeptide capture method is also effective for the selective analysis of proteins contained in the plasma membrane. Furthermore, proteins that were not detectable in analysis of a total microsome fraction were readily identified (see FIG. 7). These results indicate that the methods can be used to analyze glycopolypeptides not otherwise amenable to analysis of a total microsome protein fraction.

TABLE 3

Subcellular location of glycoproteins identified from LNCap cells

| Gene Name a | Protein Name | Subcellular Location b | Peptide Sequence c |
|---|---|---|---|
| GP:AB002313_1 | mRNA for KIAA0315 gene | Transmembrane, ER/Golgi/Plasma membrane a | K.LHVTLYNCSFGR.S |
| | | | R.SINVTGQGFSLIQR.F |
| | | | R.TEAGAFEYVPDPTFENFTGGVKK.Q |
| GP:AB033767_1 | BSCv mRNA | Transmembrane, ER | R.AGPNGTLFVADAYK.G |
| | | | K.LLLSSETPIEGKNMSFVNDLTVTQDGR.K |
| GP:AB045981_1 | hFKBP65 mRNA for FK506 binding protein | Extracellular | R.YHYNGSLMDGTLFDSSYSR.N |
| GP:AF089745_1 | FK506-binding protein (FKBP63) mRNA | Transmembrane, ER/Mitochondrial/Cytoplasmic | R.YHYNGTFLDGTLFDSSHNR.M |
| | | | R.YHYNGTLLDGTLFDSSYSR.N |
| GP:AF302102_1 | costimulatory molecule mRNA | Transmembrane, ER/Golgi/Plasma membrane | R.TALFPDLLAQGNASLR.L |
| GP:AJ245820_1 | mRNA for type I transmembrane receptor (psk-1 gene) | Transmembrane, ER/Golgi/Plasma membrane | R.LLANSSMLGEGQVLR.S |
| GP:AY032885_1 | | Transmembrane, ER/Golgi | K.QVALQTFGNQTIIPAGGAGYK.V |
| GP:BC001123_1 | Similar to gp25L2 protein | Transmembrane, ER/Golgi/Plasma membrane | R.FTFTSHTPGEHQICLHSNSTK.F |
| GP:BC001615_1 | Similar to hypothetical protein FLJ22625 | Transmembrane, Cytoplasmic/Vesicles of secretory system | K.IFIFNQTGIEAK.K |
| GP:BC001740_1 | | Extracellular | K.AVLVNNITTGER.L |
| | | | R.LQQDVLQFQKNQTNLER.K |
| GP:BC004423_1 | clone MGC:3530 IMAGE:2819660 | Transmembrane, Nuclear/mitochondrial | K.VVMDIPYELWNETSAEVADLK.K |
| GP:BC006786_1 | | Extracellular | K.LNITNIWVLDYFGGPK.I |
| GP:BC007443_1 | Similar to FK506 binding protein 9 | Transmembrane, ER/Mitochondrial/Cytoplasmic | K.YHNASLLDGTLLDSTWNLGK.T |
| GP:BC010078_1 | serine carboxypeptidase 1 | Transmembrane, Golgi/ER/Mitochondrial | R.KTTWLQAASLLFVDNPVGTGFSYVNGSGAYAK.D |
| GP:BC015678_1 | hypothetical protein GL012 | Mitochondrial/Cytoplasmic | R.CFATTYYLSEGGGLIFRNVTGEPNCRPPT R.G |
| GP:BC016467_1 | | Extracellular | R.YHYNGTLLDGTSFDTSYSK.G |
| GP:D85390_1 | mRNA for gp180-carboxypeptidase D-like enzyme | Transmembrane, ER | R.GILNATISVAEINHPVTTYK.T |
| | | | R.GLVMNYPHITNLTNLGQSTEYR.H |
| | | | R.LLNTTDVYLLPSLNPDGFER.A |
| PIR2:A47161 | Mac-2-binding glycoprotein | Extracellular | R.ALGFENATQALGR.A |
| PIR2:G01447 | | Transmembrane, Cytoplasmic/Vesicles of secretory system | R.VFPYISVMVNNGSLSYDHSK.D |
| PIR2:T42709 | hypothetical protein DKFZp586I0821 | Cytoplasmic | R.YHYNCSLLDGTQLFTSHDYGAPQEATLG ANK.V |
| PIR2:T47140 | hypothetical protein DKFZp761K1115.1 | Transmembrane, Vesicles of secretory system/nuclear | R.YSLNVTYNYPVHYFDGR.K |
| SW:4F2_HUMAN | 4f2 cell-surface antigen heavy chain (4f2hc) | Type II membrane protein b | R.DIENLKDASSFLAEWQNITK.G |
| | | | R.LLIAGTNSSDLQQILSLLESNK.D |
| | | | K.SLVTQYLNATGNR.W |
| SW:ASAH_HUMAN | acid ceramidase | Lysosomal | K.ILAPAYFILGGNQSGEGC*VITR.D |
| | | | R.TVLENSTSYEEAK.N |
| SW:ATNB_HUMAN | sodium/potassium-transporting atpase beta-1 chain | Type II membrane protein | R.FKLEWLGNCSGLNDETYGYK.E |
| | | | R.VLGFKPKPPKNESLETYPVMK.Y |
| | | | K.YLQPLLAVQFTNLTMDTEIR.I |
| SW:ATND_HUMAN | sodium/potassium-transporting atpase beta-3 chain | Type II membrane protein | K.LHVGYLQPLVAVQVSFAPNNTGK.E |
| | | | K.LHVGYLQPLVAVQVSFAPNNTGKEVTVE CK.I |

TABLE 3-continued

Subcellular location of glycoproteins identified from LNCap cells

| Gene Name a | Protein Name | Subcellular Location b | Peptide Sequence c |
|---|---|---|---|
| SW:BASI_HUMAN | basigin precursor (leukocyte activation antigen m6) | Type I membrane protein | K.ILLTCSLNDSATEVTGHR.W |
| | | | K.ITDSEDKALMNGSESR.F |
| SW:BGLR_HUMAN | beta-glucuronidase | Lysosomal | R.LLDAENKVVANGTGTQGQLK.V |
| | | | K.VVANGTGTQGQLK.V |
| SW:C166_HUMAN | cd166 antigen precursor (activated leukocyte-cell adhesion molecule) | Type I membrane protein | K.IIISPEENVTLTCTAENQLER.T |
| | | | K.LGDCISEDSYPDGNITWYR.N |
| | | | R.LNLSENYTLSISNAR.I |
| | | | R.TVNSLNVSAISIPEHDEADEISDENR.E |
| | | | R.TVNSLNVSAISIPEHDEADEISDENREK.V |
| SW:CATD_HUMAN | cathepsin d | Lysosomal | K.GSLSYLNVTR.K |
| | | | K.YYKGSLSYLNVTR.K |
| SW:CATL_HUMAN | cathepsin l | Lysosomal | K.YSVANDTGFVDIPK.Q |
| SW:CD63_HUMAN | cd63 antigen (melanoma-associated antigen me491) | Integral membrane protein; Lysosomal | R.QQMENYPKNNHTASILDR.M |
| SW:CLUS_HUMAN | clusterin | Extracellular | K.MLNTSSLLEQLNEQFNWVSR.L |
| SW:DRN2_HUMAN | deoxyribonuclease ii (lysosomal dnase ii) | Lysosomal | K.GHHVSQEPWNSSITLTSQAGAVFQSFAK.F |
| SW:DSG2_HUMAN | desmoglein 2 | Type I membrane protein | K.DTGELNVTSILDREETPFFLLTGYALDAR.G |
| SW:ENPL_HUMAN | endoplasmin | ER | K.HNNDTQHIWESDSNEFSVIADPR.G |
| | | | K.YLNFVKGVVDSDDLPLNVSR.E |
| SW:FOH1_HUMAN | folate hydrolase (prostate-specific membrane antigen 1) | Type II membrane protein | K.FLYNFTQIPHLAGTEQNFQLAK.Q |
| | | | R.GVAYINADSSIEGNYTLR.V |
| | | | K.TYSVSFDSLFSAVKNFTEIASK.F |
| | | | R.VDCTPLMYSLVHNLTK.E |
| | | | K.VPYNVGPGFTGNFSTQK.V |
| SW:GL6S_HUMAN | n-acetylglucosamine-6-sulfatase | transmembrane, Lysosomal | K.TPMTNSSIQFLDNAFR.K |
| | | | K.YYNYTLSINGK.A |
| SW:GLCM_HUMAN | glucosylceramidase | transmembrane, lysosomal | R.DLGPTLANSTHHNVR.L |
| | | | R.MELSMGPIQANHTGTGLLLTLQPEQK.F |
| | | | R.RMELSMGPIQANHTGTGLLLTLQPEQK.F |
| | | | R.TYTYADTPDDFQLHNFSLPEEDTK.L |
| SW:GLG1_HUMAN | golgi sialoglycoprotein mg-160 (cysteine-rich fibroblast growth factor receptor) | Type I membrane protein, Golgi | R.DIVGNLTELESEDIQIEALLMR.A |
| SW:HEXB_HUMAN | beta-hexosaminidase beta chain | Lysosomal | K.LDSFGPINPTLNTTYSFLTTFFK.E |
| SW:ITAV_HUMAN | integrin alpha-v | type I membrane protein | R.TAADTTGLQPILNQFTPANISR.Q |
| SW:LDLR_HUMAN | low-density lipoprotein receptor | type I membrane protein | R.LTGSDVNLLAENLLSPEDMVLFHNLTQPR.G |
| SW:LMG1_HUMAN | laminin gamma-1 chain | transmembrane, extracellular | K.LLNNLTSIK.I |
| SW:LMP1_HUMAN | lysosome-associated membrane glycoprotein 1 | Type I membrane protein | R.GHTLTLNFTR.N |
| | | | K.SGPKNMTFDLPSDATVVLNR.S |
| SW:LMP2_HUMAN | lysosome-associated membrane glycoprotein 2 | Type I membrane protein | K.IAVQFGPGFSWIANFTK.A |
| | | | K.WQMNFTVR.Y |
| SW:LU_HUMAN | lutheran blood group glycoprotein | Type I membrane protein | R.TQNFTLLVQGSPELK.T |
| SW:LYAG_HUMAN | lysosomal alpha-glucosidase | Lysosomal | R.GVFITNETGQPLIGK.V |
| SW:LYII_HUMAN | lysosome membrane protein ii | Type II membrane protein; lysosomal | K.CNMINGTDGDSFHPLITK.D |
| | | | R.TMVFPVMYLNESVHIDK.E |
| | | | R.TMVFPVMYLNESVHIDKETASR.L |
| SW:MA2B_HUMAN | lysosomal alpha-mannosidase | transmembrane, Lysosomal | R.LEHQFAVGEDSGRNLSAPVTLNLR.D |
| SW:MPRI_HUMAN | cation-independent mannose-6-phosphate receptor | Type I membrane protein; lysosomal | R.ATLITFLCDRDAGVGFPEYQEEDNSTYNFR.W |
| | | | R.HGNLYDLKPLGLNDTIVSAGEYTYYFR.V |
| | | | K.IKTNITLVCKPGDLESAPVLR.T |
| | | | R.SLLEFNTTVSCDQQGTNHR.V |
| | | | K.TNITLVCKPGDLESAPVLR.T |
| SW:NCM2_HUMAN | neural cell adhesion molecule 2 | Type I membrane protein | K.LVLPAKNTTNLK.T |
| | | | R.SHGVQTMVVLNNLEPNTTYEIR.V |
| SW:NEP_HUMAN | neprilysin | Type II membrane protein | R.SCINESAIDSR.G |
| | | | K.VMELEKEIANATAKPEDR.N |
| SW:NICA_HUMAN | nicastrin | Type I membrane protein | R.TSLELWMHTDPVSQKNESVR.N |
| SW:OXRP_HUMAN | 150 kda oxygen-regulated protein | transmembrane, ER | R.AEPPLNASASDQGEK.V |
| | | | K.LGNTISSLFGGGTTPDAKENGTDVQEEESPAEGSK.D |
| | | | R.LSALDNLLNHSSMFLK.G |
| | | | R.QTVHFQISSQLQFSPEEVLGMVLNYSR.S |
| | | | R.VFGSQNLTTVK.L |
| | | | K.VINETWAWK.N |
| | | | K.VINETWAWKNATLAEQAK.L |

TABLE 3-continued

Subcellular location of glycoproteins identified from LNCap cells

| Gene Name a | Protein Name | Subcellular Location b | Peptide Sequence c |
|---|---|---|---|
| SW:PGBM_HUMAN | basement membrane-specific heparan sulfate proteoglycan core protein | transmembrane, extracellular surface | R.LPQVSPADSGEYVCRVENGSGPK.E |
| SW:PPT_HUMAN | palmitoyl-protein thioesterase | Extracellular/vacuolar/mitochondrial | K.FLNDSIVDPVDSEWFGFYR.S |
| SW:PTK7_HUMAN | tyrosine-protein kinase-like 7 precursor (colon carcinoma kinase-4) | Type I membrane protein | R.MHIFQNGSLVIHDVAPEDSGR.Y |
| SW:SAP_HUMAN | P07602 h proactivator polypeptide | transmembrane, lysosomal | K.DVVTAAGDMLKDNATEEEILVYLEK.T R.NLEKNSTKQEILAALEK.G |
| SW:SE1L_HUMAN | sel-1 homolog precursor (suppressor of lin-12-like protein) | Integral membrane protein | K.GQTALGFLYASGLGVNSSQAK.A |
| SW:SPHM_HUMAN | n-sulphoglucosamine sulphohydrolase | Lysosomal | R.DAGVLNDTLVIFTSDNGIPFPSGR.T R.NALLLLADDGGFESGAYNNSAIATPHLD ALAR.R |
| SW:SSRA_HUMAN | signal sequence receptor alpha subunit | Type I membrane protein; ER | R.YPQDYQFYIQNFTALPLNTVVPPQR.Q |
| SW:SSRB_HUMAN | signal sequence receptor beta subunit | Type I membrane protein; ER | K.AGYFNFTSATITYLAQEDGPVVIGSTSAP GQGGILAQR.E R.IAPASNVSHTVVLRPLK.A |
| SW:TPP1_HUMAN | tripeptidyl-peptidase i | Lysosomal | K.FLSSSPHLPPSSYFNASGR.A |
| SWN:STM1_HUMAN | stromal interaction molecule 1 | Type I membrane protein cell surface | R.LAVTNTTMTGTVLK.M | a: Gene name is from human NCBI protein database (www.ncbi.nlm.nih.gov).
b: Subcellular locations in italic letter are predicted by PSORT, and b) in regular letter are from SWISSPROT
c: The consensus motif for N-linked glycosylation is highlighted.

The total number of proteins identified in this experiment is relatively small but consistent with the number of unique proteins identified from complex samples using LC-MS/MS without extensive separation. Because of the "top down" mode of precursor ion selection in the mass spectrometer, the most abundant proteins are preferentially identified. To identify a higher number of proteins, the sample would have to be more extensively fractionated prior to mass spectrometric analysis.

The method provides for quantitative profiling of glycoproteins or glycopeptides. The method allows the identification and quantification of glycoproteins containing N-linked carbohydrate in a complex sample and the determination of the site(s) of glycosylation. The selectivity of the method makes it ideally suited for the analysis of samples that are enriched in glycosylated proteins. These include cell membranes, body fluids and secreted proteins. Such samples are of great biological and clinical importance, in particular for the identification of diagnostic biomarkers and targets for immunotherapy or pharmacological intervention.

By combining this method with the cysteine tagging method using ICAT reagents (Gygi et al., supra, 1999), the occupancy of individual N-linked glycosylation sites and changes thereof can also be determined. This is of particular interest in studies in which changes of glycosylation occupancy are suspected, as exemplified by patients with Type I Congenital Disorders of glycosylation, in which the pathway of N-linked glycosylation is deficient (Aebi and Hennet, *Trends Cell Biol.* 11:136–141 (2001)).

The selectivity of the method also substantially reduces the complexity of the peptide mixture if complex protein samples are being analyzed because glycoproteins generally only contain a few glycosylation sites. The method is focused on the analysis of N-linked glycosylation sites. Analogous strategies can be devised to also analyze O-glycosylated peptides and in fact, a protein sample, once immobilized on a solid support, can be subjected to sequential N-linked and O-linked glycosylation peptide release, thus further increasing the resolution of the method and the information contents of the data obtained by it. Therefore, the method has wide applications in proteomics research and diagnostic applications.

These results show that membrane glycopolypeptides can be readily analyzed. Furthermore, glycopolypeptides that were not detectable in analysis of a total microsome fraction were readily identified (see FIG. 7). These results indicate that the methods can be used to analyze glycopolypeptides not otherwise amenable to analysis of a total microsome protein fraction. Also note that the method simplifies the analysis and focus on proteins located in plasma membrane and extracellular surface, which have therapeutic value for easy drug accessibility and antibody directed therapy.

EXAMPLE V

Quantitative Glycopeptide Profiling of Mouse Ascites Fluid

This example describes profiling of glycoproteins from mouse ascites fluid.

Glycopolypeptides were purified essentially as described in Example I. For the analysis of ascites fluid, 20 µl of mouse ascites fluid (600 µg total protein) were changed to buffer containing 100 mM NaAc, 150 mM NaCl, pH 5.5, using a desalting column (Bio-Rad). Sodium periodate solution was added at 15 mM to the samples. The cap was secured and the tube was covered with foil. The sample was rotated end-over-end for 1 hour at room temperature. The sodium periodate was removed from the samples using a desalting column. An aliquot of 20 µl of coupling buffer equilibrated hydrazide resin (Bio-Rad) was added to the sample. The sample and resin were capped securely and rotated end-over-end for 10–24 hours at room temperature.

After the coupling reaction was complete, the resin was spun down at 1000×g for 10 min, and non-glycoproteins were washed away extensively by washing the resin 3 times with an equal volume of 8M urea/0.4M $NH_4HCO_3$. The proteins on the resin were denatured in 8M urea/0.4M $NH_4HCO_3$ at 55° C. for 30 min, followed by 3 washes with the urea solution. After the last wash and removal of the urea buffer, the resin was diluted 4 times with water. Trypsin was added at a concentration of 1 µg of trypsin/100 µg of protein and digested at 37° C. overnight. The trypsin released peptides were removed by washing the resin with an equal volume of 1.5 M NaCl for 3 times, 80% MeCN/0.1% TFA for 3 times, 100% methanol for 3 times, and 0.5 M NaHCO$_3$ three times, and the resin was resuspended in 20 µl of 0.5 M NaHCO$_3$, pH 8.0.

For modification of peptides, 0.22 M of Boc-d0-Phe-OH (Nova Biochem) or Boc-d5-Phe-OH (CDN Isotopes) were dissolved in anhydrous N,N-Dimethyformamide. 1,3-Diisopropylcarbodiimide was added to a final concentration of 0.2 M, and the reaction was carried out at room temperature for 2 hours. A 10 µl aliquot of Boc-Phe-anhydride heavy or light forms was added to 10 µl of glycopeptides on the beads and incubated at room temperature for 30 min. The beads were washed with 80% MeCN/0.1% TFA three times, combined and dried. The Boc was removed by incubating with TFA for 30 min at room temperature. The beads were washed with glycosidase buffer, followed by release of the labeled glycopeptides with N-glycosidases at 37° C. overnight. N-glycopeptides were dried and resuspended in 20 µl of 0.4% of acetic acid. A 2 µl aliquot was analyzed by LC-MS/MS to determine the quantification of N-terminal labeling of glycopeptides by Phe (see FIGS. 9–12).

Mass spectrometry analysis of the peptide by LCQ and searching protein database by Sequest resulted in the identification of N-glycosylated peptides with the conserved N-glycosylation motif NXS/T. More than 50 glycoproteins were identified from 20 µl of mouse ascetic fluid, indicating the method is sensitive and useful for the identification of the glycoproteins from biological samples.

As shown in FIG. 9, isotopic labeling with Phe was performed with two equal amounts of mouse ascites fluid (1 µl), and the formerly N-linked glycopeptides were identified using MS/MS. FIG. 10 shows the list identified peptides after isotopically labeling with Phe. The corresponding collision-induced dissociation (CID) spectrum of one of the identified peptides, indicated by a circle, was shown in FIG. 11.

Figure 11:
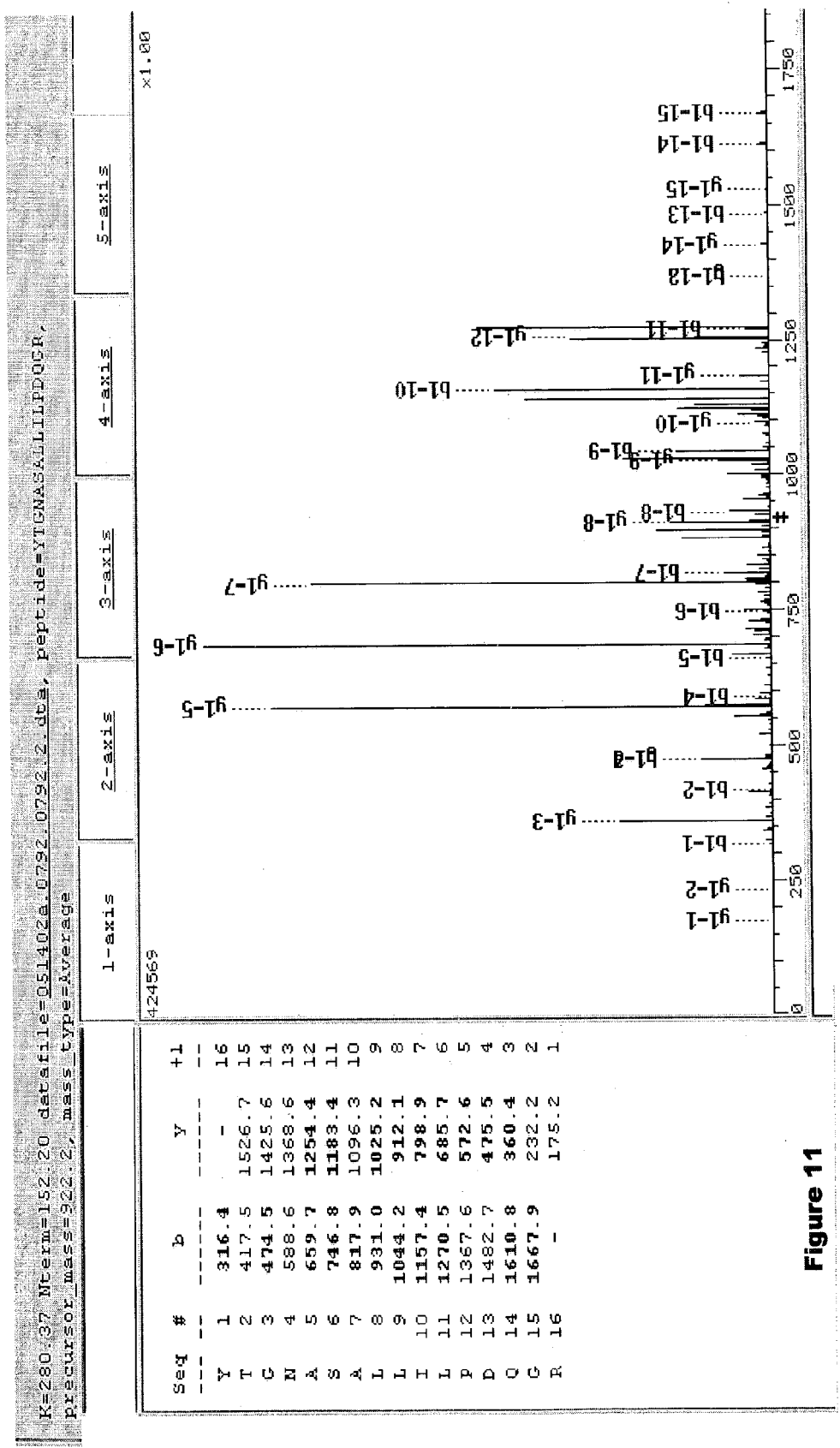
FIG. 11 shows collision-induced dissociation (CID) spectrum of one of the peptides (SEQ ID NO: 7) identified in FIG. 10 (circled).
Figure 12:
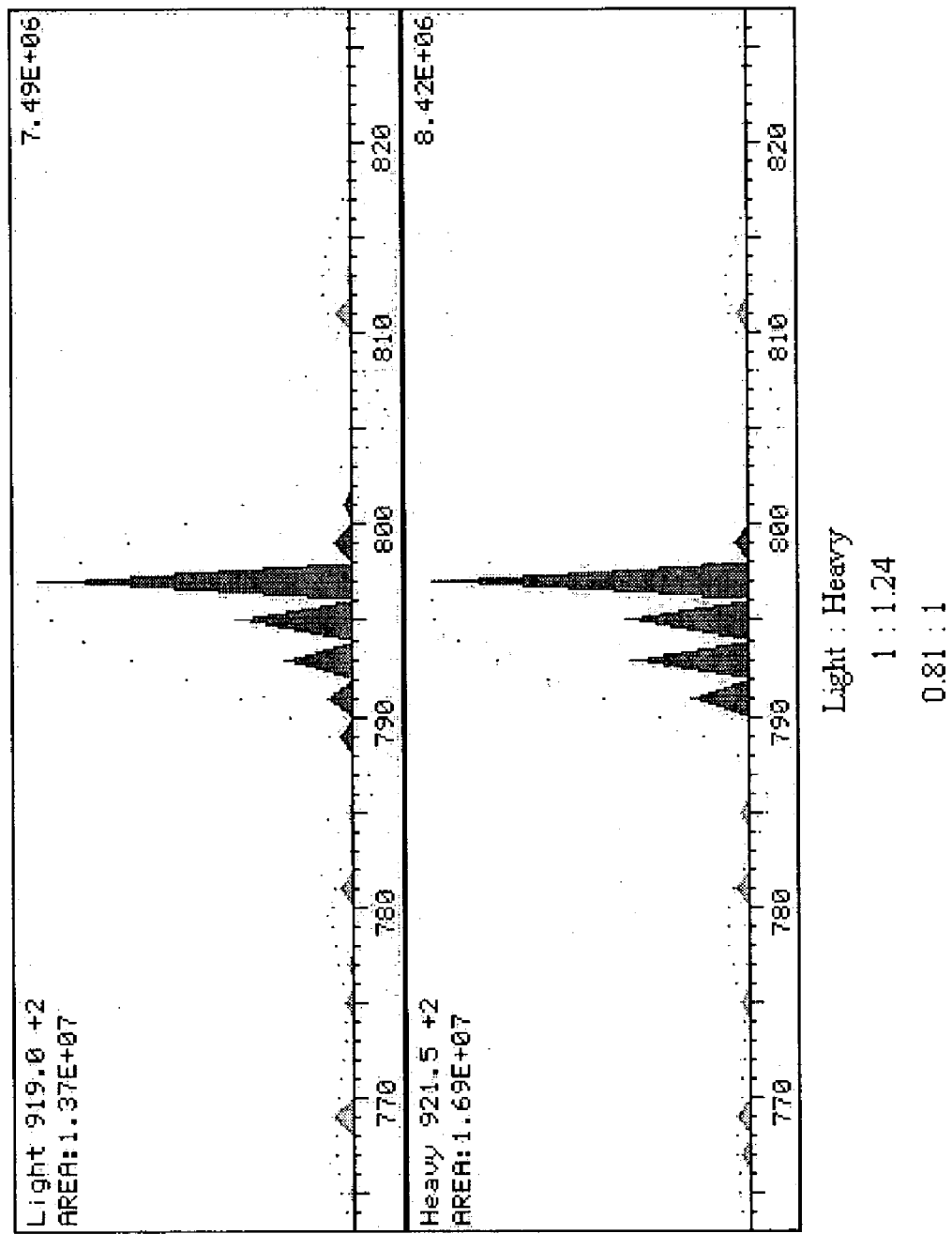
FIG. 12 shows reconstructed ion chromatograms for the peptide measured in FIG. 11. The ratio of the calculated peak area for the heavy and light form of the isotope tagged peptides was used to determine the relative peptide abundance in the original mixtures.

FIG. 12 shows reconstructed ion chromatograms for the peptide measured in FIG. 11. The ratio of the calculated peak area for the heavy and light form of the isotope tagged peptides was used to determine the relative peptide abundance in the original mixtures (light scan: mass 1837.0; heavy scan: mass 1842.0). The ratio (0.81:1) agreed reasonably well with the expected ratio of 1 to 1.

These results show that glycopolypeptides from complex body fluids can be analyzed, identified and quantified. Using isotope tags, two samples were compared and the relative amount of peptide in the original mixtures was determined, showing that the methods can be used quantitatively.

EXAMPLE VI

Quantitative Glycopeptide Analysis of Control Glycoproteins with a Known Ratio

This example describes quantitative analysis of glycoproteins from a pure glycoprotein mix with a known ratio and from two equal amounts of a human serum protein mix.

Two mixtures containing the same three glycoproteins at different amounts were prepared. The proteins were purchased from Calbiochem (San Diego, Calif.). The amount of each protein (µg) in mixture A and B were: α-1-antitrypsin (50, 10), α-2-hs-glycoprotein (10, 30), and α-1-antichymotrypsin (2, 2). Formerly N-linked glycosylated peptides from the two protein mixtures were purified and labeled as described in Example I.

Formerly N-glycosylated peptides were analyzed by µLC-ESI-MS/MS and identified. Table 4 shows the identified sequences (SEQ ID NOS: 175–179) and the observed d0/d4 peptide ratio for each identified peptide from two experiments. Of the four identified N-glycosylation sites, three have been described previously (Yoshioka et al., *J. Biol. Chem.* 261:1665–1676 (1986); Mills et al., *Proteomics* 1:778–786 (2001); Baumann et al., *J. Mol. Biol.* 218:595–606 (1991)), while N# in the sequence FN#LTETSEAEIHQSFQH (SEQ ID NO: 180) represents a glycosylation site in α-1-antichymotrypsin that has not been described previously. The abundance ratios calculated from the isotopic ratios agreed reasonably with the expected values. These results indicate that the method selectively isolates and quantifies N-linked glycopeptides from mixtures of glycoproteins.

TABLE 4

Quantitative analysis of glycoproteins in glycoprotein mixture

| Protein Name | Sequences of Identified Peptidesa | Glycosylation Sites | Observed Peptide Ratio (A/B) | Protein Ratio (A/B) | Expected Protein Ratio (A/B) |
|---|---|---|---|---|---|
| α-1-antichymotrypsin | K.FN#LTETSEAEIHQSFQH.L | Novel | 0.69; 0.91 | | |
| | F.LSLGAHN#TTLTEILK.G | Known | 1.63; 1.35 | 1.09 ± 0.39 | 1.00 |
| | L.SISTALAFLSLGAHN#TTLTEILK.G | Known | 0.88 | | |
| α-1-antitrypsin | R.QLAHQSN#STNIFF.S | Known | 6.47; 4.06 | 5.27 ± 1.70 | 5.00 |
| α-2-hs-glycoprotein | K.AALAAFNAQNN#GSNFQLEEISR.A | Known | 0.34; 0.51 | 0.42 ± 0.12 | 0.33 |

The specific capture of glycoproteins is based on the oxidation of hydroxyl groups on adjacent carbon atoms of carbohydrates to aldehydes by sodium periodate as previously described (Bobbitt, *Adv. Carbohydr. Chem.* 11, 1–41 (1956)). The aldehydes in turn covalently couple to amine- or hydrazide-containing molecules (Bayer et al., *Anal. Biochem.* 170:271–281 (1988)). Under the conditions used, the only expected side reaction of sodium periodate oxidation resulting in aldehydes is the oxidation of polypeptides containing a primary amine and a secondary hydroxyl group on adjacent carbon atoms, as exemplified by N-terminal serine residues (Geoghegan and Stroh, *Bioconjug. Chem.* 3:138–146 (1992)). This constellation is rare in proteins. The attachment of periodate oxidized proteins to hydrazide resin is therefore quite specific for glycoproteins containing N-linked and/or O-linked carbohydrates. Different types of oligosaccharides oxidize at different periodate concentrations and reaction conditions. The conditions used here (15 mM sodium periodate, room temperature for one hour) were chosen to assure oxidation of all types of oligosaccharides with hydroxy groups on adjacent carbon atoms. The enzyme catalyzed release of formerly N-glycosylated peptides by PNGase F provides specificity for N-linked glycopeptides and —N-linked glycosylation sites (Maley et al., *Anal. Biochem.* 180:195–204 (1989)). PNGase F will not, however, release N-linked oligosaccharides containing core fucosylation.

It was also determined whether the glycopeptide selection method could be used for detecting quantitative changes in the profiles of N-linked glycopeptides isolated from different samples of human serum. In a proof-of-principle experiment, glycopeptides from two equal amounts of human serum (1 mg total protein) were isotopically labeled with either light (d0) or heavy (d4) forms of succinic anhydride at N-termini after C-terminal lysine residues were converted to homoarginines as described in Example I. The lysine-to-homoarginine conversion facilitated detection by MALDI quadrupole time-of-flight (MALDI-QqTOF) mass spectrometry and the stable isotope tag was incorporated for quantification. After labeling, the beads containing the two samples were combined, and the formerly N-linked glycopeptides were released. A fraction of the sample, equivalent to 1.25 µl of serum, was fractionated to 29 spots on a MALDI plate by RP-LC and analyzed by MALDI-QqTOF MS and MS/MS. The experiment was repeated and analyzed by ESI-QqTOF MS, and the results were comparable to those identified by MALDI-QqTOF MS. Table 5 lists the identified peptides (SEQ ID NOS: 181–197), the proteins from which they originated and their observed quantitative ratio from two experiments. Generally, the observed ratios were close to the expected ratio of 1. The differences between the observed and expected ratio ranged between 0%–29% with a mean of 8%. This indicates that the glycopeptide capture method allows reasonable quantification if combined with stable isotope tagging.

Figure 13:
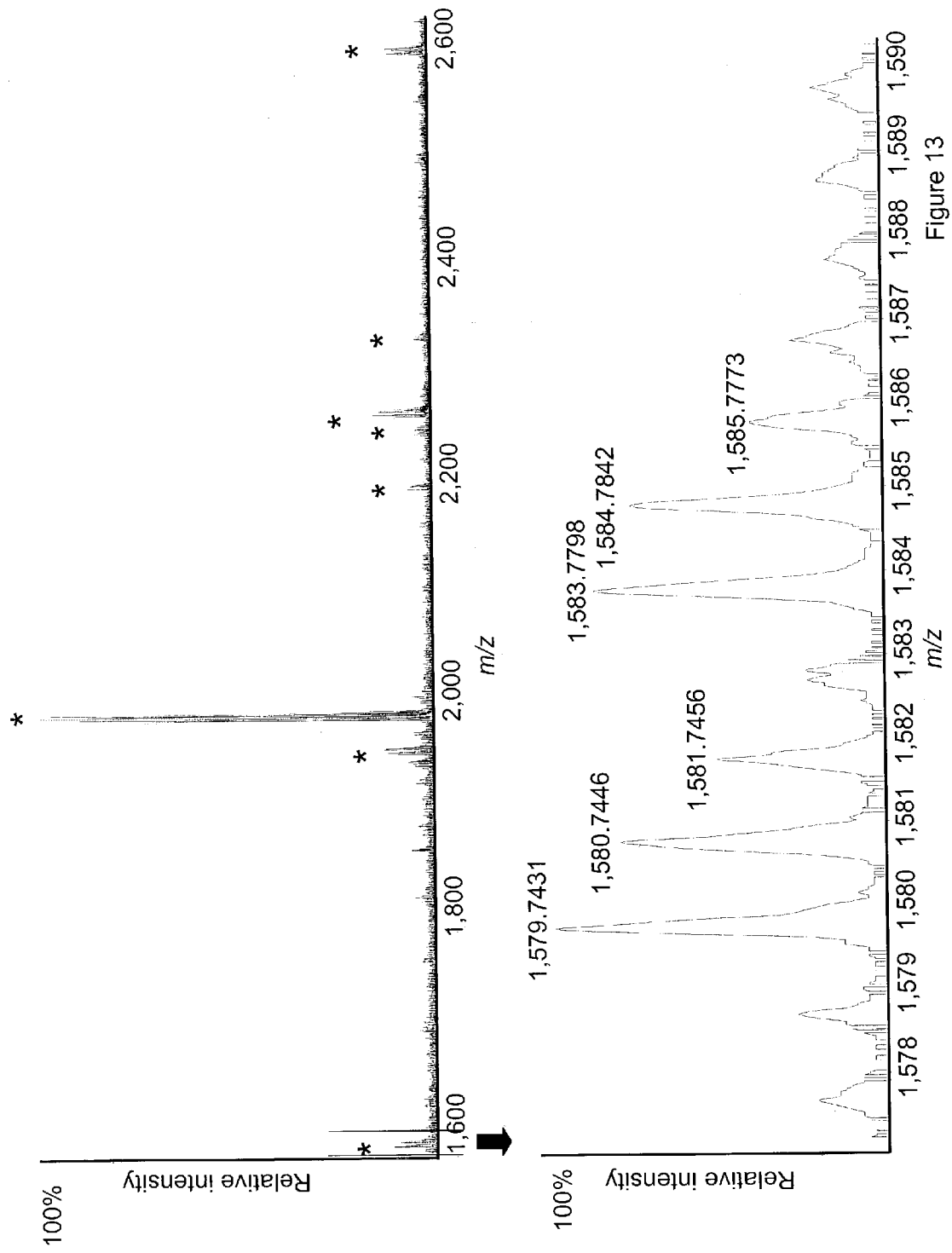
FIG. 13 shows the quantification for a single peptide pair. A single scan of the mass spectrometer at spot 28 from a MALDI plate in MS mode identified eight paired signals with a mass difference of four units (indicated with *).

The quantification is further illustrated for a single peptide pair in FIG. 13. A single scan of the mass spectrometer at spot 28 in MS mode identified eight paired signals with a mass difference of four units (indicated with *, FIG. 13). An expansion of the mass range between m/z=1577 and m/z=1590 resolved the natural isotopic distribution of a peptide pair with monoisotopic peaks at 1579.74 and 1583.78, in which the signals had a quantitative ratio of 1.11.

These results indicate that the method selectively isolates and quantifies N-linked glycopeptides from mixtures of glycoproteins.

EXAMPLE VII

Identification of N-linked Glycosylation Sites and Consensus Motif for N-linked Glycosylation This example describes the identification of asparagine residues that are occupied by N-linked carbohydrates in the native protein and determination of consensus motif from the alignment of identified N-linked glycosylation sites.

Glycoproteins were conjugated to hydrazide resin and released from the solid support by PNGase F as described in Example I. PNGase F catalyzed cleavage of oligosaccharides from glycoproteins deaminates the linker asparagine to aspartic acid causing a mass shift of one mass unit. The single mass unit differences between asparagine and aspartic acid were detected by mass spectrometers and identify the asparagine residues to which the oligosaccharides were attached.

The one mass unit difference caused by conversion of asparagine to aspartic acid after cleavage of oligosaccharides from glycoproteins was specified in Sequest search parameter during database search of the MS/MS spectra. The acquired MS/MS spectra were searched against the human protein database from NCBI. For MS/MS spectra acquired by MALDI QqTOF (MDS SCIEX; Concord, Ontario Calif.), the mass window for the singly-charged ion of each peptide being searched was given a tolerance of 0.08 Da between the measured monoisotopic mass and the calculated monoisotopic mass, and the b, y, and z ion series of the database peptides were included in the Sequest analysis. For MS/MS spectra acquired by a Finnigan LCQ ion trap mass spectrometer, the mass window for each peptide being searched was given a tolerance of 3 Da between the measured average mass and the calculated average mass, and the

TABLE 5

Quantitative analysis of glycoproteins from two identical serum samples

| Gene Name a | Protein Names | Sequences of identified peptides b | Observed Ratio (Mean ± SD) | Expected Ratio | % Error |
|---|---|---|---|---|---|
| GP:AF384856_1 | peptidoglycan recognition protein L | R.GFGVAIVGN#YTAALPTEAALR.T | 0.95 ± 0.02 | 1 | 5 |
| GP:M36501_1 | α-2-macroglobulin | Y.VLDYLN#ETQQLTPEIK.S | 0.93 ± 0.03 | 1 | 7 |
| SW:A1AG_HUMAN | α-1-acid glycoprotein 1 | N.LVPVPITN#ATLDQITGK.W | 1.05 ± 0.11 | 1 | 5 |
| SW:A1AT_HUMAN | α-1-antitrypsin | K.YLGN#ATAIFFLPDEGK.L | 1.10 ± 0.11 | 1 | 10 |
| SW:A1AT_HUMAN | α-1-antitrypsin | R.QLAHQSN#STNIFF.S | 1.00 ± 0.01 | 1 | 0 |
| SW:AACT_HUMAN | α-1-antichymotrypsin | K.YTGN#ASALFILPDQDK.M | 1.05 ± 0.03 | 1 | 5 |
| SW:CO3_HUMAN | complement c3 | N.HMGN#VTFTIPANR.E | 0.91 ± 0.02 | 1 | 9 |
| SW:CO4_HUMAN | complement c4 | R.FSDGLESN#SSTQFEVK.K | 0.93 ± 0.07 | 1 | 7 |
| SW:HPT1_HUMAN | haptoglobin-1 | K.VVLHPN#YSQVDIGLIK.L | 1.04 ± 0.03 | 1 | 4 |
| SW:HPT1_HUMAN | haptoglobin-1 | K.NLFLN#HSEN#ATAK.D | 1.29 ± 0.33 | 1 | 29 |
| SW:IC1_HUMAN | plasma protease c1 inhibitor | R.VLSN#NSDANLELINTWVAK.N | 0.90 ± 0.03 | 1 | 10 |
| SW:ITH1_HUMAN | inter-α-trypsin inhibitor heavy chain h1 | H.FFAPQN#LTNMNK.N | 0.96 ± 0.01 | 1 | 4 |
| SW:ITH2_HUMAN | inter-α-trypsin inhibitor heavy chain h2 | K.GAFISN#FSMTVDGK.T | 1.08 ± 0.12 | 1 | 8 |
| SW:ITH4_HUMAN | inter-α-trypsin inhibitor heavy chain h4 | N.QLVDALTTWQN#K.T | 1.01 ± 0.13 | 1 | 1 |
| SW:KAIN_HUMAN | Kallistatin | K.FLN#DTMAVYEAK.L | 1.24 ± 0.30 | 1 | 24 |
| SW:KAL_HUMAN | plasma kallikrein | R.IYSGILN#LSDITK.D | 1.06 ± 0.08 | 1 | 6 |
| SW:KNG_HUMAN | Kininogen | K.LNAENN#ATFYFK.I | 0.94 ± 0.10 | 1 | 6 | a: Gene name is from human NCBI protein database (www.ncbi.nlm.nih.gov).
b: The consensus motif for N-linked glycosylation is highlighted and the asparagine residues to which carbohydate linked are N#.

b and y ion series were included in the Sequest analysis. The sequence database was set to expect the following possible modifications to certain residues: carboxymethylated cysteines, oxidized methionines and an enzyme catalyzed conversion of Asn to Asp at the site of carbohydrate attachment. There were no other constraints included in the Sequest search.

Figure 14:
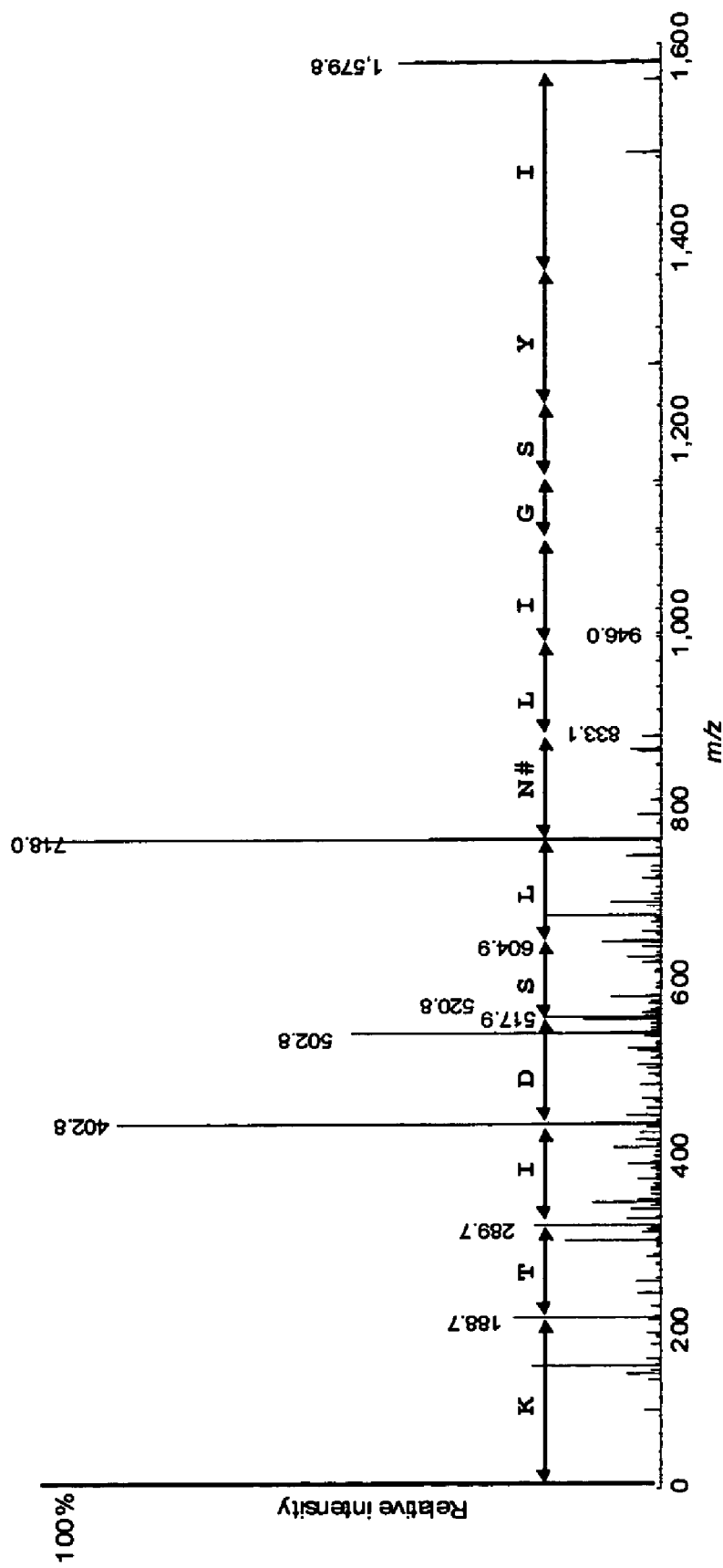
FIG. 14 shows analysis of a precursor ion by MS/MS. Sequence database searching of the resulting spectrum identified the peptide sequence as IYSGILN#LSDITK (SEQ ID NO:210) from human plasma kallikrein, a serum protease. N# indicates the modified asparagine in the peptide sequence.

The precursor ion with m/z =1579.74 identified in Example VI was further analyzed by MS/MS and sequence database searching of the resulting spectrum, and it was identified with peptide sequence IYSGILN#LSDITK (SEQ ID NO:210) from human plasma kallikrein, a serum protease (FIG. 14). N# indicates the modified asparagine in the peptide sequence. The series of y ions from this peptide confirmed the match and indicates that the single mass unit difference between asparagine and aspartic acid can be easily detected by MALDI QqTOF mass spectrometry, thus confirming the precise glycosylation site within the peptide as N7.

Figure 15:
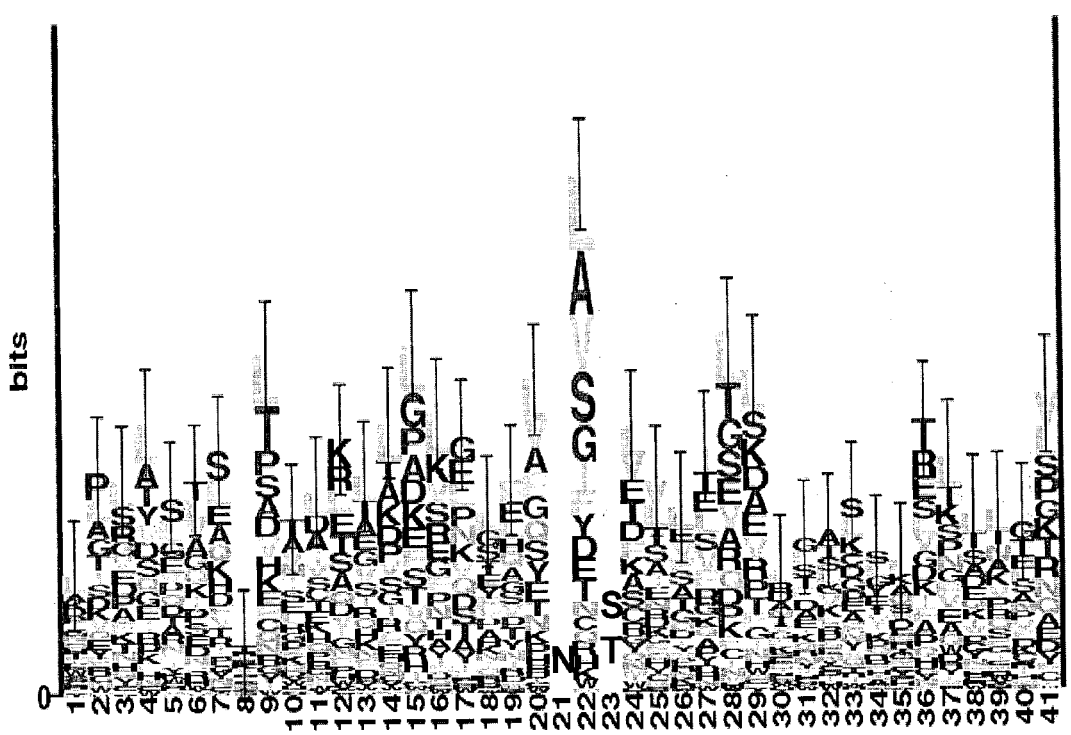
FIG. 15 shows the patterns of aligned sequences. For each position in the aligned sequence, the height of each letter is proportional to its frequency, and the most common one is on top. There was high preference of N at position 21 (removed to show the detail of other positions). The preference of N was followed by S or T at position 23 (removed to show residues in other positions).

The peptides identified with N to D conversion were aligned using Sequence Logos (Schneider and Stephens, *Nucleic Acids Res.* 18:6097–6100 (1990)). FIG. 15 shows the patterns of aligned sequences. For each position in the aligned sequence, the height of each letter is proportional to its frequency, and the most common one is on top. As expected, there was high preference of N at position 21 in FIG. 15 (removed to show the detail of other positions). The preference of N was followed by S or T at position 23 (removed to show residues in other positions). This is a known consensus N-linked glycosylation motif. In addition, the preference of L, V, A, S, G at positions 9, 15, 20, 22, 24, 28, 29 was identified.

The identified glycopeptides were used to build a glycopeptide database. When searching a human database for potential N-linked glycosylation motifs with the previously defined NXS/T sequence, sixty percent of human proteins contain the consensus N-linked glycosylation motif. The alignment of identified N-linked glycopeptides by the glycopeptide capture method described here refined and extended the consensus N-linked glycosylation motif. The refined motif is used to generate an algorithm to search the entire database for possible N-linked glycosylation sites. This increases the database searching constraints and reduces the propensity of false identifications. Protein topology of known proteins or predicted protein topology from prediction programs such as PSORT II can be used to further increase the confidence of the predicted N-linked gycosylation motif since it is known that N-linked glycosylation occurs on extracellular domains and on the protein surface.

The increased prediction power for N-linked glycosylation sites can be used to search the candidate genes specific to ovarian cancer from microarray data of normal and ovarian cancer samples. The predicted N-linked glycosylation peptides are synthesized with the incorporation of stable isotope amino acids. 500 fmole of synthetic peptides are mixed with peptides purified from normal and ovarian cancer serum using the glycopeptide capture method described in Example I. The relative abundance of candidate peptides in normal and cancer patients are quantified with high accuracy and sensitivity. Since the peptide mass and MS/MS spectra of each synthetic peptide are known, the mass spectrometer can be set to run in single reaction monitor mode (SRM) with increased sensitivity and accuracy of quantification.

This example describes an exemplary method to identify glycosylation sites.

EXAMPLE VIII

Quantitative Profiling of Glycoproteins in Extracellular Matrix of Prostate Cancer Prostate cancer is the most common cancer in men in the Western world, and the second leading cause of cancer mortality. The prostate is remarkably prone to developing cancer, and because little is known about the cause, no preventive measures can be formulated. With the use of prostate-specific antigen (PSA)-based screening, 80% of prostate cancer can be detected at a stage where it can be treated by local therapies. However, the rate of treatment failure as indicated by rising PSA levels can range from 10% to 40%. Apparently the escape of cancer cells from the prostate is an early event, and many patients test positive for these cells in their blood and bone marrow. A challenge in the diagnosis and treatment of prostate cancer is to develop better markers for cancer diagnosis to detect the disease at an early, more curable stage; to molecularly define prostate cancer progression for more accurate prognosis; and to identify cancer cell surface specific antigens as therapeutic targets.

Tumor and benign tissue samples from the peripheral zone of the prostate of the same patients were handled under sterile conditions. Tissue specimens were minced and digested with collagenase in RPMI-1640 medium supplemented with $10^{-8}$ M dihydrotestosterone (Liu et al., *Prostate* 40:192–199 (1999)). The digestion medium was saved, and glycoproteins were isolated as described in Example I.

The extracellular matrix protein species from patient-matched normal and cancer samples were processed by the glycopeptide capture method as described in Example I. The peptides released from the hydrazide resin were resuspended in 20 µl of 0.4% acetic acid. A 5 µl aliquot of sample was analyzed by µLC-MS/MS analysis, and the CID spectra were searched against the Human NCI database using Sequest.

Figure 16:
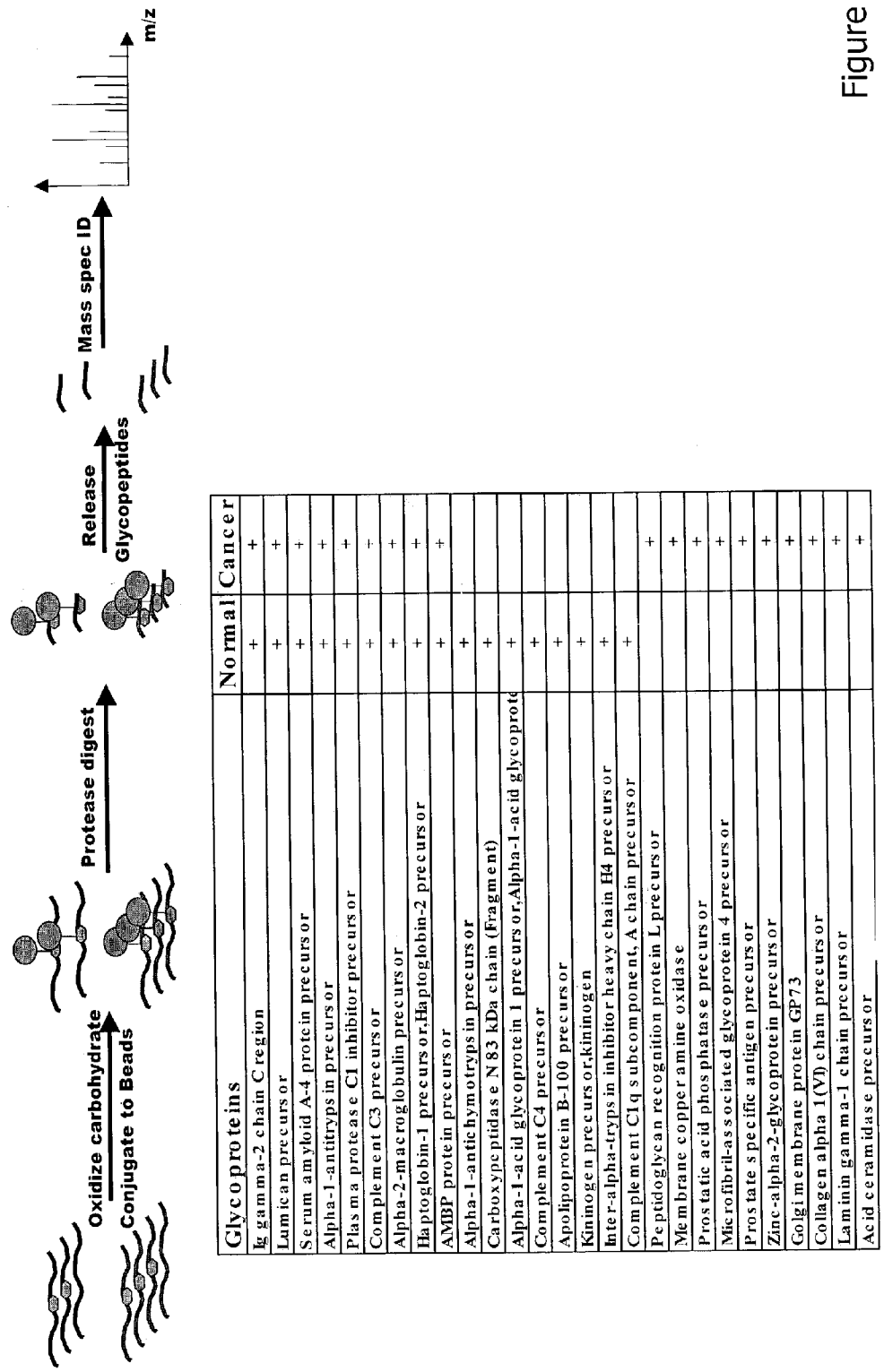
FIG. 16 shows proteins identified from extracellular matrix of normal and prostate cancer tissues.

FIG. 16 shows the proteins identified from normal and cancer tissues. Two cancer specific proteins, prostate-specific antigen (PSA) and prostatic acid phosphatase (PAP), were readily detected in cancer tissues.

The formerly N-linked glycosylated peptides are labeled with light and heavy succinic anhydride as described in Example I, and peptides from normal (labeled with light succinic anhydride) and cancer (labeled with heavy succinic anhydride) samples are combined and analyzed by LC-MS/MS. The CID spectra are searched against a human database, and the identified proteins are quantified using stable isotope quantification software tools such as ASASratio, and Express (Han et al., *Nat. Biotechnol.* 19:946–951 (2001)).

Since the concentration of specific proteins at the cancer tissue is much higher than that in blood serum, the cancer specific surface proteins are easily detected. The identified proteins can serve as cancer cell surface specific therapeutic targets. To determine the existence of cancer specific proteins in serum of prostate cancer patients, synthetic peptides are mixed with glycopeptides isolated from serum and analyzed by mass spectrometry. SRM mode analysis is used in the analysis and it increases the specificity and sensitivity of detecting the peptides in patient serum for early detection markers.

This example describes the identification of markers from cancer samples as potential diagnostic markers and/or therapeutic targets.

EXAMPLE IX

Quantitative Profiling of Glycopeptides and Identification of Biomarkers from Mice with Skin Cancer This example describes identification of biomarkers associated with skin cancer.

Mass spectrometry has recently been used as a platform for protein-based biomarker profiling (Petricoin et al. *Lancet* 359:572–577 (2002)). It has been shown that pathological changes of tissues and organs are reflected in serum protein changes while blood circulates in the body. The reduced sample complexity and enriched biological information from the glycopeptide capture method provides advantages for the systematic investigation of serum protein expression patterns of thousands of proteins in serum.

Figure 17:
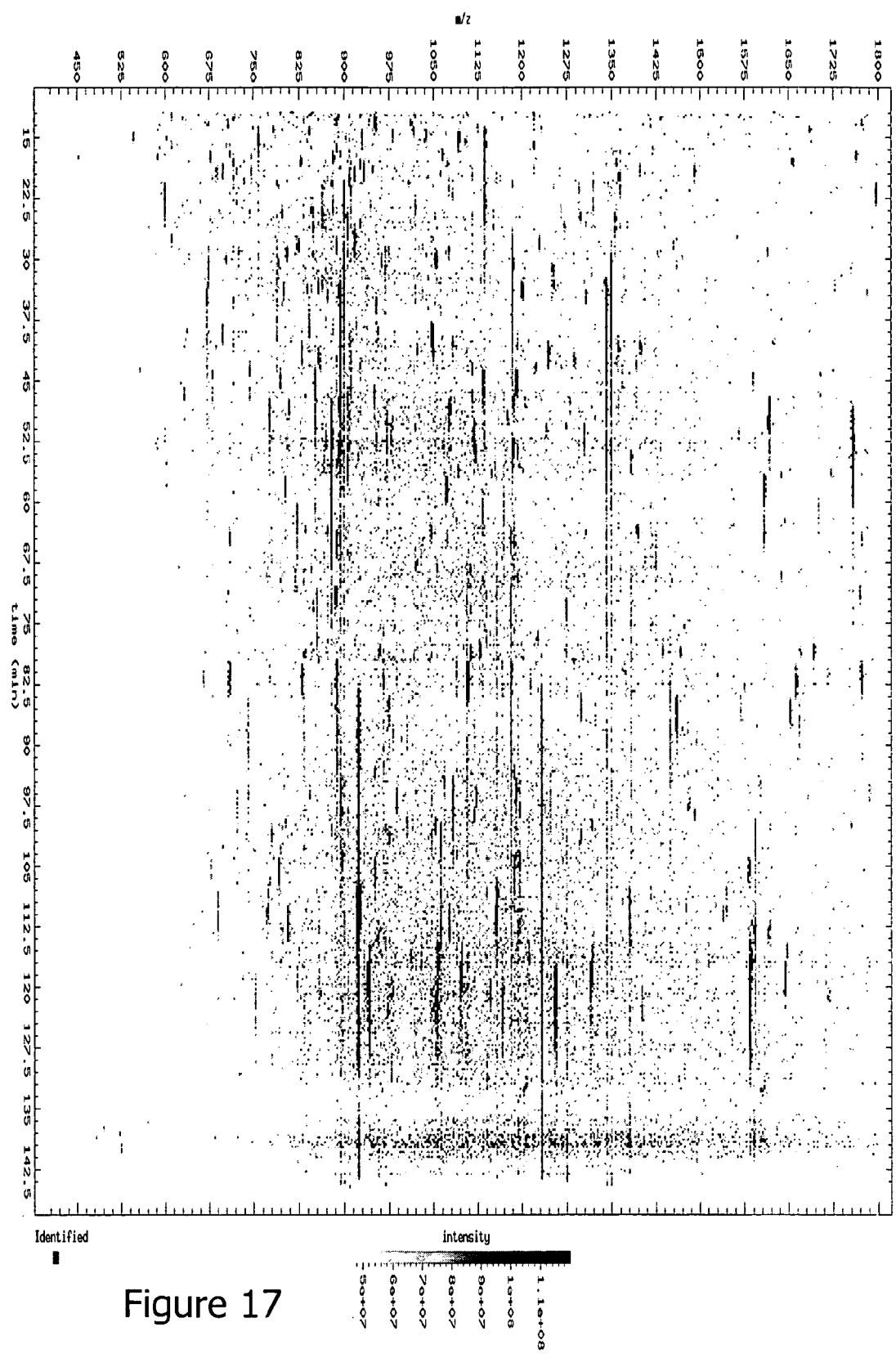
FIG. 17 shows the total peptides present in a single LC-MS/MS run (black dots) and the identified peptides (red dots) by CID acquired during the LC-MS/MS run followed by a search using SEQUEST.

Several advantages of using the glycopeptide capture method and peptide mass to identify serum biomarkers are as follows. (1) It is fast and obviates the need for extensive separation methods. Because of the top down mode of operation of tandem mass spectometry in the time available during a LC-MS/MS experiment, only a fraction of the peptides present is selected for CID to identify the peptide sequence. Consequently, if peptides are detected by their mass only, in the time period of a LC-MS/MS experiment a significantly higher number of peptides can be detected than sequenced. This is illustrated in FIG. 17. The total number of peptides present in a single LC-MS/MS run is shown, and identified peptides are shown by the red dots. It was consistently found that less than 10% of total peptides were identified for complex biological samples. (2) The glycopeptide capture method simplified the total peptides -present in serum after protease digestion and removed the heterogeneity of peptides caused by different oligosaccharides modifications and break down during MS analysis. (3) The majority of proteins and peptides in biological samples were unchanged in different states of the samples. Analyzing the relative abundance of all the peptides present in LC-MS, the peptides that change in abundance can be identified and the CID analysis focused on the differentially expressed proteins for identification.

Figure 18:
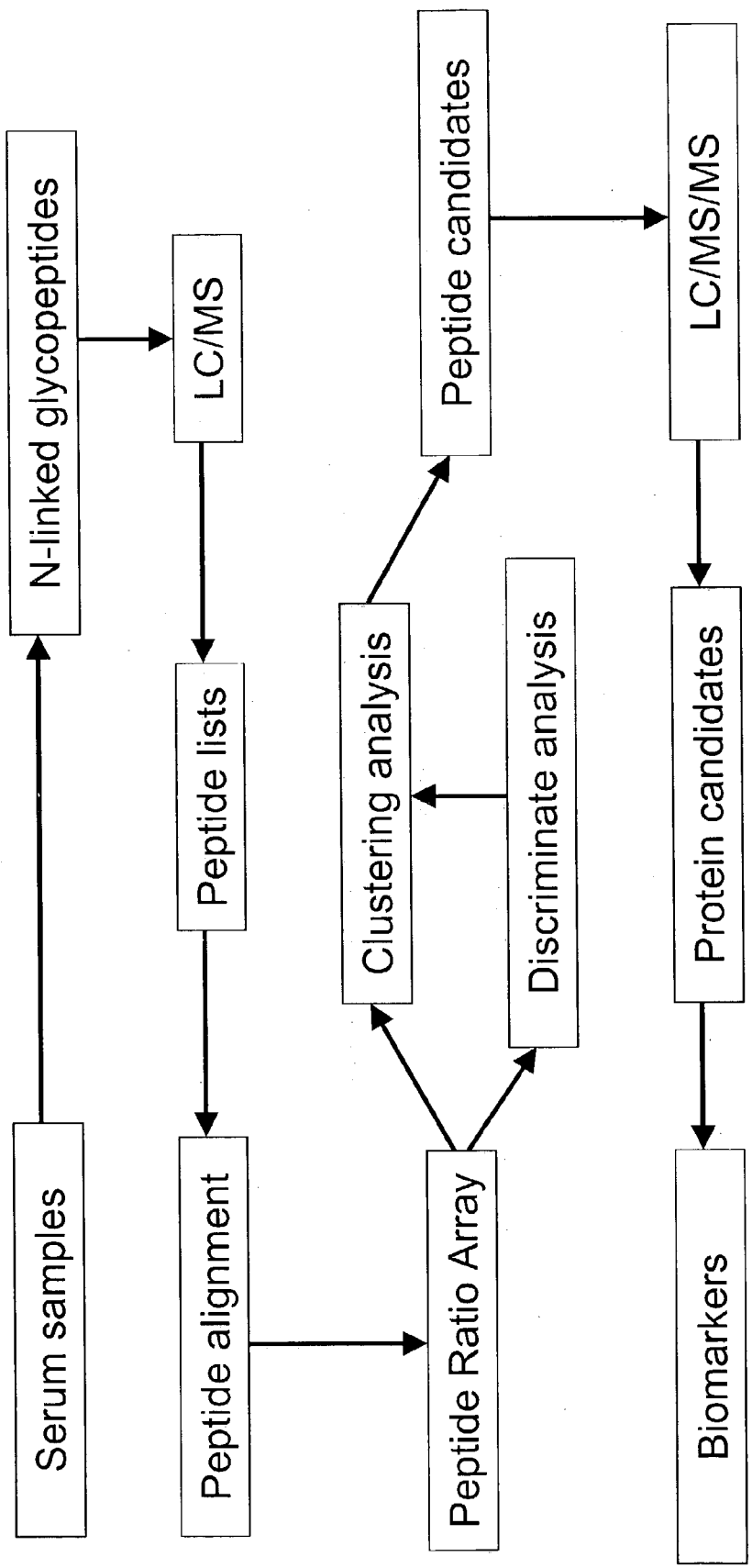
FIG. 18 shows a schematic diagram of the strategy used to profile glycopeptides present in serum and identify biomarkers.
Figure 19:
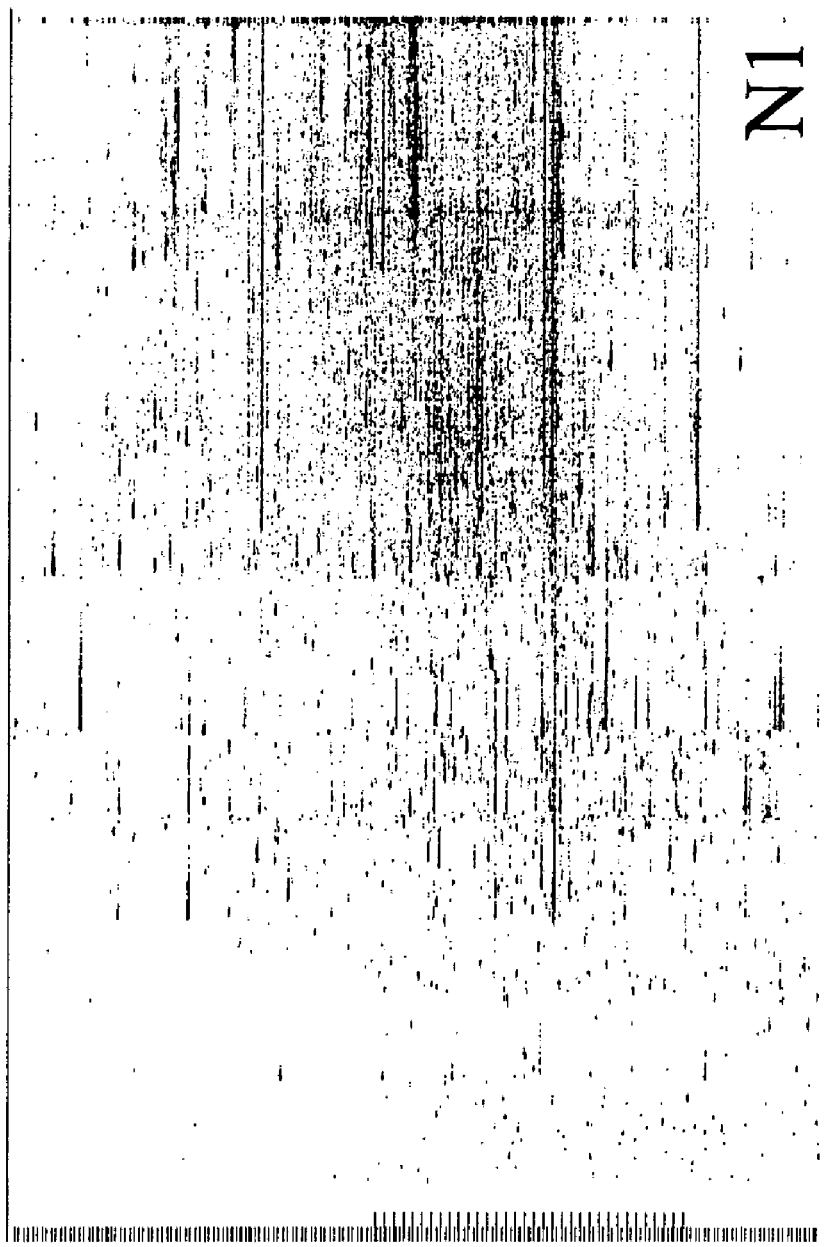
FIG. 19 shows the signal intensity of peptides during the elution of an LC-MS/MS run. N1 and N2 were from normal mouse serum, and T1 and T2 were glycopeptides from mouse serum with skin cancer.
Figure 19:
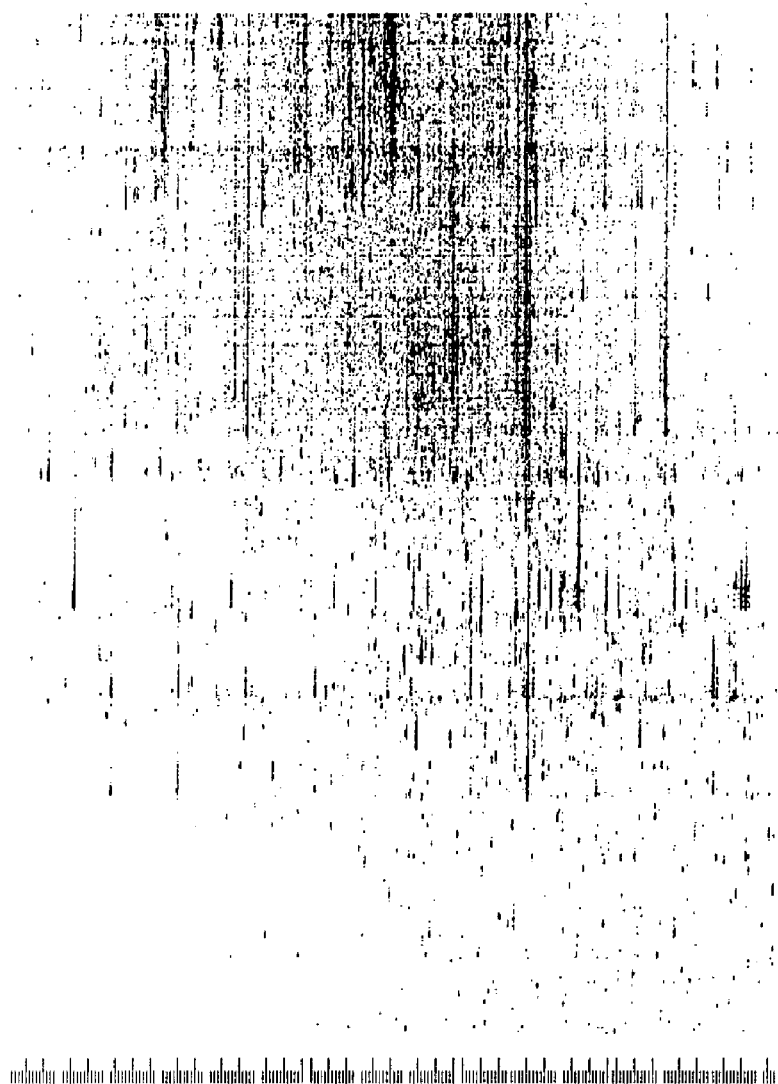
Figure 19:
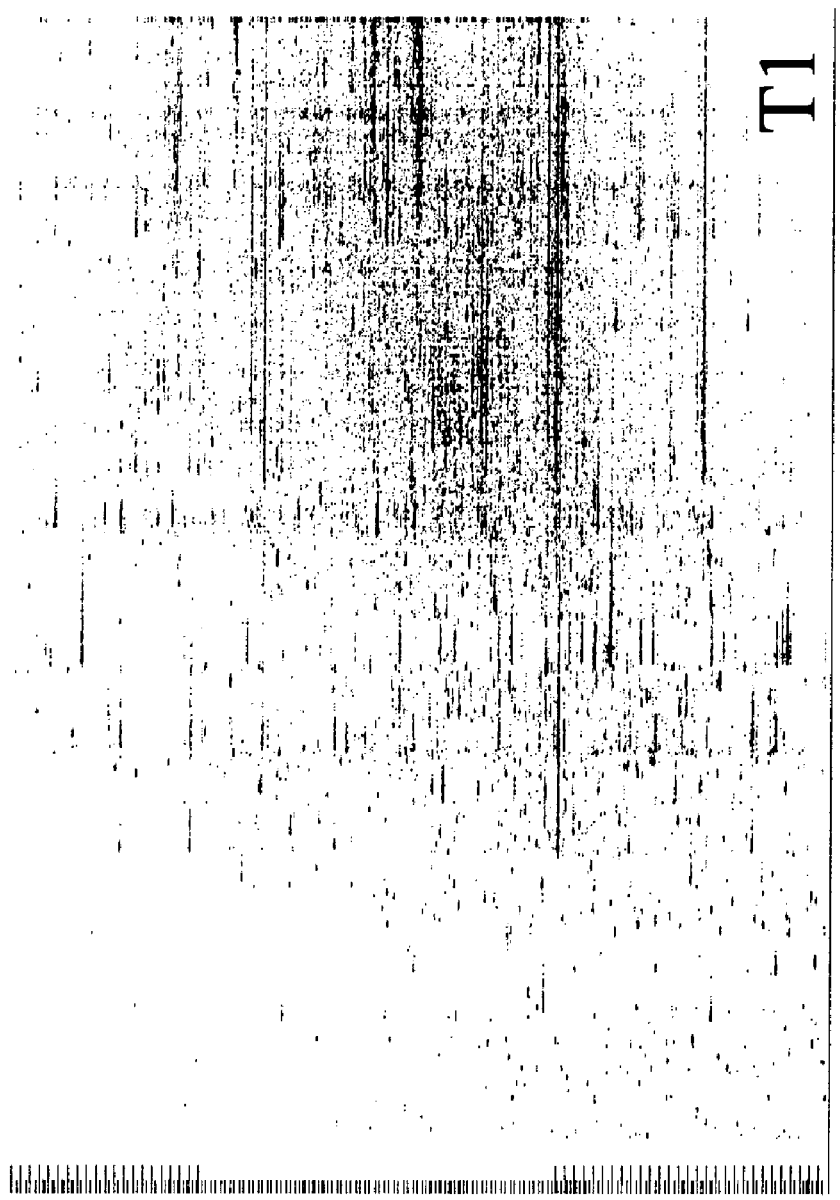
Figure 19:
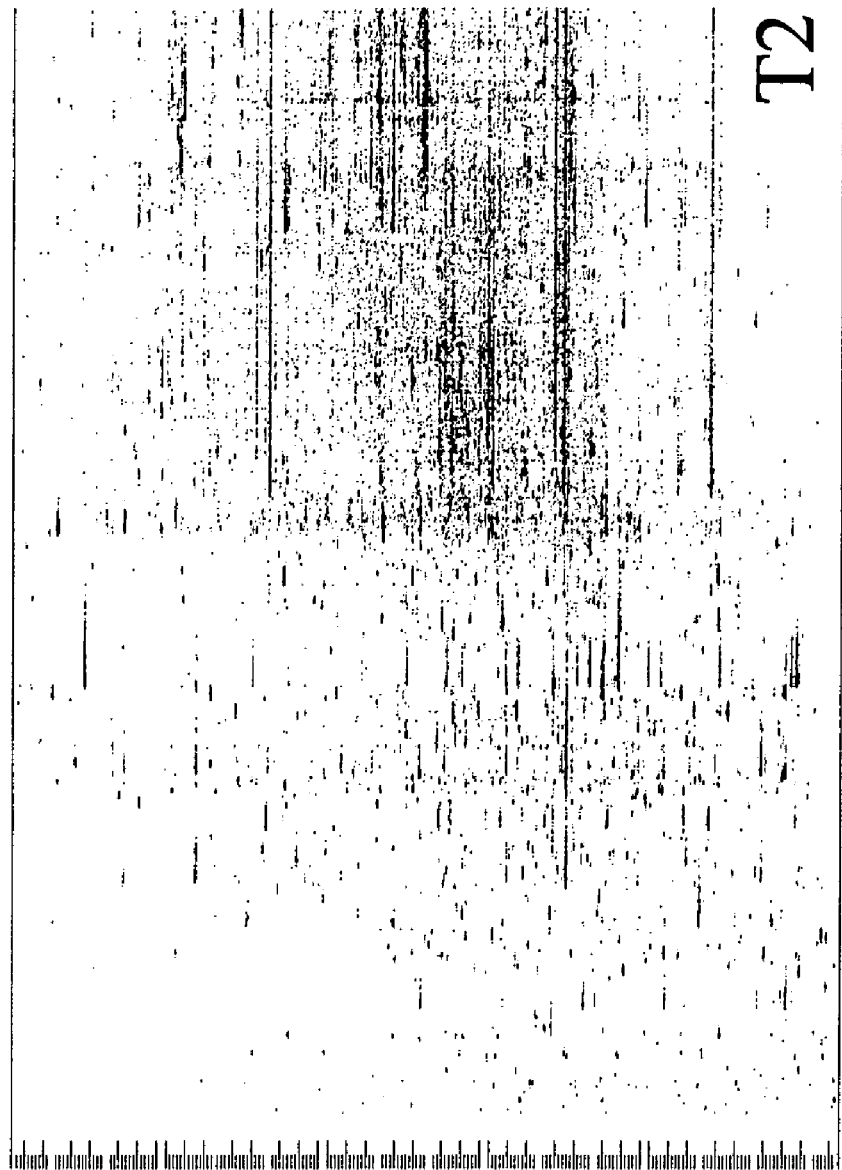

The strategy used to identify the biomarkers in serum is shown schematically in FIG. 18. Glycopeptides from 100 μl of serum from 10 normal and 3 diseased mice were purified as described in Example I. The peptides were resuspended in 30 μl 0.4% acetic acid, and 5 μl of samples were analyzed by LC-MS/MS. FIG. 19 shows the signal intensity of peptides during the elution of the LC-MS/MS run. N1 and N2 were from normal mice, and T1 and T2 were glycopeptides from mice serum with skin cancer. Reproducible patterns of peptides from individual mice were observed during the LC-MS/MS runs.

Figure 20:
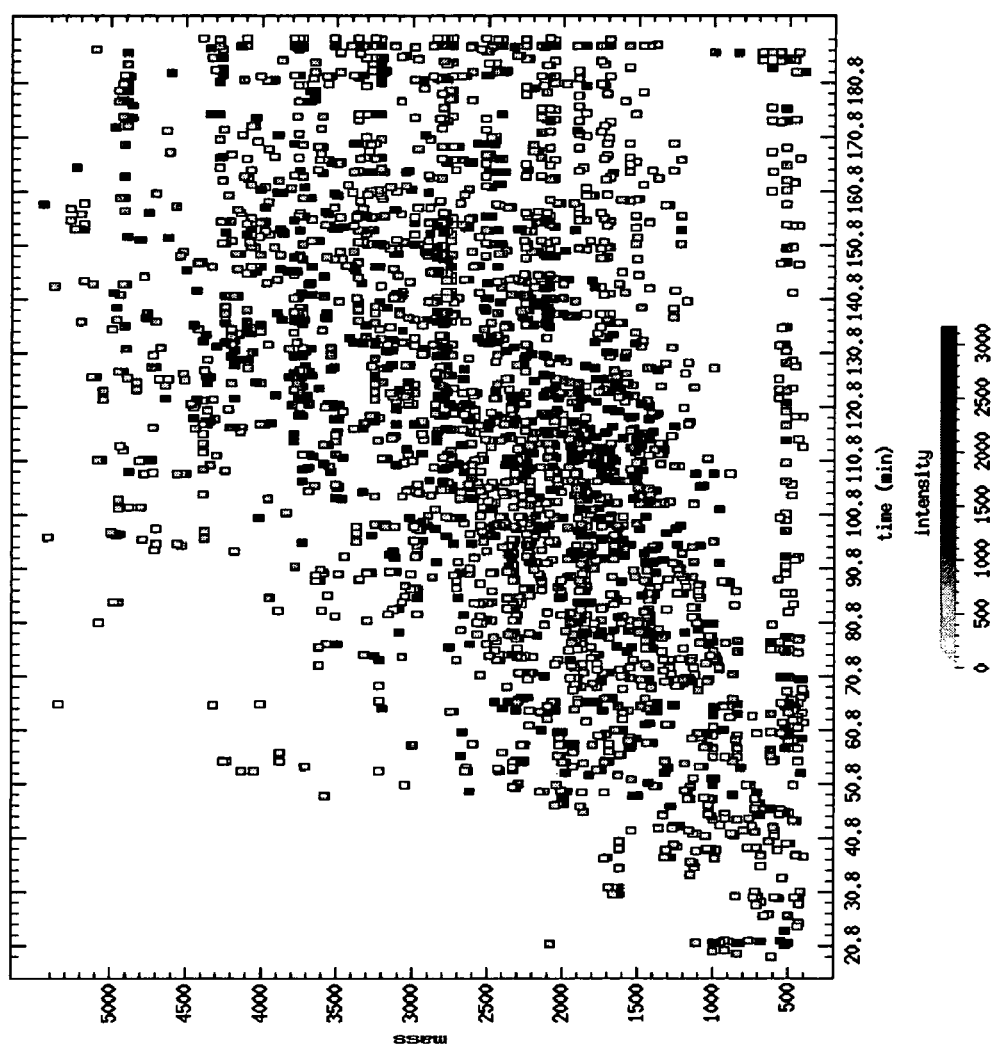
FIG. 20 shows the intensity of deconvoluted peptides during different elution time from serum of normal mice and mice with skin cancer. The left panel shows peptides in normal mouse. The right panel shows peptides in cancer mouse.
Figure 20:
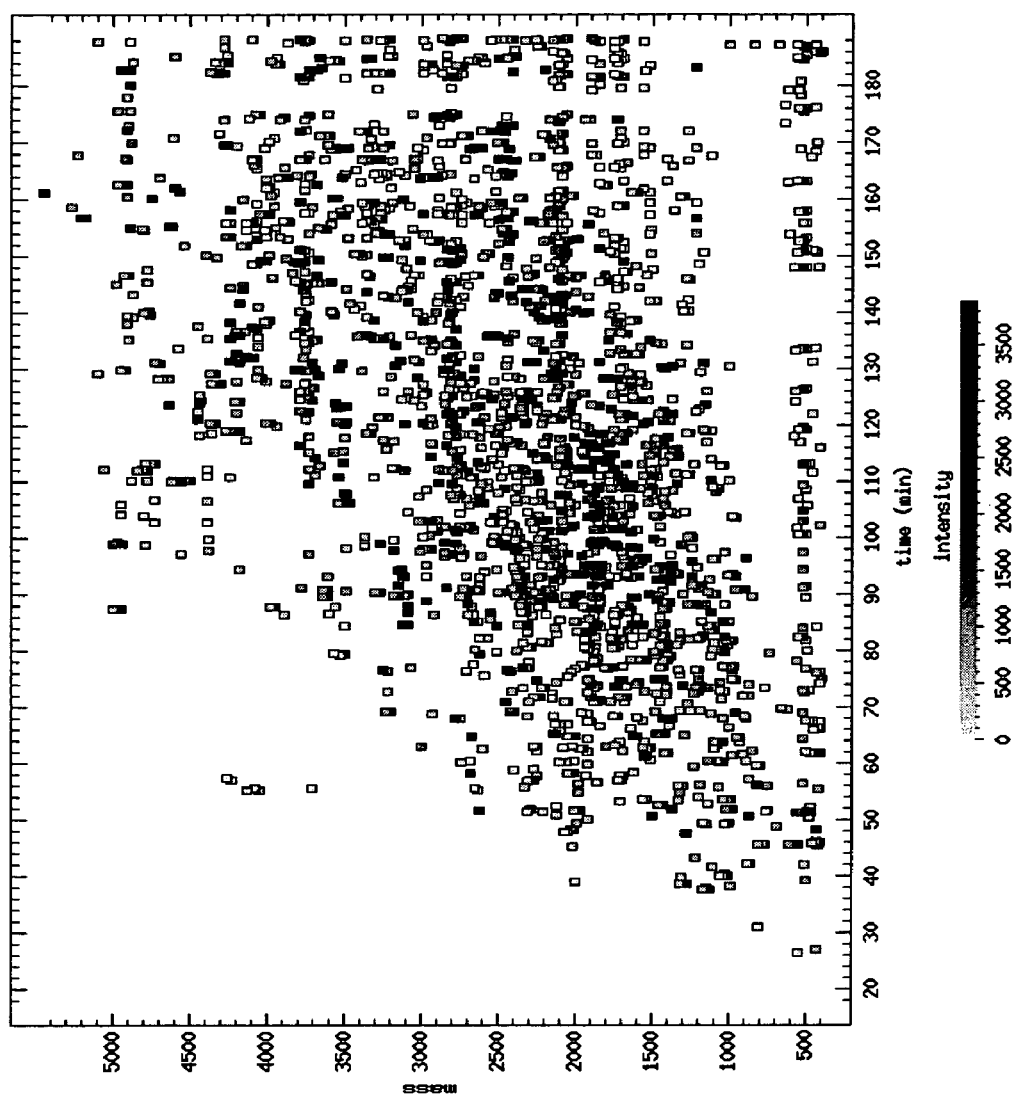
Figure 21:
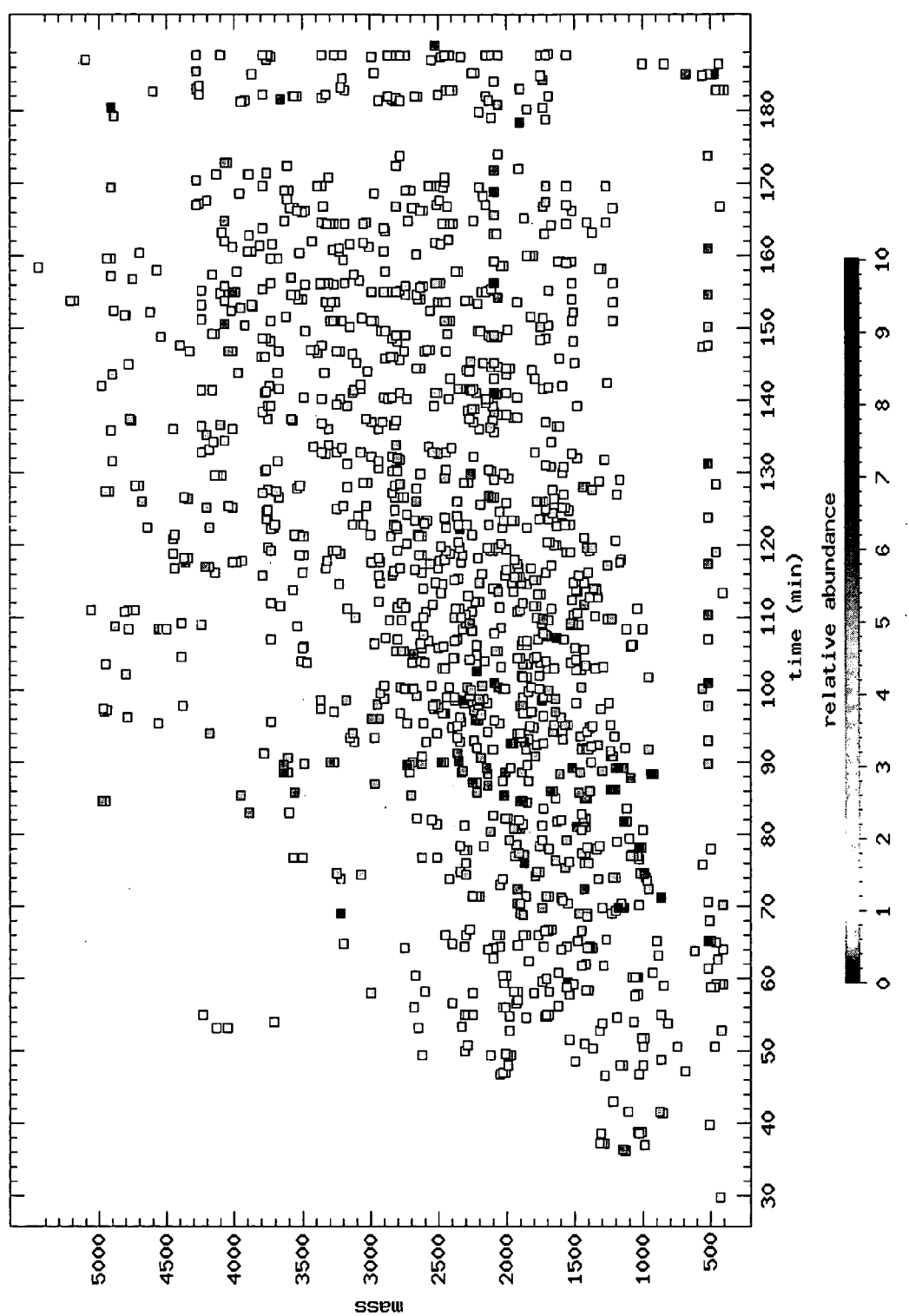
FIG. 21 shows normalized peptide abundance between cancer and normal mouse. The relative peptide intensity of cancer mouse to normal mouse.

Peptide peaks from different charge states in the entire run were deconvoluted to signal charged peptides. FIG. 20 shows the deconvoluted peptides intensity during different elution time from normal and skin cancer mice. About 3000 peptides were consistently observed in different samples. The peptides were then aligned by elution time using in-house developed software, and normalized to background to reduce the variation of different runs. The relative peptide intensity of cancer mouse to normal mouse was calculated and shown in FIG. 21.

Figure 22:
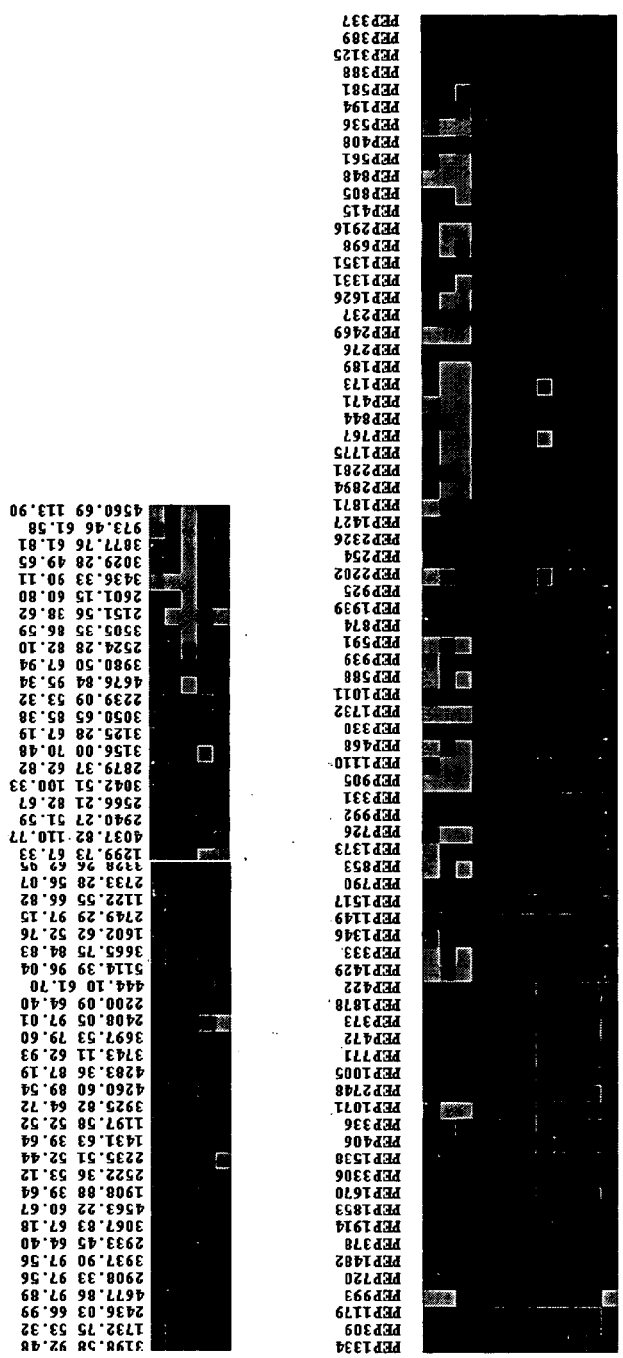
FIG. 22 shows clustering analysis of normal mice and mice with cancer. Automatic, whole feature clustering of mouse serum distinguishes cancer from healthy. All the cancer mice clustered together (indicated as 11A, 12A, 13A in experiment one, upper panel; and M11, M12, M13 in experiment two, lower panel).

To facilitate the quantification, an equal amount of peptides from all 13 mice was mixed and analyzed by mass spectrometry as control. The relative intensity of each peptide to the control after alignment was obtained. The relative peptide intensities from all 13 mice from two different experiments was analyzed by unsupervised hierarchical clustering ((Eisen et al., *Proc. Natl. Acad. Sci. USA* 95:14863–14868 (1998)). No predefined reference vectors and prior knowledge of normal or cancer were used. In this clustering analysis, relationships among peptides were represented by a tree whose branch lengths reflect the degree of similarity between the objects. As shown in FIG. 22, all the cancer mice were found clustered together (indicated as 11A, 12A, 13A in experiment one, and M11, M12, M13 in experiment two). The peptide intensity shown in red indicates that the peptide abundance is lower than the corresponding peptide intensity in the common control, and the peptide intensity shown in green indicates a higher abundance of the peptide compared to the common control of the mixture.

This example shows that peptides isolated by the glycocapture method contain markers for cancer. The analysis of formerly N-linked glycopeptides using peptides mass and retention time increases the information of peptides during the mass spectrometry analysis. This approach is capable of distinguishing the difference between normal mice and mice with cancer and identifying cancer markers from serum.

EXAMPLE X

Quantitative Profiling of Glycopeptides from Human Serum Samples Obtained Before and After Overnight Fasting This example describes the quantitative profiling and clustering analysis of glycopeptides from serum samples of three individuals before and after overnight fasting.

Glycopeptides from 100 μl of serum from three persons before and after overnight fasting were purified as described in Example I. The peptides were resuspended in 30 μl 0.4% acetic acid, and a control sample was made by mixing an equal amount (1 μl) of every glycopeptide from all 6 samples. A 5 μl aliquot of samples was analyzed by LC-MS/MS. The peptide peaks were deconvoluted to single charged peptides. After alignment and normalization of different runs, the relative intensity of each peptide to the common control sample was determined.

Figure 23:
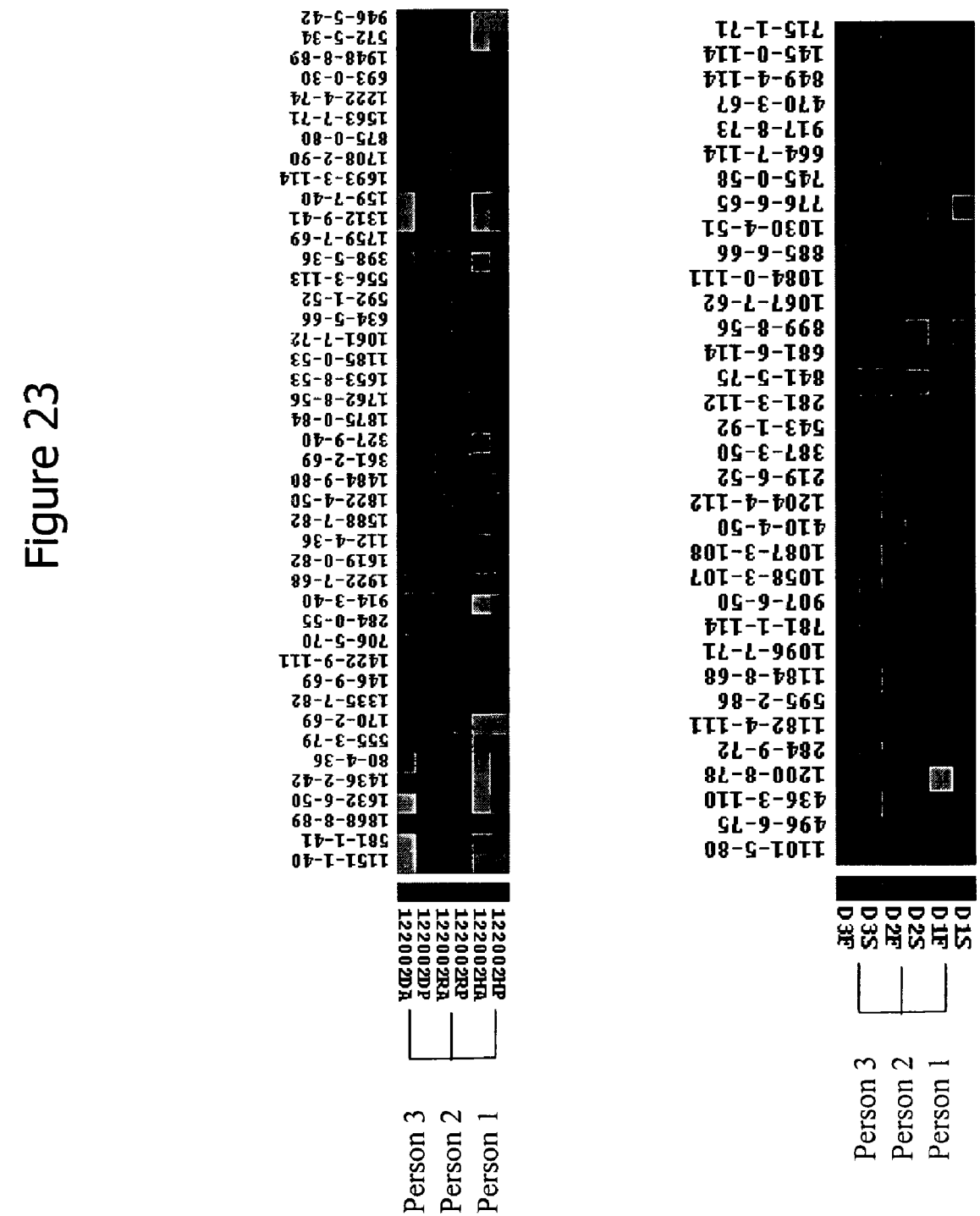
FIG. 23 shows clustering analysis of samples from individuals before and after overnight fasting. Automatic clustering of serum from three individuals before and after overnight fasting consistently separates individuals (experiment one, upper panel; experiment two, lower panel). Serum samples from the same person cluster together.

The relative peptide intensities from three individuals before and after overnight fasting were determined from each experiment and were analyzed by unsupervised hierarchical clustering without prior knowledge of any specificity and conditions of the individual samples ((Eisen et al., *Proc. Natl. Acad. Sci. USA* 95:14863–14868 (1998)). In this clustering analysis, relationships among peptide were represented by a tree whose branch lengths reflect the degree of similarity between the objects. As shown in FIG. 23, it was found that, in both experiments, serum samples from each individual before and after breakfast clustered together (indicated by person 1–3) in both experiments. The color coding is similar to that shown in FIG. 22.

These results show that peptides isolated by the glycocapture method from serum samples of each individual before and after overnight fasting are most closely related. The analysis of formerly N-linked glycopeptides using peptide mass and retention time increases the information on the peptides during the mass spectrometry analysis. This approach is capable of automatically distinguishing the most significant differences between the samples. This shows that glycopeptides from individual serum samples contain the characterstic features that can be used to assess the physiological state of an individual.

EXAMPLE XI

Determination of Glycosylation Occupancy from Serum Samples Obtained from Healthy Individuals or Patients with Type I Congenital Disorders of Glycosylation (CDG)

This example describes glycopeptide profiling of individuals with disorders of glycosylation.

Quantitative analysis of N-linked glycosylation is capable of determining the relative N-linked glycosylation in different proteomes. The cysteine tagging method can be used to determine the relative protein changes in different proteomes (Gygi et al., Nat. Biotechnol. 17:994–999 (1999)). By combining quantitative analysis of N-linked glycosylation with cysteine tagging, the occupancy of individual N-linked glycosylation sites and changes thereof can also be determined. This is of particular interest in studies in which changes of glycosylation occupancy are suspected, as exemplified by patients with Type I Congenital Disorders of glycosylation (CDG), in which the pathway of N-linked glycosylation is deficient (Aebi and Hennet Trends Cell Biol. 11:136–141 (2001)). In addition, changes in the extent of glycosylation and the carbohydrate structure of proteins on the cell surface and in body fluids have been shown to correlate with cancer and other disease states, highlighting the clinical importance of this modification as an indicator or effector of pathologic mechanisms (Spiro, Glycobiology 12:43R–56R (2002); Freeze Glycobiology 11:129R–143R (2001); Durand and Seta, Clin. Chem. 46:795–805 (2000)).

Figure 24:
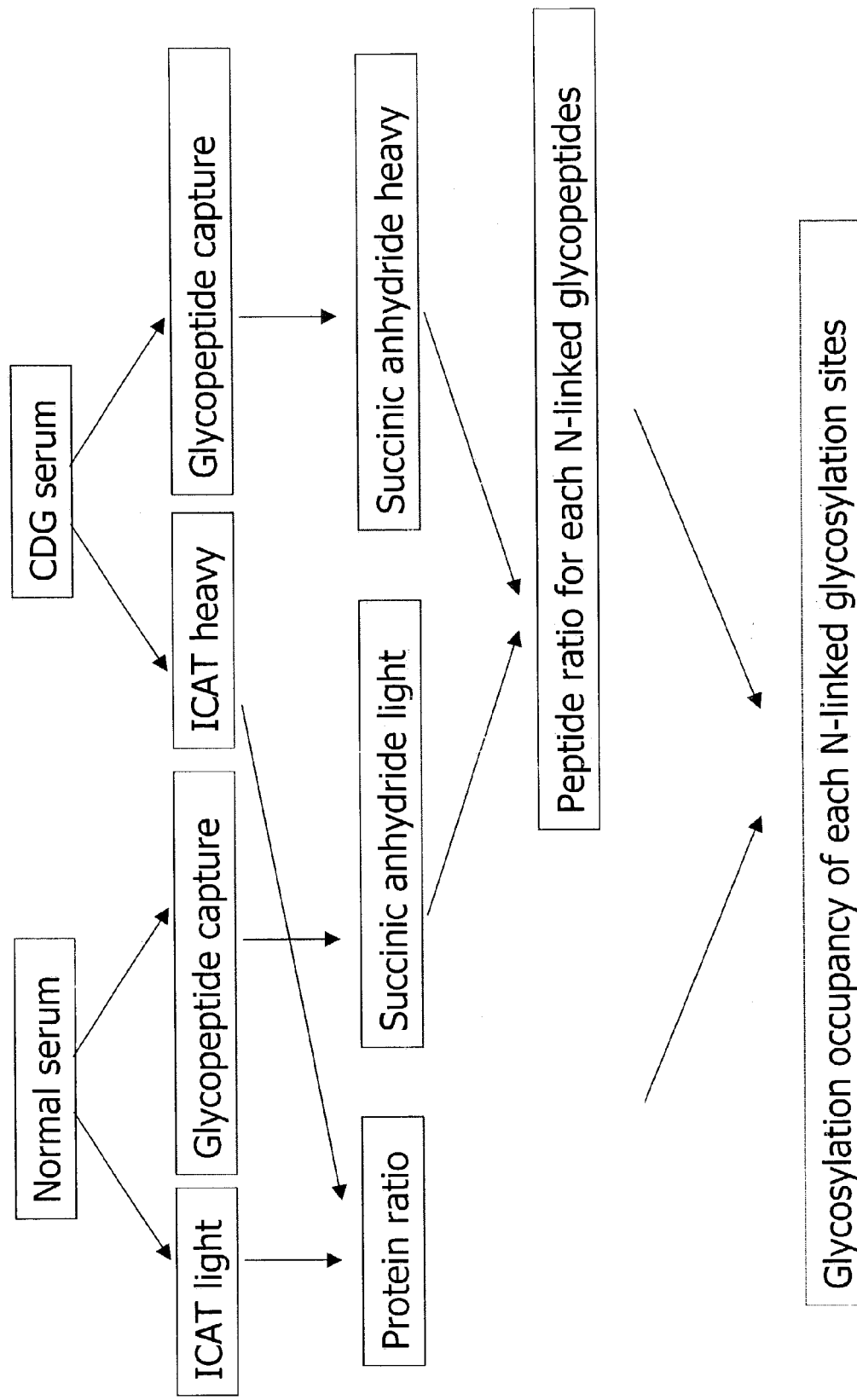
FIG. 24 shows a schematic diagram of a glycosylation occupancy study of serum from congenital disorders of glycosylation (CDG) patients.

The glycosylation occupancy study of serum from CDG patients is described in FIG. 24. The ratio of total serum protein level of an individual was quantified using the ICAT reagent, and the ratio of N-linked glycopeptides of the individual is determined by glycopeptide capture followed by N-terminal isotopic labeling. The glycosylation occupancy is determined by the ratio of each N-linked glycopeptides divided by total protein ratio of the proteins.

To determine the relative ratio of total protein, the ICAT reagent was used to label the protein. Seven samples containing 0.5 mg of serum proteins from normal person #1 was labeled with the ICAT light reagent, and 0.5 mg of serum proteins from normal person #1, normal person #2, CDG 1a patient #1, CDG 1g patient #2, CDG 1b patient #1, CDG 1b patient #2, and CDG 1b patient #3 were labeled with ICAT heavy reagent. The ICAT reagent was purchased from Applied Biosystems, and labeling was performed following the manufactory's instruction.

Briefly, serum proteins (0.5 mg, 6.25 µl) were added to 0.5 ml of ICAT labeling buffer (6M urea, 0.05% SDS, 200 mM Tris, 5 mM EDTA, pH 8.3). The samples were reduced by adding 8 mM tris-carboxyethylphosphine (TCEP) and incubating at 37° C. for 45 minutes. Five fold excess of light and heavy ICAT reagents was added, and labeling was performed in the dark at 37° C. for 2 hours. The seven samples labeled with heavy ICAT reagent were mixed with one of seven normal samples labeled with light ICAT reagent. The seven mixed samples were diluted ten fold, and 5 µg of trypsin was added and incubated at 37° C. overnight. The ICAT labeled tryptic peptides were purified by avidin affinity chromatography using a Vision chromatography worksta- tion from Applied Biosystems (Foster City, Calif.). The peptides were resuspended in 20 µl of 0.4% acetic acid, and 5 µl of peptides were analyzed by Finnigan LCQ ion trap mass spectrometer (Finnigan, San Jose, Calif.). The CID spectra were searched against the human NCI database using Sequest. A suite of software tools developed at the Institute for Systems Biology were used to analyze protein identification and relative expression ratio, including probability analysis of peptide and protein identification, and expression ratio of each protein (Eng et al., J. Am. Soc. Mass Spectrom. 5:976–989 (1994); Han et al., Nat. Biotechnol. 19:946–951 (2001); Keller et al., Anal. Chem. 74:5383–5392 (2002)). The protein ratio from normal person #1 to normal person #1 is shown in Table 6. The ratio agreed well with the expected 1:1 ratio.

TABLE 6

| Protein expression ratio determined by ICAT labeling | |
|---|---|
| Protein name | ratio of protein expression |
| GP:A00279_1 | 0.803 +− 0.268 |
| GP:AB064062_1 | 0.826 +− 0.140 |
| GP:AB064121_1 | 0.975 +− 0.091 |
| GP:AJ390244_1 | 1.464 +− 0.269 |
| PIR2:A37927 | 0.795 +− 0.268 |
| SW:A2HS_HUMAN | 0.847 +− 0.224 |
| SW:A2MG_HUMAN | 0.967 +− 0.138 |
| SW:ALBU_HUMAN | 1.166 +− 0.036 |
| SW:ALC1_HUMAN | 1.352 +− 0.115 |
| SW:ALC2_HUMAN | 1.327 +− 0.539 |
| SW:AMBP_HUMAN | 1.208 +− 0.292 |
| SW:APA2_HUMAN | 1.047 +− 0.178 |
| SW:APOH_HUMAN | 0.991 +− 0.176 |
| SW:CFAB_HUMAN | 1.388 +− 0.757 |
| SW:CFAH_HUMAN | 1.043 +− 0.111 |
| SW:CO3_HUMAN | 0.896 +− 0.063 |
| SW:FIBB_HUMAN | 1.093 +− 0.218 |
| SW:FIBG_HUMAN | 0.949 +− 0.184 |
| SW:FINC_HUMAN | 1.391 +− 0.126 |
| SW:GC1_HUMAN | 1.195 +− 0.058 |
| SW:GC2_HUMAN | 1.047 +− 0.249 |
| SW:GC4_HUMAN | 1.195 +− 0.425 |
| SW:HEMO_HUMAN | 1.057 +− 0.086 |
| SW:HPT1_HUMAN | 1.152 +− 0.091 |
| SW:HPTR_HUMAN | 1.377 +− 0.206 |
| SW:ITH2_HUMAN | 1.330 +− 0.314 |
| SW:KAC_HUMAN | 1.072 +− 0.146 |
| SW:LAC_HUMAN | 1.063 +− 0.592 |
| SW:MUCB_HUMAN | 1.191 +− 0.536 |
| SW:MUC_HUMAN | 0.986 +− 0.221 |
| SW:TRFE_HUMAN | 1.183 +− 0.061 |
| SW:VTDB_HUMAN | 1.394 +− 0.204 |

To determine the relative glycosylation ratio of each N-linked glycosylation site, seven aliquots of 1 mg (12.5 µl) from normal person #1, and 1 mg of serum from normal person #1, normal person #2, CDG 1a patient #1, CDG 1g patient #2, CDG 1b patient #1, CDG 1b patient #2, and CDG 1b patient #3 were subjected to the glycopeptide capture method as described in Example I. Glycopeptides from the seven samples from normal person #1 were labeled with light succinic anhydride, and the other samples were labeled with heavy succinic anhydride while the glycopeptides were still attached to solid beads. The paired normal and seven individuals are mixed, and formerly N-linked glycosylated peptides are released. The peptides were resuspended in 20 µl of 0.4% acetic acid and 5 µl of peptides were analyzed by Finnigan LCQ ion trap mass spectrometer (Finnigan, San Jose, Calif.). The CID spectra were searched against the human NCI database using Sequest, a suite of software tools developed in Institute for Systems Biology were used to analyze the peptide and protein probability and protein expression ratio using ASAPratio. The ratio of glycosylated peptides is divided by the total protein ratio, and the glycosylation occupancy is determined for each N-linked glycosylation sites.

EXAMPLE XII

Determination of the Level of Glycosylation from Diabetic Obese Mouse Serum

This example describes the determination of glycosylation in a model of diabetes.

Nonenzymatic glycation in diabetes results from the reaction between glucose and primary amino groups on proteins to form glycated residues. The glycated proteins and the later-developing advanced glycation end-products have been mechanistically linked to the pathogenesis of diabetic nephropathy. Glycated albumin has been causally linked to the pathobiology of diabetic renal disease (Cohen and Ziyadeh, *J. Am. Soc. Nephrol.* 7:183–190 (1996)).

Figure 25:
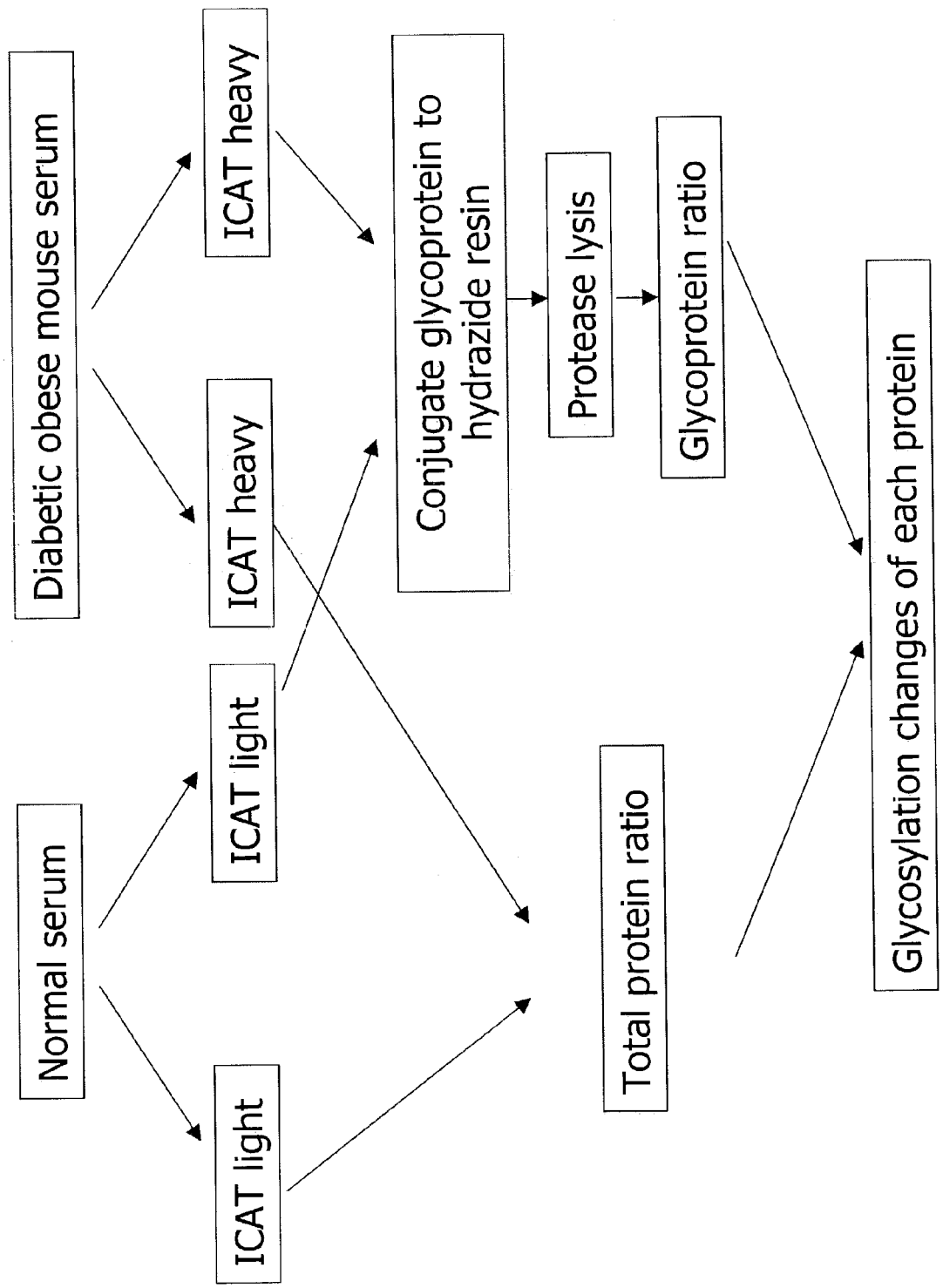
FIG. 25 shows a schematic diagram of a study on total level of glycosylation using serum from obese and normal mice.

Other proteins in serum may be also responsible for the development of diabetic complications. Samples are analyzed for changes in carbohydrate modified serum proteins. Serum from wild type liter mates and diabetic obese mice from BTBR mouse strain are labeled with light and heavy ICAT reagent as shown in FIG. 25. The labeled serum samples are divided into two equal fractions, and paired light and heavy serum from normal and diabetic obese mouse samples are mixed. One mixture is used to determine the total serum protein ratio using the ICAT measurement. The second mixture is conjugated to a solid support using hydrazide chemistry. The cysteine containing peptides from glycoproteins are released by trypsin and isolated by avidin chromatography column using the Vision chromatography workstation (ABI). The relative abundance of glycoproteins between normal and diabetic mice is determined. After normalization to the total protein in serum, the changes of glycosylation are determined.

This experiment shows that the glycopeptide capture method can be used to analyze enzymatically glycosylated proteins as well as non-enzymatic lysine glycation of proteins. The level of non-enzymatic glycation increases in certain diseases caused by diabetes due to the high glucose levels in the patient's blood serum.

EXAMPLE XIII

Quantification of N-linked Glycopeptides Using Heavy Isotope Labeled Synthetic Peptide Standards This example describes quantification using labeled synthetic peptide standards.

Table 7 shows several synthetic peptides (SEQ ID NOS: 198–209) identified from human serum, as described in Example II. The peptides were synthesized using standard solid phase synthesis chemistry with the carbon 13 amino acid incorporated in the valine residues at the underlined position. The glycosylated asparagines were also changed to aspartic acid. 500 fmol of each peptide was mixed and run separately on LC-MS/MS analysis to determine the retention time and CID spectra. The same amount of peptides was mixed with human serum samples from three individuals to determine the relative amount of these glycopeptides in serum.

FIG. 26 shows the synthetic peptides identified by mass spectrometry.

TABLE 7

Synthetic heavy isotope labeled peptide standards.

| Protein Name | Peptide Sequence |
|---|---|
| Plasma protease C1 inhibitor precursor | GVTSVSQIFHSPDLAIRDTFVDASR |
| Angiotensinogen precursor [Contains: Angiotensin I] | VYIHPFHLVIHDESTCEQLAK |
| Pigment epithelium-derived factor precursor | VTQDLTLIEESLTSEFIHDIDR |
| Serum amyloid A-4 protein precursor | SRVYLQGLIDYYLFGDSSTVLEDSK |
| Complement component C9 precursor | AVDITSENLIDDVVSLIR |
| Biotinidase precursor | YQFNTNVVFSNDGTLVDR |
| Coagulation factor XIII B chain precursor | HGVIISSTVDTYEDGSSVEYR |
| Alpha-1-acid glycoprotein 2 precursor | QNQCFYDSSYLNVQR |
| Plasma serine protease inhibitor precursor | VVGVPYQGDATALFILPSEGK |
| Aminopeptidase N | GPSTPLPEDPNWDVTEFHTTPK |
| Antithrombin-III precursor | SLTFDETYQDISELVYGAK |
| ICOS ligand precursor | TDNSLLDQALQDDTVFLNMR |

The samples are analyzed for glycopeptides as described in Example I. These results show that a known amount of synthetic peptides can be used to determine the relative or absolute amount of the same glycopeptides in individual serum samples.

EXAMPLE XIV

Identification of O-linked Glycopeptides Using Enzymatic Cleavage

This example describes identification of O-linked glycopeptides.

Analogous strategies to those described herein for analysis of N-linked glycosylation sites can be used to also analyze O-glycosylated peptides. In fact, a protein sample, once immobilized on a solid support, can be subjected to sequential N-linked and O-linked glycosylation peptide release, thus further increasing the resolution of the method and the information contents of the data obtained by it. There is no enzyme comparable to PNGase F for removing intact O-linked sugars. To release O-linked oligosaccharides, monosaccharides are sequentially removed by using a panel of exoglycosidases until only the Galβ1,3GalNAc core remains attached to the serine or threonine residue. The core can then be released by O-glycosidase. Since not all O-linked oligosaccharides contain this core structure, a chemical method, such as β-elimination can be more general and effective for the release of the formerly O-linked glycosylated peptides.

After releasing N-linked glycopeptides, 100 μl of hydrazide resin was washed with 1 ml of 1.5 M NaCl twice, 1 ml of 100% methanol twice, and 1 ml of water twice. O-linked glycopeptides were cleaved by a set of enzymes (Calbiochem), including Endo-α-N-acetylgalactosaminidase, Neuraminidase, β1,4-Galactosidase, and β-N-Acetylglucosaminidase. The released peptides were dried and resuspended in 0.4% acetic acid for LC-MS/MS analysis.

FIG. 27 shows the identified peptides from the series of enzymatic cleavages from hydrazide resin after N-linked glycopeptides were released. Unlike the N-linked glycosylation, in which PNGase F converts the glycosylated N to D after release of oligosaccharides, O-linked glycosylated serine or threonine remained unchanged. There are no known consensus motifs available for O-linked glycosylation. To date, the serine or threonine residues to which the O-linked oligosaccharides were attached have not been identified.

This example demonstrates that O-linked glycopeptides can also be identified.

EXAMPLE XV

Identification of Glycopeptides Isolated by Biotin Tagged Hydrazide

This example describes identification of glycopeptides isolated by biotin tagged hydrazide.

The same procedure described in Example I was also performed in solution phase using biotin tagged hydrazide (PIERCE) with some modifications. After proteins were oxidized and conjugated to biotin hydrazide, the proteins were denatured in 0.5% SDS and 8M urea in 0.4 M $NH_4CO_3$ for 30 minutes at room temperature. The samples were diluted 4 times with water, and trypsin was added at a final concentration of 1:100. The trypsin digest was performed overnight at room temperature. The glycopeptides conjugated to biotin hydrazide were purified by an avidin column using the Vision chromatography workstation. The glycopeptides were isolated with oligosaccharides still attached to the peptides. The peptides were dried and resuspended in 0.4%. acetic acid and analyzed by mass spectrometry.

Figure 29:
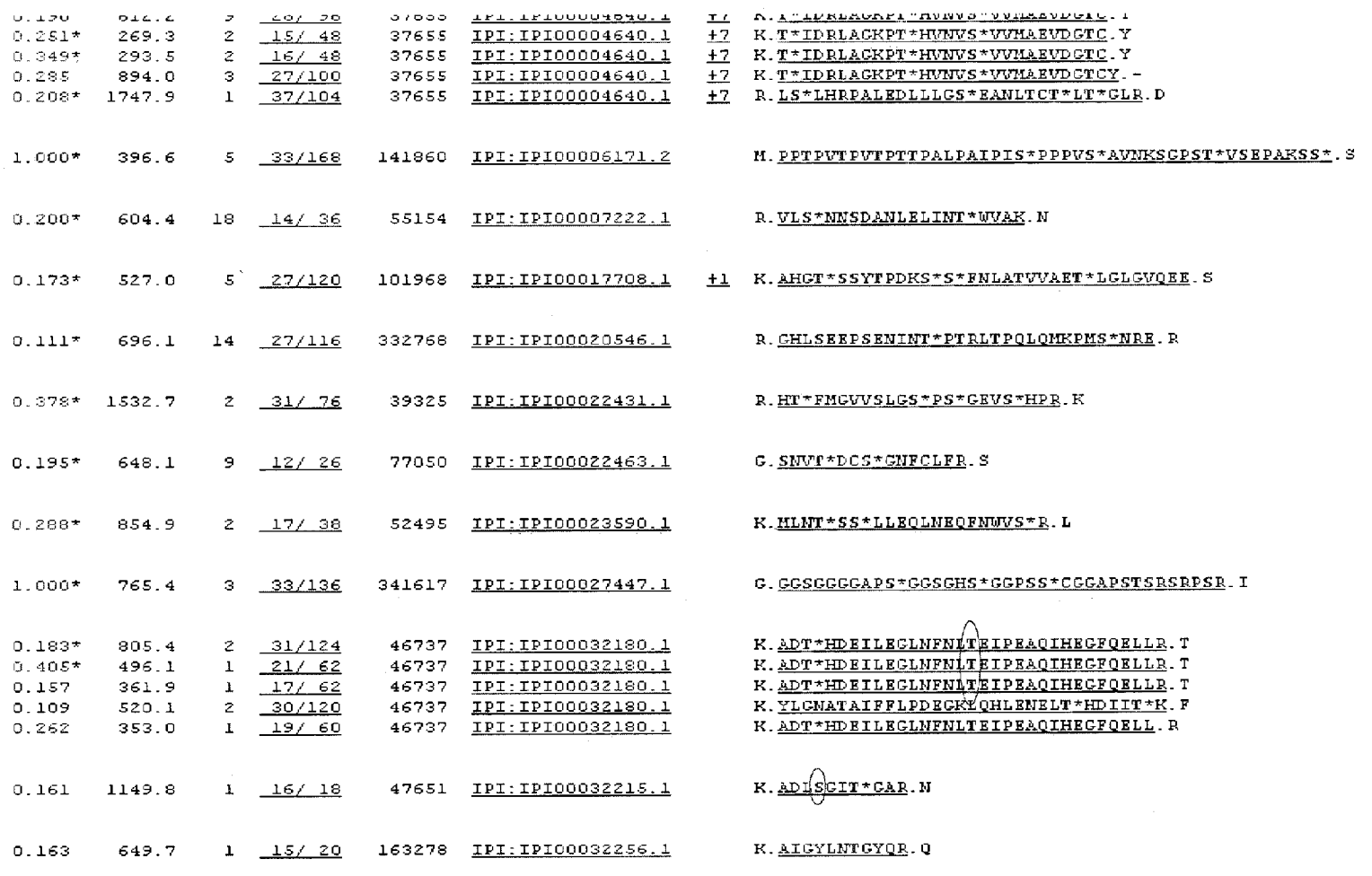

When high spray voltage was used in ESI-LC-MS/MS analysis (2.0 kv), the oligosaccharides were separated from peptide at the source. It resulted in the analysis of N-linked peptides and O-linked peptides by mass spectrometry. The identified N-linked glycopeptides are shown in FIG. 28, with the consensus NXT/S motif highlighted. The O-linked oligosaccharides were removed in the source with a loss of water. This left the formerly O-linked glycosylation Ser or Thr with 18 Dalton less than the unmodified Ser or Thr. This is represented in FIG. 29 at S or T without modification (shown in circles).

These results show that the glycopeptide capture method can also be performed via affinity reactive tags attached to the protein by solution chemistry. The glycopeptides isolated by this method can have oligosaccharide chains attached to the glycopeptides. Both N-linked and O-linked glycopeptides can be isolated and analyzed simultaneously.

EXAMPLE XVI

Automation of the Glycopeptide Capture Method Using a TECAN Workstation

This example describes adaptation of the glycopeptide analysis method to automation.

To improve the throughput and reproducibility of the method of glycopolypeptide analysis, an automated robotic workstation was designed to perform the sequence of reactions for glycopeptide isolation. The workstation is particularly useful for all applications requiring high sample throughput. The procedure described in Example I is tested in solid phase extraction format for automation. in serum biomarker identification A TECAN workstation was designed for the glycopeptide capture procedure. The workstation is used to automate sampling and analysis of glycopeptides. The workstation can be readily adapted to diagnostic applications, for example, the analysis of a large number of serum samples or other biological samples of diagnostic interest.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method for identifying and quantifying a glycopolypeptide in a sample, comprising:
    (a) derivatizing carbohydrate groups of glycopolypeptides in a polypeptide sample;
    (b) immobilizing said derivatized carbohydrate groups of said glycopolypeptides to a solid support;
    (c) cleaving said immobilized glycopolypeptides, thereby releasing non-glycosylated peptide fragments and retaining immobilized glycopeptide fragments;
    (d) labeling said immobilized glycopeptide fragments with an isotope tag;
    (e) releasing said glycopeptide fragments from said solid support, thereby generating released glycopeptide fragments;
    (f) analyzing said released glycopeptide fragments using mass spectrometry;
    (g) identifying a released glycopeptide fragment;
    (h) quantifying the amount of said glycopeptide fragment identified in step (g);
    (i) identifying the glycopolypeptide from which the glycopeptide fragment in step (g) was derived, thereby identifying and quantifying the glycopolypeptide.

2. The method of claim 1, wherein said solid support comprises a hydrazide moiety.

3. The method of claim 1, wherein said glycopeptides are released from said solid support using a glycosidase.

4. The method of claim 3, wherein said glycosidase is an N-glycosidase or an O-glycosidase.

5. The method of claim 4, wherein said glycopeptides are released from said solid support using sequential addition of N-glycosidase and O-glycosidase.

6. The method of claim 1, wherein said glycopeptides are released from said solid support using chemical cleavage.

7. The method of claim 1, wherein said glycopolypeptides are oxidized with periodate.

8. The method of claim 1, wherein said glycopolypeptides are cleaved with trypsin.

9. The method of claim 1, wherein said released non-glycosylated peptides are isotopically labeled and analyzed by mass spectrometry.

10. The method of claim 1, wherein said sample is selected from a body fluid, secreted proteins, and cell surface proteins.

* * * * *

SEQUENCE LISTING

```
<160> NUMBER OF SEQ ID NOS: 210

<210> SEQ ID NO 1
<211> LENGTH: 15
<212> TYPE: PRT
<213> ORGANISM: Mus musculus

<400> SEQUENCE: 1

Lys Asn Ser Thr Leu Cys Asp Leu Cys Ile Gly Pro Leu Lys Cys
1               5                   10                  15

<210> SEQ ID NO 2
<211> LENGTH: 20
<212> TYPE: PRT
<213> ORGANISM: Mus musculus

<400> SEQUENCE: 2

Leu Met Met Asp Tyr Leu Gly Asn Ala Thr Ala Val Phe Leu Leu Pro
1               5                   10                  15
```

-continued

Asp Asp Gly Lys
          20

<210> SEQ ID NO 3
<211> LENGTH: 18
<212> TYPE: PRT
<213> ORGANISM: Mus musculus

<400> SEQUENCE: 3

Lys Tyr Thr Gly Asn Ala Ser Ala Leu Phe Ile Leu Pro Asp Gln Gly
1               5                   10                  15

Arg Met

<210> SEQ ID NO 4
<211> LENGTH: 21
<212> TYPE: PRT
<213> ORGANISM: Mus musculus

<400> SEQUENCE: 4

Lys Asp Tyr Arg Pro Ser Ala Gly Asn Asn Ser Leu Tyr Gln Asp Thr
1               5                   10                  15

Val Val Phe Lys Cys
          20

<210> SEQ ID NO 5
<211> LENGTH: 15
<212> TYPE: PRT
<213> ORGANISM: Mus musculus

<400> SEQUENCE: 5

Lys Leu Thr Glu Phe Thr His Asn Ser Thr Met Asp Tyr Lys Cys
1               5                   10                  15

<210> SEQ ID NO 6
<211> LENGTH: 18
<212> TYPE: PRT
<213> ORGANISM: Mus musculus

<400> SEQUENCE: 6

Lys Asn Leu Ile Asn Asp Tyr Val Ser Asn Gln Thr Gln Gly Met Ile
1               5                   10                  15

Lys Glu

<210> SEQ ID NO 7
<211> LENGTH: 18
<212> TYPE: PRT
<213> ORGANISM: Mus musculus

<400> SEQUENCE: 7

Lys Tyr Thr Gly Asn Ala Ser Ala Leu Leu Ile Leu Pro Asp Gln Gly
1               5                   10                  15

Arg Met

<210> SEQ ID NO 8
<211> LENGTH: 18
<212> TYPE: PRT
<213> ORGANISM: Mus musculus

<400> SEQUENCE: 8

Lys Val Val Leu His Pro Asn His Ser Val Val Asp Ile Gly Leu Ile
1               5                   10                  15

Lys Leu

```
<210> SEQ ID NO 9
<211> LENGTH: 15
<212> TYPE: PRT
<213> ORGANISM: Mus musculus

<400> SEQUENCE: 9

Lys Asn Leu Phe Leu Asn His Ser Glu Thr Ala Ser Ala Lys Asp
 1               5                  10                  15

<210> SEQ ID NO 10
<211> LENGTH: 18
<212> TYPE: PRT
<213> ORGANISM: Mus musculus

<400> SEQUENCE: 10

Lys His Ser Ile Glu His Phe Asn Asn Thr Asp His Ser His Leu
 1               5                  10                  15

Phe Thr

<210> SEQ ID NO 11
<211> LENGTH: 23
<212> TYPE: PRT
<213> ORGANISM: Artificial Sequence
<220> FEATURE:
<223> OTHER INFORMATION: synthetic peptide

<400> SEQUENCE: 11

Arg Val Val Gly Val Pro Tyr Gln Gly Asn Ala Thr Ala Leu Phe Ile
 1               5                  10                  15

Leu Pro Ser Glu Gly Lys Met
            20

<210> SEQ ID NO 12
<211> LENGTH: 27
<212> TYPE: PRT
<213> ORGANISM: Artificial Sequence
<220> FEATURE:
<223> OTHER INFORMATION: synthetic peptide

<400> SEQUENCE: 12

Lys Gly Val Thr Ser Val Ser Gln Ile Phe His Ser Pro Asp Leu Ala
 1               5                  10                  15

Ile Arg Asp Thr Phe Val Asn Ala Ser Arg Thr
            20                  25

<210> SEQ ID NO 13
<211> LENGTH: 23
<212> TYPE: PRT
<213> ORGANISM: Artificial Sequence
<220> FEATURE:
<223> OTHER INFORMATION: synthetic peptide

<400> SEQUENCE: 13

Lys His Gly Val Ile Ile Ser Ser Thr Val Asp Thr Tyr Glu Asn Gly
 1               5                  10                  15

Ser Ser Val Glu Tyr Arg Cys
            20

<210> SEQ ID NO 14
<211> LENGTH: 24
<212> TYPE: PRT
<213> ORGANISM: Artificial Sequence
<220> FEATURE:
```

<223> OTHER INFORMATION: synthetic peptide

<400> SEQUENCE: 14

Lys Gly Pro Ser Thr Pro Leu Pro Glu Asp Pro Asn Trp Asn Val Thr
1               5                   10                  15

Glu Phe His Thr Thr Pro Lys Met
            20

<210> SEQ ID NO 15
<211> LENGTH: 17
<212> TYPE: PRT
<213> ORGANISM: Artificial Sequence
<220> FEATURE:
<223> OTHER INFORMATION: synthetic peptide

<400> SEQUENCE: 15

Arg Gln Asn Gln Cys Phe Tyr Asn Ser Ser Tyr Leu Asn Val Gln Arg
1               5                   10                  15

Glu

<210> SEQ ID NO 16
<211> LENGTH: 20
<212> TYPE: PRT
<213> ORGANISM: Artificial Sequence
<220> FEATURE:
<223> OTHER INFORMATION: synthetic peptide

<400> SEQUENCE: 16

Arg Ala Val Asn Ile Thr Ser Glu Asn Leu Ile Asp Asp Val Val Ser
1               5                   10                  15

Leu Ile Arg Gly
            20

<210> SEQ ID NO 17
<211> LENGTH: 22
<212> TYPE: PRT
<213> ORGANISM: Artificial Sequence
<220> FEATURE:
<223> OTHER INFORMATION: synthetic peptide

<400> SEQUENCE: 17

Lys Thr Asp Asn Ser Leu Leu Asp Gln Ala Leu Gln Asn Asp Thr Val
1               5                   10                  15

Phe Leu Asn Met Arg Gly
            20

<210> SEQ ID NO 18
<211> LENGTH: 21
<212> TYPE: PRT
<213> ORGANISM: Artificial Sequence
<220> FEATURE:
<223> OTHER INFORMATION: synthetic peptide

<400> SEQUENCE: 18

Lys Ser Leu Thr Phe Asn Glu Thr Tyr Gln Asp Ile Ser Glu Leu Val
1               5                   10                  15

Tyr Gly Ala Lys Leu
            20

<210> SEQ ID NO 19
<211> LENGTH: 22
<212> TYPE: PRT
<213> ORGANISM: Artificial Sequence
<220> FEATURE:

<223> OTHER INFORMATION: synthetic peptide

<400> SEQUENCE: 19

Arg Val Tyr Ile His Pro Phe His Leu Val Ile His Glu Ser Thr Cys
 1               5                  10                  15

Glu Gln Leu Ala Lys Ala
            20

<210> SEQ ID NO 20
<211> LENGTH: 15
<212> TYPE: PRT
<213> ORGANISM: Artificial Sequence
<220> FEATURE:
<223> OTHER INFORMATION: synthetic peptide

<400> SEQUENCE: 20

Lys Thr Lys Pro Arg Glu Glu Gln Phe Asn Ser Thr Phe Arg Val
 1               5                  10                  15

<210> SEQ ID NO 21
<211> LENGTH: 13
<212> TYPE: PRT
<213> ORGANISM: Artificial Sequence
<220> FEATURE:
<223> OTHER INFORMATION: synthetic peptide

<400> SEQUENCE: 21

Lys Pro Arg Glu Glu Gln Phe Asn Ser Thr Phe Arg Val
 1               5                  10

<210> SEQ ID NO 22
<211> LENGTH: 13
<212> TYPE: PRT
<213> ORGANISM: Artificial Sequence
<220> FEATURE:
<223> OTHER INFORMATION: synthetic peptide

<400> SEQUENCE: 22

Lys Tyr Lys Asn Asn Ser Asp Ile Ser Ser Thr Arg Gly
 1               5                  10

<210> SEQ ID NO 23
<211> LENGTH: 11
<212> TYPE: PRT
<213> ORGANISM: Artificial Sequence
<220> FEATURE:
<223> OTHER INFORMATION: synthetic peptide

<400> SEQUENCE: 23

Lys Thr Pro Leu Thr Ala Asn Ile Thr Lys Ser
 1               5                  10

<210> SEQ ID NO 24
<211> LENGTH: 24
<212> TYPE: PRT
<213> ORGANISM: Artificial Sequence
<220> FEATURE:
<223> OTHER INFORMATION: synthetic peptide

<400> SEQUENCE: 24

Arg Ala Asp Gly Thr Val Asn Gln Ile Glu Gly Glu Ala Thr Pro Val
 1               5                  10                  15

Asn Leu Thr Glu Pro Ala Lys Leu
            20

```
<210> SEQ ID NO 25
<211> LENGTH: 21
<212> TYPE: PRT
<213> ORGANISM: Artificial Sequence
<220> FEATURE:
<223> OTHER INFORMATION: synthetic peptide

<400> SEQUENCE: 25

Arg Val Leu Ser Asn Asn Ser Asp Ala Asn Leu Glu Leu Ile Asn Thr
 1               5                  10                  15

Trp Val Ala Lys Asn
            20

<210> SEQ ID NO 26
<211> LENGTH: 34
<212> TYPE: PRT
<213> ORGANISM: Artificial Sequence
<220> FEATURE:
<223> OTHER INFORMATION: synthetic peptide

<400> SEQUENCE: 26

Arg Ala Gly Glu Asn Asp Phe Ser Ile Met Tyr Ser Thr Arg Lys Arg
 1               5                  10                  15

Ser Ala Gln Leu Trp Leu Gly Pro Ala Ala Phe Ile Asn His Asp Cys
            20                  25                  30

Lys Pro

<210> SEQ ID NO 27
<211> LENGTH: 8
<212> TYPE: PRT
<213> ORGANISM: Artificial Sequence
<220> FEATURE:
<223> OTHER INFORMATION: synthetic peptide

<400> SEQUENCE: 27

Arg Phe Ser Ile Val Met Asn Glu
 1               5

<210> SEQ ID NO 28
<211> LENGTH: 13
<212> TYPE: PRT
<213> ORGANISM: Artificial Sequence
<220> FEATURE:
<223> OTHER INFORMATION: synthetic peptide

<400> SEQUENCE: 28

Leu Phe Leu Asn His Ser Glu Asn Ala Thr Ala Lys Asp
 1               5                  10

<210> SEQ ID NO 29
<211> LENGTH: 26
<212> TYPE: PRT
<213> ORGANISM: Artificial Sequence
<220> FEATURE:
<223> OTHER INFORMATION: synthetic peptide

<400> SEQUENCE: 29

Lys Met Val Ser His His Asn Leu Thr Thr Gly Ala Thr Leu Ile Asn
 1               5                  10                  15

Glu Gln Trp Leu Leu Thr Thr Ala Lys Asn
            20                  25

<210> SEQ ID NO 30
<211> LENGTH: 20
<212> TYPE: PRT
```

<213> ORGANISM: Artificial Sequence
<220> FEATURE:
<223> OTHER INFORMATION: synthetic peptide

<400> SEQUENCE: 30

Met Asn Asn Leu Ser Glu Asn Tyr Glu Asn Gln Gly Arg Leu Gln Val
 1               5                  10                  15
Tyr Met Asn Lys
            20

<210> SEQ ID NO 31
<211> LENGTH: 23
<212> TYPE: PRT
<213> ORGANISM: Artificial Sequence
<220> FEATURE:
<223> OTHER INFORMATION: synthetic peptide

<400> SEQUENCE: 31

Lys Val Gly Gln Leu Gln Leu Ser His Asn Leu Ser Leu Val Ile Leu
 1               5                  10                  15
Val Pro Gln Asn Leu Lys His
            20

<210> SEQ ID NO 32
<211> LENGTH: 21
<212> TYPE: PRT
<213> ORGANISM: Artificial Sequence
<220> FEATURE:
<223> OTHER INFORMATION: synthetic peptide

<400> SEQUENCE: 32

Arg Val Leu Ser Asn Asn Ser Asp Ala Asn Leu Glu Leu Ile Asn Thr
 1               5                  10                  15
Trp Val Ala Lys Asn
            20

<210> SEQ ID NO 33
<211> LENGTH: 26
<212> TYPE: PRT
<213> ORGANISM: Artificial Sequence
<220> FEATURE:
<223> OTHER INFORMATION: synthetic peptide

<400> SEQUENCE: 33

Lys Met Val Ser His His Asn Leu Thr Ile Gly Ala Thr Leu Ile Asn
 1               5                  10                  15
Glu Gln Trp Leu Leu Thr Thr Ala Lys Asn
            20                  25

<210> SEQ ID NO 34
<211> LENGTH: 27
<212> TYPE: PRT
<213> ORGANISM: Artificial Sequence
<220> FEATURE:
<223> OTHER INFORMATION: synthetic peptide

<400> SEQUENCE: 34

Lys Asn Leu Phe Leu Asn His Ser Glu Asn Ala Thr Ala Lys Asp Ile
 1               5                  10                  15
Ala Pro Thr Leu Thr Leu Tyr Val Gly Lys Lys
            20                  25

<210> SEQ ID NO 35
<211> LENGTH: 13

```
<212> TYPE: PRT
<213> ORGANISM: Artificial Sequence
<220> FEATURE:
<223> OTHER INFORMATION: synthetic peptide

<400> SEQUENCE: 35

Leu Phe Leu Asn His Ser Glu Asn Ala Thr Ala Lys Asp
 1               5                  10

<210> SEQ ID NO 36
<211> LENGTH: 16
<212> TYPE: PRT
<213> ORGANISM: Artificial Sequence
<220> FEATURE:
<223> OTHER INFORMATION: synthetic peptide

<400> SEQUENCE: 36

Lys Gly Ala Phe Ile Ser Asn Phe Ser Met Thr Val Asp Gly Lys Thr
 1               5                  10                  15

<210> SEQ ID NO 37
<211> LENGTH: 24
<212> TYPE: PRT
<213> ORGANISM: Artificial Sequence
<220> FEATURE:
<223> OTHER INFORMATION: synthetic peptide

<400> SEQUENCE: 37

Lys Ala Ala Leu Ala Ala Phe Asn Ala Gln Asn Asn Gly Ser Asn Phe
 1               5                  10                  15

Gln Leu Glu Glu Ile Ser Arg Ala
             20

<210> SEQ ID NO 38
<211> LENGTH: 26
<212> TYPE: PRT
<213> ORGANISM: Artificial Sequence
<220> FEATURE:
<223> OTHER INFORMATION: synthetic peptide

<400> SEQUENCE: 38

Lys Ile Leu Arg Gln Gln Gln His Leu Phe Gly Ser Asn Val Thr Asp
 1               5                  10                  15

Cys Ser Gly Asn Phe Cys Leu Phe Arg Ser
             20                  25

<210> SEQ ID NO 39
<211> LENGTH: 23
<212> TYPE: PRT
<213> ORGANISM: Artificial Sequence
<220> FEATURE:
<223> OTHER INFORMATION: synthetic peptide

<400> SEQUENCE: 39

Arg Gln Gln Gln His Leu Phe Gly Ser Asn Val Thr Asp Cys Ser Gly
 1               5                  10                  15

Asn Phe Cys Leu Phe Arg Ser
             20

<210> SEQ ID NO 40
<211> LENGTH: 16
<212> TYPE: PRT
<213> ORGANISM: Artificial Sequence
<220> FEATURE:
<223> OTHER INFORMATION: synthetic peptide
```

```
<400> SEQUENCE: 40

Gly Ser Asn Val Thr Asp Cys Ser Gly Asn Phe Cys Leu Phe Arg Ser
 1               5                  10                  15

<210> SEQ ID NO 41
<211> LENGTH: 23
<212> TYPE: PRT
<213> ORGANISM: Artificial Sequence
<220> FEATURE:
<223> OTHER INFORMATION: synthetic peptide

<400> SEQUENCE: 41

Arg Gln Gln Gln His Leu Phe Gly Ser Asn Val Thr Asp Cys Ser Gly
 1               5                  10                  15

Asn Phe Cys Leu Phe Arg Ser
            20

<210> SEQ ID NO 42
<211> LENGTH: 22
<212> TYPE: PRT
<213> ORGANISM: Artificial Sequence
<220> FEATURE:
<223> OTHER INFORMATION: synthetic peptide

<400> SEQUENCE: 42

Lys Met Leu Asn Thr Ser Ser Leu Leu Glu Gln Leu Asn Glu Gln Phe
 1               5                  10                  15

Asn Trp Val Ser Arg Leu
            20

<210> SEQ ID NO 43
<211> LENGTH: 16
<212> TYPE: PRT
<213> ORGANISM: Artificial Sequence
<220> FEATURE:
<223> OTHER INFORMATION: synthetic peptide

<400> SEQUENCE: 43

Arg Leu Ala Asn Leu Thr Gln Gly Glu Asp Gln Tyr Tyr Leu Arg Val
 1               5                  10                  15

<210> SEQ ID NO 44
<211> LENGTH: 29
<212> TYPE: PRT
<213> ORGANISM: Artificial Sequence
<220> FEATURE:
<223> OTHER INFORMATION: synthetic peptide

<400> SEQUENCE: 44

Lys Ala Lys Glu Asn Asp Glu Asn Cys Gly Pro Thr Thr Thr Val Phe
 1               5                  10                  15

Val Gly Asn Ile Ser Glu Lys Ala Ser Asp Met Leu Ile
            20                  25

<210> SEQ ID NO 45
<211> LENGTH: 19
<212> TYPE: PRT
<213> ORGANISM: Artificial Sequence
<220> FEATURE:
<223> OTHER INFORMATION: synthetic peptide

<400> SEQUENCE: 45

Arg Phe Ser Asp Gly Leu Glu Ser Asn Ser Ser Thr Gln Phe Glu Val
 1               5                  10                  15
```

-continued

Lys Lys Tyr

<210> SEQ ID NO 46
<211> LENGTH: 33
<212> TYPE: PRT
<213> ORGANISM: Artificial Sequence
<220> FEATURE:
<223> OTHER INFORMATION: synthetic peptide

<400> SEQUENCE: 46

Lys Ala Asp Thr His Asp Glu Ile Leu Glu Gly Leu Asn Phe Asn Leu
1 5 10 15

Thr Glu Ile Pro Glu Ala Gln Ile His Glu Gly Phe Gln Glu Leu Leu
20 25 30

Arg

<210> SEQ ID NO 47
<211> LENGTH: 34
<212> TYPE: PRT
<213> ORGANISM: Artificial Sequence
<220> FEATURE:
<223> OTHER INFORMATION: synthetic peptide

<400> SEQUENCE: 47

Lys Ala Asp Thr His Asp Glu Ile Leu Glu Gly Leu Asn Phe Asn Leu
1 5 10 15

Thr Glu Ile Pro Glu Ala Gln Ile His Glu Gly Phe Gln Glu Leu Leu
20 25 30

Arg Thr

<210> SEQ ID NO 48
<211> LENGTH: 32
<212> TYPE: PRT
<213> ORGANISM: Artificial Sequence
<220> FEATURE:
<223> OTHER INFORMATION: synthetic peptide

<400> SEQUENCE: 48

Arg Gln Leu Ala His Gln Ser Asn Ser Thr Asn Ile Phe Phe Ser Pro
1 5 10 15

Val Ser Ile Ala Thr Ala Phe Ala Met Leu Ser Leu Gly Thr Lys Ala
20 25 30

<210> SEQ ID NO 49
<211> LENGTH: 27
<212> TYPE: PRT
<213> ORGANISM: Artificial Sequence
<220> FEATURE:
<223> OTHER INFORMATION: synthetic peptide

<400> SEQUENCE: 49

Lys Thr Ile Asp Arg Leu Ala Gly Lys Pro Thr His Val Asn Val Ser
1 5 10 15

Val Val Met Ala Glu Val Asp Gly Thr Cys Tyr
20 25

<210> SEQ ID NO 50
<211> LENGTH: 29
<212> TYPE: PRT
<213> ORGANISM: Artificial Sequence
<220> FEATURE:
<223> OTHER INFORMATION: synthetic peptide

<400> SEQUENCE: 50
```
Arg Leu Ser Leu His Arg Pro Ala Leu Glu Asp Leu Leu Gly Ser
  1               5                  10                  15

Glu Ala Asn Leu Thr Cys Thr Leu Thr Gly Leu Arg Asp
                20                  25

<210> SEQ ID NO 51
<211> LENGTH: 45
<212> TYPE: PRT
<213> ORGANISM: Artificial Sequence
<220> FEATURE:
<223> OTHER INFORMATION: synthetic peptide

<400> SEQUENCE: 51

Met Pro Pro Thr Pro Val Thr Pro Val Thr Pro Thr Thr Pro Ala Leu
  1               5                  10                  15

Pro Ala Ile Pro Ile Ser Pro Pro Val Ser Ala Val Asn Lys Ser
                20                  25                  30

Gly Pro Ser Thr Val Ser Glu Pro Ala Lys Ser Ser
        35                  40                  45

<210> SEQ ID NO 52
<211> LENGTH: 21
<212> TYPE: PRT
<213> ORGANISM: Artificial Sequence
<220> FEATURE:
<223> OTHER INFORMATION: synthetic peptide

<400> SEQUENCE: 52

Arg Val Leu Ser Asn Asn Ser Asp Ala Asn Leu Glu Leu Ile Asn Thr
  1               5                  10                  15

Trp Val Ala Lys Asn
                20

<210> SEQ ID NO 53
<211> LENGTH: 33
<212> TYPE: PRT
<213> ORGANISM: Artificial Sequence
<220> FEATURE:
<223> OTHER INFORMATION: synthetic peptide

<400> SEQUENCE: 53

Lys Ala His Gly Thr Ser Ser Tyr Thr Pro Asp Lys Ser Ser Phe Asn
  1               5                  10                  15

Leu Ala Thr Val Val Ala Glu Thr Leu Gly Leu Gly Val Gln Glu Glu
                20                  25                  30

Ser

<210> SEQ ID NO 54
<211> LENGTH: 32
<212> TYPE: PRT
<213> ORGANISM: Artificial Sequence
<220> FEATURE:
<223> OTHER INFORMATION: synthetic peptide

<400> SEQUENCE: 54

Arg Gly His Leu Ser Glu Glu Pro Glu Asn Ile Asn Thr Pro Thr
  1               5                  10                  15

Arg Leu Thr Pro Gln Leu Gln Met Lys Pro Met Ser Asn Arg Glu Arg
                20                  25                  30

<210> SEQ ID NO 55
<211> LENGTH: 22
```

```
<212> TYPE: PRT
<213> ORGANISM: Artificial Sequence
<220> FEATURE:
<223> OTHER INFORMATION: synthetic peptide

<400> SEQUENCE: 55

Arg His Thr Phe Met Gly Val Val Ser Leu Gly Ser Pro Ser Gly Glu
1               5                   10                  15

Val Ser His Pro Arg Lys
            20

<210> SEQ ID NO 56
<211> LENGTH: 16
<212> TYPE: PRT
<213> ORGANISM: Artificial Sequence
<220> FEATURE:
<223> OTHER INFORMATION: synthetic peptide

<400> SEQUENCE: 56

Gly Ser Asn Val Thr Asp Cys Ser Gly Asn Phe Cys Leu Phe Arg Ser
1               5                   10                  15

<210> SEQ ID NO 57
<211> LENGTH: 22
<212> TYPE: PRT
<213> ORGANISM: Artificial Sequence
<220> FEATURE:
<223> OTHER INFORMATION: synthetic peptide

<400> SEQUENCE: 57

Lys Met Leu Asn Thr Ser Ser Leu Leu Glu Gln Leu Asn Glu Gln Phe
1               5                   10                  15

Asn Trp Val Ser Arg Leu
            20

<210> SEQ ID NO 58
<211> LENGTH: 37
<212> TYPE: PRT
<213> ORGANISM: Artificial Sequence
<220> FEATURE:
<223> OTHER INFORMATION: synthetic peptide

<400> SEQUENCE: 58

Gly Gly Gly Ser Gly Gly Gly Gly Ala Pro Ser Gly Gly Ser Gly His
1               5                   10                  15

Ser Gly Gly Pro Ser Ser Cys Gly Gly Ala Pro Ser Thr Ser Arg Ser
            20                  25                  30

Arg Pro Ser Arg Ile
        35

<210> SEQ ID NO 59
<211> LENGTH: 34
<212> TYPE: PRT
<213> ORGANISM: Artificial Sequence
<220> FEATURE:
<223> OTHER INFORMATION: synthetic peptide

<400> SEQUENCE: 59

Lys Ala Asp Thr His Asp Glu Ile Leu Glu Gly Leu Asn Phe Asn Leu
1               5                   10                  15

Thr Glu Ile Pro Glu Ala Gln Ile His Glu Gly Phe Gln Glu Leu Leu
            20                  25                  30

Arg Thr
```

<210> SEQ ID NO 60
<211> LENGTH: 33
<212> TYPE: PRT
<213> ORGANISM: Artificial Sequence
<220> FEATURE:
<223> OTHER INFORMATION: synthetic peptide

<400> SEQUENCE: 60

Lys Tyr Leu Gly Asn Ala Thr Ala Ile Phe Phe Leu Pro Asp Glu Gly
1               5                   10                  15

Lys Leu Gln His Leu Glu Asn Glu Leu Thr His Asp Ile Ile Thr Lys
            20                  25                  30

Phe

<210> SEQ ID NO 61
<211> LENGTH: 33
<212> TYPE: PRT
<213> ORGANISM: Artificial Sequence
<220> FEATURE:
<223> OTHER INFORMATION: synthetic peptide

<400> SEQUENCE: 61

Lys Ala Asp Thr His Asp Glu Ile Leu Glu Gly Leu Asn Phe Asn Leu
1               5                   10                  15

Thr Glu Ile Pro Glu Ala Gln Ile His Glu Gly Phe Gln Glu Leu Leu
            20                  25                  30

Arg

<210> SEQ ID NO 62
<211> LENGTH: 12
<212> TYPE: PRT
<213> ORGANISM: Artificial Sequence
<220> FEATURE:
<223> OTHER INFORMATION: synthetic peptide

<400> SEQUENCE: 62

Lys Ala Asp Leu Ser Gly Ile Thr Gly Ala Arg Asn
1               5                   10

<210> SEQ ID NO 63
<211> LENGTH: 13
<212> TYPE: PRT
<213> ORGANISM: Artificial Sequence
<220> FEATURE:
<223> OTHER INFORMATION: synthetic peptide

<400> SEQUENCE: 63

Lys Ala Ile Gly Tyr Leu Asn Thr Gly Tyr Gln Arg Gln
1               5                   10

<210> SEQ ID NO 64
<211> LENGTH: 14
<212> TYPE: PRT
<213> ORGANISM: Homo sapiens

<400> SEQUENCE: 64

Lys Leu His Val Thr Leu Tyr Asn Cys Ser Phe Gly Arg Ser
1               5                   10

<210> SEQ ID NO 65
<211> LENGTH: 16
<212> TYPE: PRT
<213> ORGANISM: Homo sapiens

```
<400> SEQUENCE: 65

Arg Ser Ile Asn Val Thr Gly Gln Gly Phe Ser Leu Ile Gln Arg Phe
 1               5                  10                  15

<210> SEQ ID NO 66
<211> LENGTH: 25
<212> TYPE: PRT
<213> ORGANISM: Homo sapiens

<400> SEQUENCE: 66

Arg Thr Glu Ala Gly Ala Phe Glu Tyr Val Pro Asp Pro Thr Phe Glu
 1               5                  10                  15

Asn Phe Thr Gly Gly Val Lys Lys Gln
            20                  25

<210> SEQ ID NO 67
<211> LENGTH: 16
<212> TYPE: PRT
<213> ORGANISM: Homo sapiens

<400> SEQUENCE: 67

Arg Ala Gly Pro Asn Gly Thr Leu Phe Val Ala Asp Ala Tyr Lys Gly
 1               5                  10                  15

<210> SEQ ID NO 68
<211> LENGTH: 29
<212> TYPE: PRT
<213> ORGANISM: Homo sapiens

<400> SEQUENCE: 68

Lys Leu Leu Leu Ser Ser Glu Thr Pro Ile Glu Gly Lys Asn Met Ser
 1               5                  10                  15

Phe Val Asn Asp Leu Thr Val Thr Gln Asp Gly Arg Lys
            20                  25

<210> SEQ ID NO 69
<211> LENGTH: 21
<212> TYPE: PRT
<213> ORGANISM: Homo sapiens

<400> SEQUENCE: 69

Arg Tyr His Tyr Asn Gly Ser Leu Met Asp Gly Thr Leu Phe Asp Ser
 1               5                  10                  15

Ser Tyr Ser Arg Asn
            20

<210> SEQ ID NO 70
<211> LENGTH: 21
<212> TYPE: PRT
<213> ORGANISM: Homo sapiens

<400> SEQUENCE: 70

Arg Tyr His Tyr Asn Gly Thr Phe Leu Asp Gly Thr Leu Phe Asp Ser
 1               5                  10                  15

Ser His Asn Arg Met
            20

<210> SEQ ID NO 71
<211> LENGTH: 21
<212> TYPE: PRT
<213> ORGANISM: Homo sapiens

<400> SEQUENCE: 71
```

```
Arg Tyr His Tyr Asn Gly Thr Leu Leu Asp Gly Thr Leu Phe Asp Ser
1               5                   10                  15

Ser Tyr Ser Arg Asn
            20
```

<210> SEQ ID NO 72
<211> LENGTH: 18
<212> TYPE: PRT
<213> ORGANISM: Homo sapiens

<400> SEQUENCE: 72

```
Arg Thr Ala Leu Phe Pro Asp Leu Leu Ala Gln Gly Asn Ala Ser Leu
1               5                   10                  15

Arg Leu
```

<210> SEQ ID NO 73
<211> LENGTH: 17
<212> TYPE: PRT
<213> ORGANISM: Homo sapiens

<400> SEQUENCE: 73

```
Arg Leu Leu Ala Asn Ser Ser Met Leu Gly Glu Gly Gln Val Leu Arg
1               5                   10                  15

Ser
```

<210> SEQ ID NO 74
<211> LENGTH: 24
<212> TYPE: PRT
<213> ORGANISM: Homo sapiens

<400> SEQUENCE: 74

```
Lys Gln Val Ala Leu Gln Thr Phe Gly Asn Gln Thr Thr Ile Ile Pro
1               5                   10                  15

Ala Gly Gly Ala Gly Tyr Lys Val
            20
```

<210> SEQ ID NO 75
<211> LENGTH: 23
<212> TYPE: PRT
<213> ORGANISM: Homo sapiens

<400> SEQUENCE: 75

```
Arg Phe Thr Phe Thr Ser His Thr Pro Gly Glu His Gln Ile Cys Leu
1               5                   10                  15

His Ser Asn Ser Thr Lys Phe
            20
```

<210> SEQ ID NO 76
<211> LENGTH: 14
<212> TYPE: PRT
<213> ORGANISM: Homo sapiens

<400> SEQUENCE: 76

```
Lys Ile Phe Ile Phe Asn Gln Thr Gly Ile Glu Ala Lys Lys
1               5                   10
```

<210> SEQ ID NO 77
<211> LENGTH: 14
<212> TYPE: PRT
<213> ORGANISM: Homo sapiens

<400> SEQUENCE: 77

```
Lys Ala Val Leu Val Asn Asn Ile Thr Thr Gly Glu Arg Leu
1               5                   10
```

<210> SEQ ID NO 78
<211> LENGTH: 19
<212> TYPE: PRT
<213> ORGANISM: Homo sapiens

<400> SEQUENCE: 78

```
Arg Leu Gln Gln Asp Val Leu Gln Phe Gln Lys Asn Gln Thr Asn Leu
1               5                   10                  15

Glu Arg Lys
```

<210> SEQ ID NO 79
<211> LENGTH: 23
<212> TYPE: PRT
<213> ORGANISM: Homo sapiens

<400> SEQUENCE: 79

```
Lys Val Val Met Asp Ile Pro Tyr Glu Leu Trp Asn Glu Thr Ser Ala
1               5                   10                  15

Glu Val Ala Asp Leu Lys Lys
            20
```

<210> SEQ ID NO 80
<211> LENGTH: 18
<212> TYPE: PRT
<213> ORGANISM: Homo sapiens

<400> SEQUENCE: 80

```
Lys Leu Asn Ile Thr Asn Ile Trp Val Leu Asp Tyr Phe Gly Gly Pro
1               5                   10                  15

Lys Ile
```

<210> SEQ ID NO 81
<211> LENGTH: 23
<212> TYPE: PRT
<213> ORGANISM: Homo sapiens

<400> SEQUENCE: 81

```
Lys Tyr His Tyr Asn Ala Ser Leu Leu Asp Gly Thr Leu Leu Asp Ser
1               5                   10                  15

Thr Trp Asn Leu Gly Lys Thr
            20
```

<210> SEQ ID NO 82
<211> LENGTH: 34
<212> TYPE: PRT
<213> ORGANISM: Homo sapiens

<400> SEQUENCE: 82

```
Arg Lys Thr Thr Trp Leu Gln Ala Ala Ser Leu Leu Phe Val Asp Asn
1               5                   10                  15

Pro Val Gly Thr Gly Phe Ser Tyr Val Asn Gly Ser Gly Ala Tyr Ala
            20                  25                  30

Lys Asp
```

<210> SEQ ID NO 83
<211> LENGTH: 32
<212> TYPE: PRT
<213> ORGANISM: Homo sapiens -continued

```
<400> SEQUENCE: 83

Arg Cys Phe Ala Thr Thr Tyr Tyr Leu Ser Glu Gly Gly Gly Leu Ile
1               5                   10                  15

Phe Arg Asn Val Thr Gly Glu Pro Asn Cys Arg Pro Pro Thr Arg Gly
            20                  25                  30

<210> SEQ ID NO 84
<211> LENGTH: 21
<212> TYPE: PRT
<213> ORGANISM: Homo sapiens

<400> SEQUENCE: 84

Arg Tyr His Tyr Asn Gly Thr Leu Leu Asp Gly Thr Ser Phe Asp Thr
1               5                   10                  15

Ser Tyr Ser Lys Gly
            20

<210> SEQ ID NO 85
<211> LENGTH: 22
<212> TYPE: PRT
<213> ORGANISM: Homo sapiens

<400> SEQUENCE: 85

Arg Gly Ile Leu Asn Ala Thr Ile Ser Val Ala Glu Ile Asn His Pro
1               5                   10                  15

Val Thr Thr Tyr Lys Thr
            20

<210> SEQ ID NO 86
<211> LENGTH: 24
<212> TYPE: PRT
<213> ORGANISM: Homo sapiens

<400> SEQUENCE: 86

Arg Gly Leu Val Met Asn Tyr Pro His Ile Thr Asn Leu Thr Asn Leu
1               5                   10                  15

Gly Gln Ser Thr Glu Tyr Arg His
            20

<210> SEQ ID NO 87
<211> LENGTH: 22
<212> TYPE: PRT
<213> ORGANISM: Homo sapiens

<400> SEQUENCE: 87

Arg Leu Leu Asn Thr Thr Asp Val Tyr Leu Leu Pro Ser Leu Asn Pro
1               5                   10                  15

Asp Gly Phe Glu Arg Ala
            20

<210> SEQ ID NO 88
<211> LENGTH: 15
<212> TYPE: PRT
<213> ORGANISM: Homo sapiens

<400> SEQUENCE: 88

Arg Ala Leu Gly Phe Glu Asn Ala Thr Gln Ala Leu Gly Arg Ala
1               5                   10                  15

<210> SEQ ID NO 89
<211> LENGTH: 22
```

```
<212> TYPE: PRT
<213> ORGANISM: Homo sapiens

<400> SEQUENCE: 89

Arg Val Phe Pro Tyr Ile Ser Val Met Val Asn Asn Gly Ser Leu Ser
1               5                   10                  15
Tyr Asp His Ser Lys Asp
            20

<210> SEQ ID NO 90
<211> LENGTH: 33
<212> TYPE: PRT
<213> ORGANISM: Homo sapiens

<400> SEQUENCE: 90

Arg Tyr His Tyr Asn Cys Ser Leu Leu Asp Gly Thr Gln Leu Phe Thr
1               5                   10                  15
Ser His Asp Tyr Gly Ala Pro Gln Glu Ala Thr Leu Gly Ala Asn Lys
            20                  25                  30
Val

<210> SEQ ID NO 91
<211> LENGTH: 19
<212> TYPE: PRT
<213> ORGANISM: Homo sapiens

<400> SEQUENCE: 91

Arg Tyr Ser Leu Asn Val Thr Tyr Asn Tyr Pro Val His Tyr Phe Asp
1               5                   10                  15
Gly Arg Lys

<210> SEQ ID NO 92
<211> LENGTH: 22
<212> TYPE: PRT
<213> ORGANISM: Homo sapiens

<400> SEQUENCE: 92

Arg Asp Ile Glu Asn Leu Lys Asp Ala Ser Ser Phe Leu Ala Glu Trp
1               5                   10                  15
Gln Asn Ile Thr Lys Gly
            20

<210> SEQ ID NO 93
<211> LENGTH: 24
<212> TYPE: PRT
<213> ORGANISM: Homo sapiens

<400> SEQUENCE: 93

Arg Leu Leu Ile Ala Gly Thr Asn Ser Ser Asp Leu Gln Gln Ile Leu
1               5                   10                  15
Ser Leu Leu Glu Ser Asn Lys Asp
            20

<210> SEQ ID NO 94
<211> LENGTH: 15
<212> TYPE: PRT
<213> ORGANISM: Homo sapiens

<400> SEQUENCE: 94

Lys Ser Leu Val Thr Gln Tyr Leu Asn Ala Thr Gly Asn Arg Trp
1               5                   10                  15
```

<210> SEQ ID NO 95
<211> LENGTH: 24
<212> TYPE: PRT
<213> ORGANISM: Homo sapiens

<400> SEQUENCE: 95

Lys Ile Leu Ala Pro Ala Tyr Phe Ile Leu Gly Gly Asn Gln Ser Gly
1               5                   10                  15

Glu Gly Cys Val Ile Thr Arg Asp
            20

<210> SEQ ID NO 96
<211> LENGTH: 15
<212> TYPE: PRT
<213> ORGANISM: Homo sapiens

<400> SEQUENCE: 96

Arg Thr Val Leu Glu Asn Ser Thr Ser Tyr Glu Glu Ala Lys Asn
1               5                   10                  15

<210> SEQ ID NO 97
<211> LENGTH: 22
<212> TYPE: PRT
<213> ORGANISM: Homo sapiens

<400> SEQUENCE: 97

Arg Phe Lys Leu Glu Trp Leu Gly Asn Cys Ser Gly Leu Asn Asp Glu
1               5                   10                  15

Thr Tyr Gly Tyr Lys Glu
            20

<210> SEQ ID NO 98
<211> LENGTH: 23
<212> TYPE: PRT
<213> ORGANISM: Homo sapiens

<400> SEQUENCE: 98

Arg Val Leu Gly Phe Lys Pro Lys Pro Lys Asn Glu Ser Leu Glu
1               5                   10                  15

Thr Tyr Pro Val Met Lys Tyr
            20

<210> SEQ ID NO 99
<211> LENGTH: 22
<212> TYPE: PRT
<213> ORGANISM: Homo sapiens

<400> SEQUENCE: 99

Lys Tyr Leu Gln Pro Leu Leu Ala Val Gln Phe Thr Asn Leu Thr Met
1               5                   10                  15

Asp Thr Glu Ile Arg Ile
            20

<210> SEQ ID NO 100
<211> LENGTH: 25
<212> TYPE: PRT
<213> ORGANISM: Homo sapiens

<400> SEQUENCE: 100

Lys Leu His Val Gly Tyr Leu Gln Pro Leu Val Ala Val Gln Val Ser
1               5                   10                  15

Phe Ala Pro Asn Asn Thr Gly Lys Glu

-continued

<210> SEQ ID NO 101
<211> LENGTH: 32
<212> TYPE: PRT
<213> ORGANISM: Homo sapiens

<400> SEQUENCE: 101

Lys Leu His Val Gly Tyr Leu Gln Pro Leu Val Ala Val Gln Val Ser
1               5                   10                  15

Phe Ala Pro Asn Asn Thr Gly Lys Glu Val Thr Val Glu Cys Lys Ile
            20                  25                  30

<210> SEQ ID NO 102
<211> LENGTH: 20
<212> TYPE: PRT
<213> ORGANISM: Homo sapiens

<400> SEQUENCE: 102

Lys Ile Leu Leu Thr Cys Ser Leu Asn Asp Ser Ala Thr Glu Val Thr
1               5                   10                  15

Gly His Arg Trp
            20

<210> SEQ ID NO 103
<211> LENGTH: 18
<212> TYPE: PRT
<213> ORGANISM: Homo sapiens

<400> SEQUENCE: 103

Lys Ile Thr Asp Ser Glu Asp Lys Ala Leu Met Asn Gly Ser Glu Ser
1               5                   10                  15

Arg Phe

<210> SEQ ID NO 104
<211> LENGTH: 22
<212> TYPE: PRT
<213> ORGANISM: Homo sapiens

<400> SEQUENCE: 104

Arg Leu Leu Asp Ala Glu Asn Lys Val Val Ala Asn Gly Thr Gly Thr
1               5                   10                  15

Gln Gly Gln Leu Lys Val
            20

<210> SEQ ID NO 105
<211> LENGTH: 15
<212> TYPE: PRT
<213> ORGANISM: Homo sapiens

<400> SEQUENCE: 105

Lys Val Val Ala Asn Gly Thr Gly Thr Gln Gly Gln Leu Lys Val
1               5                   10                  15

<210> SEQ ID NO 106
<211> LENGTH: 23
<212> TYPE: PRT
<213> ORGANISM: Homo sapiens

<400> SEQUENCE: 106

Lys Ile Ile Ile Ser Pro Glu Glu Asn Val Thr Leu Thr Cys Thr Ala
1               5                   10                  15

-continued

```
Glu Asn Gln Leu Glu Arg Thr
            20

<210> SEQ ID NO 107
<211> LENGTH: 21
<212> TYPE: PRT
<213> ORGANISM: Homo sapiens

<400> SEQUENCE: 107

Lys Leu Gly Asp Cys Ile Ser Glu Asp Ser Tyr Pro Asp Gly Asn Ile
1               5                   10                  15

Thr Trp Tyr Arg Asn
            20

<210> SEQ ID NO 108
<211> LENGTH: 17
<212> TYPE: PRT
<213> ORGANISM: Homo sapiens

<400> SEQUENCE: 108

Arg Leu Asn Leu Ser Glu Asn Tyr Thr Leu Ser Ile Ser Asn Ala Arg
1               5                   10                  15

Ile

<210> SEQ ID NO 109
<211> LENGTH: 28
<212> TYPE: PRT
<213> ORGANISM: Homo sapiens

<400> SEQUENCE: 109

Arg Thr Val Asn Ser Leu Asn Val Ser Ala Ile Ser Ile Pro Glu His
1               5                   10                  15

Asp Glu Ala Asp Glu Ile Ser Asp Glu Asn Arg Glu
            20                  25

<210> SEQ ID NO 110
<211> LENGTH: 30
<212> TYPE: PRT
<213> ORGANISM: Homo sapiens

<400> SEQUENCE: 110

Arg Thr Val Asn Ser Leu Asn Val Ser Ala Ile Ser Ile Pro Glu His
1               5                   10                  15

Asp Glu Ala Asp Glu Ile Ser Asp Glu Asn Arg Glu Lys Val
            20                  25                  30

<210> SEQ ID NO 111
<211> LENGTH: 12
<212> TYPE: PRT
<213> ORGANISM: Homo sapiens

<400> SEQUENCE: 111

Lys Gly Ser Leu Ser Tyr Leu Asn Val Thr Arg Lys
1               5                   10

<210> SEQ ID NO 112
<211> LENGTH: 15
<212> TYPE: PRT
<213> ORGANISM: Homo sapiens

<400> SEQUENCE: 112

Lys Tyr Tyr Lys Gly Ser Leu Ser Tyr Leu Asn Val Thr Arg Lys
1               5                   10                  15
```

```
<210> SEQ ID NO 113
<211> LENGTH: 16
<212> TYPE: PRT
<213> ORGANISM: Homo sapiens

<400> SEQUENCE: 113

Lys Tyr Ser Val Ala Asn Asp Thr Gly Phe Val Asp Ile Pro Lys Gln
 1               5                  10                  15

<210> SEQ ID NO 114
<211> LENGTH: 20
<212> TYPE: PRT
<213> ORGANISM: Homo sapiens

<400> SEQUENCE: 114

Arg Gln Gln Met Glu Asn Tyr Pro Lys Asn Asn His Thr Ala Ser Ile
 1               5                  10                  15

Leu Asp Arg Met
            20

<210> SEQ ID NO 115
<211> LENGTH: 22
<212> TYPE: PRT
<213> ORGANISM: Homo sapiens

<400> SEQUENCE: 115

Lys Met Leu Asn Thr Ser Ser Leu Leu Glu Gln Leu Asn Glu Gln Phe
 1               5                  10                  15

Asn Trp Val Ser Arg Leu
            20

<210> SEQ ID NO 116
<211> LENGTH: 30
<212> TYPE: PRT
<213> ORGANISM: Homo sapiens

<400> SEQUENCE: 116

Lys Gly His His Val Ser Gln Glu Pro Trp Asn Ser Ser Ile Thr Leu
 1               5                  10                  15

Thr Ser Gln Ala Gly Ala Val Phe Gln Ser Phe Ala Lys Phe
            20                  25                  30

<210> SEQ ID NO 117
<211> LENGTH: 31
<212> TYPE: PRT
<213> ORGANISM: Homo sapiens

<400> SEQUENCE: 117

Lys Asp Thr Gly Glu Leu Asn Val Thr Ser Ile Leu Asp Arg Glu Glu
 1               5                  10                  15

Thr Pro Phe Phe Leu Leu Thr Gly Tyr Ala Leu Asp Ala Arg Gly
            20                  25                  30

<210> SEQ ID NO 118
<211> LENGTH: 25
<212> TYPE: PRT
<213> ORGANISM: Homo sapiens

<400> SEQUENCE: 118

Lys His Asn Asn Asp Thr Gln His Ile Trp Glu Ser Asp Ser Asn Glu
 1               5                  10                  15
```

-continued

```
Phe Ser Val Ile Ala Asp Pro Arg Gly
            20              25

<210> SEQ ID NO 119
<211> LENGTH: 22
<212> TYPE: PRT
<213> ORGANISM: Homo sapiens

<400> SEQUENCE: 119

Lys Tyr Leu Asn Phe Val Lys Gly Val Val Asp Ser Asp Asp Leu Pro
1               5                   10                  15

Leu Asn Val Ser Arg Glu
            20

<210> SEQ ID NO 120
<211> LENGTH: 24
<212> TYPE: PRT
<213> ORGANISM: Homo sapiens

<400> SEQUENCE: 120

Lys Phe Leu Tyr Asn Phe Thr Gln Ile Pro His Leu Ala Gly Thr Glu
1               5                   10                  15

Gln Asn Phe Gln Leu Ala Lys Gln
            20

<210> SEQ ID NO 121
<211> LENGTH: 20
<212> TYPE: PRT
<213> ORGANISM: Homo sapiens

<400> SEQUENCE: 121

Arg Gly Val Ala Tyr Ile Asn Ala Asp Ser Ser Ile Glu Gly Asn Tyr
1               5                   10                  15

Thr Leu Arg Val
            20

<210> SEQ ID NO 122
<211> LENGTH: 24
<212> TYPE: PRT
<213> ORGANISM: Homo sapiens

<400> SEQUENCE: 122

Lys Thr Tyr Ser Val Ser Phe Asp Ser Leu Phe Ser Ala Val Lys Asn
1               5                   10                  15

Phe Thr Glu Ile Ala Ser Lys Phe
            20

<210> SEQ ID NO 123
<211> LENGTH: 18
<212> TYPE: PRT
<213> ORGANISM: Homo sapiens

<400> SEQUENCE: 123

Arg Val Asp Cys Thr Pro Leu Met Tyr Ser Leu Val His Asn Leu Thr
1               5                   10                  15

Lys Glu

<210> SEQ ID NO 124
<211> LENGTH: 19
<212> TYPE: PRT
<213> ORGANISM: Homo sapiens

<400> SEQUENCE: 124
```

```
Lys Val Pro Tyr Asn Val Gly Pro Gly Phe Thr Gly Asn Phe Ser Thr
 1               5                  10                  15

Gln Lys Val

<210> SEQ ID NO 125
<211> LENGTH: 18
<212> TYPE: PRT
<213> ORGANISM: Homo sapiens

<400> SEQUENCE: 125

Lys Thr Pro Met Thr Asn Ser Ser Ile Gln Phe Leu Asp Asn Ala Phe
 1               5                  10                  15

Arg Lys

<210> SEQ ID NO 126
<211> LENGTH: 13
<212> TYPE: PRT
<213> ORGANISM: Homo sapiens

<400> SEQUENCE: 126

Lys Tyr Tyr Asn Tyr Thr Leu Ser Ile Asn Gly Lys Ala
 1               5                  10

<210> SEQ ID NO 127
<211> LENGTH: 17
<212> TYPE: PRT
<213> ORGANISM: Homo sapiens

<400> SEQUENCE: 127

Arg Asp Leu Gly Pro Thr Leu Ala Asn Ser Thr His His Asn Val Arg
 1               5                  10                  15

Leu

<210> SEQ ID NO 128
<211> LENGTH: 28
<212> TYPE: PRT
<213> ORGANISM: Homo sapiens

<400> SEQUENCE: 128

Arg Met Glu Leu Ser Met Gly Pro Ile Gln Ala Asn His Thr Gly Thr
 1               5                  10                  15

Gly Leu Leu Leu Thr Leu Gln Pro Glu Gln Lys Phe
                20                  25

<210> SEQ ID NO 129
<211> LENGTH: 29
<212> TYPE: PRT
<213> ORGANISM: Homo sapiens

<400> SEQUENCE: 129

Arg Arg Met Glu Leu Ser Met Gly Pro Ile Gln Ala Asn His Thr Gly
 1               5                  10                  15

Thr Gly Leu Leu Leu Thr Leu Gln Pro Glu Gln Lys Phe
                20                  25

<210> SEQ ID NO 130
<211> LENGTH: 26
<212> TYPE: PRT
<213> ORGANISM: Homo sapiens

<400> SEQUENCE: 130
```

-continued

Arg Thr Tyr Thr Tyr Ala Asp Thr Pro Asp Asp Phe Gln Leu His Asn
1               5                   10                  15

Phe Ser Leu Pro Glu Glu Asp Thr Lys Leu
            20                  25

<210> SEQ ID NO 131
<211> LENGTH: 24
<212> TYPE: PRT
<213> ORGANISM: Homo sapiens

<400> SEQUENCE: 131

Arg Asp Ile Val Gly Asn Leu Thr Glu Leu Glu Ser Glu Asp Ile Gln
1               5                   10                  15

Ile Glu Ala Leu Leu Met Arg Ala
            20

<210> SEQ ID NO 132
<211> LENGTH: 25
<212> TYPE: PRT
<213> ORGANISM: Homo sapiens

<400> SEQUENCE: 132

Lys Leu Asp Ser Phe Gly Pro Ile Asn Pro Thr Leu Asn Thr Thr Tyr
1               5                   10                  15

Ser Phe Leu Thr Thr Phe Phe Lys Glu
            20                  25

<210> SEQ ID NO 133
<211> LENGTH: 24
<212> TYPE: PRT
<213> ORGANISM: Homo sapiens

<400> SEQUENCE: 133

Arg Thr Ala Ala Asp Thr Thr Gly Leu Gln Pro Ile Leu Asn Gln Phe
1               5                   10                  15

Thr Pro Ala Asn Ile Ser Arg Gln
            20

<210> SEQ ID NO 134
<211> LENGTH: 31
<212> TYPE: PRT
<213> ORGANISM: Homo sapiens

<400> SEQUENCE: 134

Arg Leu Thr Gly Ser Asp Val Asn Leu Leu Ala Glu Asn Leu Leu Ser
1               5                   10                  15

Pro Glu Asp Met Val Leu Phe His Asn Leu Thr Gln Pro Arg Gly
            20                  25                  30

<210> SEQ ID NO 135
<211> LENGTH: 11
<212> TYPE: PRT
<213> ORGANISM: Homo sapiens

<400> SEQUENCE: 135

Lys Leu Leu Asn Asn Leu Thr Ser Ile Lys Ile
1               5                   10

<210> SEQ ID NO 136
<211> LENGTH: 12
<212> TYPE: PRT
<213> ORGANISM: Homo sapiens

```
<400> SEQUENCE: 136

Arg Gly His Thr Leu Thr Leu Asn Phe Thr Arg Asn
 1               5                  10

<210> SEQ ID NO 137
<211> LENGTH: 22
<212> TYPE: PRT
<213> ORGANISM: Homo sapiens

<400> SEQUENCE: 137

Lys Ser Gly Pro Lys Asn Met Thr Phe Asp Leu Pro Ser Asp Ala Thr
 1               5                  10                  15

Val Val Leu Asn Arg Ser
            20

<210> SEQ ID NO 138
<211> LENGTH: 19
<212> TYPE: PRT
<213> ORGANISM: Homo sapiens

<400> SEQUENCE: 138

Lys Ile Ala Val Gln Phe Gly Pro Gly Phe Ser Trp Ile Ala Asn Phe
 1               5                  10                  15

Thr Lys Ala

<210> SEQ ID NO 139
<211> LENGTH: 10
<212> TYPE: PRT
<213> ORGANISM: Homo sapiens

<400> SEQUENCE: 139

Lys Trp Gln Met Asn Phe Thr Val Arg Tyr
 1               5                  10

<210> SEQ ID NO 140
<211> LENGTH: 17
<212> TYPE: PRT
<213> ORGANISM: Homo sapiens

<400> SEQUENCE: 140

Arg Thr Gln Asn Phe Thr Leu Leu Val Gln Gly Ser Pro Glu Leu Lys
 1               5                  10                  15

Thr

<210> SEQ ID NO 141
<211> LENGTH: 17
<212> TYPE: PRT
<213> ORGANISM: Homo sapiens

<400> SEQUENCE: 141

Arg Gly Val Phe Ile Thr Asn Glu Thr Gly Gln Pro Leu Ile Gly Lys
 1               5                  10                  15

Val

<210> SEQ ID NO 142
<211> LENGTH: 20
<212> TYPE: PRT
<213> ORGANISM: Homo sapiens

<400> SEQUENCE: 142

Lys Cys Asn Met Ile Asn Gly Thr Asp Gly Asp Ser Phe His Pro Leu
 1               5                  10                  15
```

Ile Thr Lys Asp
            20

<210> SEQ ID NO 143
<211> LENGTH: 19
<212> TYPE: PRT
<213> ORGANISM: Homo sapiens

<400> SEQUENCE: 143

Arg Thr Met Val Phe Pro Val Met Tyr Leu Asn Glu Ser Val His Ile
1               5                   10                  15

Asp Lys Glu

<210> SEQ ID NO 144
<211> LENGTH: 24
<212> TYPE: PRT
<213> ORGANISM: Homo sapiens

<400> SEQUENCE: 144

Arg Thr Met Val Phe Pro Val Met Tyr Leu Asn Glu Ser Val His Ile
1               5                   10                  15

Asp Lys Glu Thr Ala Ser Arg Leu
            20

<210> SEQ ID NO 145
<211> LENGTH: 26
<212> TYPE: PRT
<213> ORGANISM: Homo sapiens

<400> SEQUENCE: 145

Arg Leu Glu His Gln Phe Ala Val Gly Glu Asp Ser Gly Arg Asn Leu
1               5                   10                  15

Ser Ala Pro Val Thr Leu Asn Leu Arg Asp
            20                  25

<210> SEQ ID NO 146
<211> LENGTH: 32
<212> TYPE: PRT
<213> ORGANISM: Homo sapiens

<400> SEQUENCE: 146

Arg Ala Thr Leu Ile Thr Phe Leu Cys Asp Arg Asp Ala Gly Val Gly
1               5                   10                  15

Phe Pro Glu Tyr Gln Glu Glu Asp Asn Ser Thr Tyr Asn Phe Arg Trp
            20                  25                  30

<210> SEQ ID NO 147
<211> LENGTH: 29
<212> TYPE: PRT
<213> ORGANISM: Homo sapiens

<400> SEQUENCE: 147

Arg His Gly Asn Leu Tyr Asp Leu Lys Pro Leu Gly Leu Asn Asp Thr
1               5                   10                  15

Ile Val Ser Ala Gly Glu Tyr Thr Tyr Tyr Phe Arg Val
            20                  25

<210> SEQ ID NO 148
<211> LENGTH: 23
<212> TYPE: PRT
<213> ORGANISM: Homo sapiens

```
<400> SEQUENCE: 148

Lys Ile Lys Thr Asn Ile Thr Leu Val Cys Lys Pro Gly Asp Leu Glu
1               5                   10                  15

Ser Ala Pro Val Leu Arg Thr
            20

<210> SEQ ID NO 149
<211> LENGTH: 21
<212> TYPE: PRT
<213> ORGANISM: Homo sapiens

<400> SEQUENCE: 149

Arg Ser Leu Leu Glu Phe Asn Thr Thr Val Ser Cys Asp Gln Gln Gly
1               5                   10                  15

Thr Asn His Arg Val
            20

<210> SEQ ID NO 150
<211> LENGTH: 21
<212> TYPE: PRT
<213> ORGANISM: Homo sapiens

<400> SEQUENCE: 150

Lys Thr Asn Ile Thr Leu Val Cys Lys Pro Gly Asp Leu Glu Ser Ala
1               5                   10                  15

Pro Val Leu Arg Thr
            20

<210> SEQ ID NO 151
<211> LENGTH: 14
<212> TYPE: PRT
<213> ORGANISM: Homo sapiens

<400> SEQUENCE: 151

Lys Leu Val Leu Pro Ala Lys Asn Thr Thr Asn Leu Lys Thr
1               5                   10

<210> SEQ ID NO 152
<211> LENGTH: 24
<212> TYPE: PRT
<213> ORGANISM: Homo sapiens

<400> SEQUENCE: 152

Arg Ser His Gly Val Gln Thr Met Val Val Leu Asn Asn Leu Glu Pro
1               5                   10                  15

Asn Thr Thr Tyr Glu Ile Arg Val
            20

<210> SEQ ID NO 153
<211> LENGTH: 13
<212> TYPE: PRT
<213> ORGANISM: Homo sapiens

<400> SEQUENCE: 153

Arg Ser Cys Ile Asn Glu Ser Ala Ile Asp Ser Arg Gly
1               5                   10

<210> SEQ ID NO 154
<211> LENGTH: 20
<212> TYPE: PRT
<213> ORGANISM: Homo sapiens

<400> SEQUENCE: 154
```

Lys Val Met Glu Leu Glu Lys Glu Ile Ala Asn Ala Thr Ala Lys Pro
1               5                   10                  15

Glu Asp Arg Asn
            20

<210> SEQ ID NO 155
<211> LENGTH: 22
<212> TYPE: PRT
<213> ORGANISM: Homo sapiens

<400> SEQUENCE: 155

Arg Thr Ser Leu Glu Leu Trp Met His Thr Asp Pro Val Ser Gln Lys
1               5                   10                  15

Asn Glu Ser Val Arg Asn
            20

<210> SEQ ID NO 156
<211> LENGTH: 17
<212> TYPE: PRT
<213> ORGANISM: Homo sapiens

<400> SEQUENCE: 156

Arg Ala Glu Pro Pro Leu Asn Ala Ser Ala Ser Asp Gln Gly Glu Lys
1               5                   10                  15

Val

<210> SEQ ID NO 157
<211> LENGTH: 39
<212> TYPE: PRT
<213> ORGANISM: Homo sapiens

<400> SEQUENCE: 157

Lys Leu Gly Asn Thr Ile Ser Ser Leu Phe Gly Gly Gly Thr Thr Pro
1               5                   10                  15

Asp Ala Lys Glu Asn Gly Thr Asp Thr Val Gln Glu Glu Glu Glu Ser
            20                  25                  30

Pro Ala Glu Gly Ser Lys Asp
            35

<210> SEQ ID NO 158
<211> LENGTH: 18
<212> TYPE: PRT
<213> ORGANISM: Homo sapiens

<400> SEQUENCE: 158

Arg Leu Ser Ala Leu Asp Asn Leu Leu Asn His Ser Ser Met Phe Leu
1               5                   10                  15

Lys Gly

<210> SEQ ID NO 159
<211> LENGTH: 29
<212> TYPE: PRT
<213> ORGANISM: Homo sapiens

<400> SEQUENCE: 159

Arg Gln Thr Val His Phe Gln Ile Ser Ser Gln Leu Gln Phe Ser Pro
1               5                   10                  15

Glu Glu Val Leu Gly Met Val Leu Asn Tyr Ser Arg Ser
            20                  25

```
<210> SEQ ID NO 160
<211> LENGTH: 13
<212> TYPE: PRT
<213> ORGANISM: Homo sapiens

<400> SEQUENCE: 160

Arg Val Phe Gly Ser Gln Asn Leu Thr Thr Val Lys Leu
 1               5                  10

<210> SEQ ID NO 161
<211> LENGTH: 11
<212> TYPE: PRT
<213> ORGANISM: Homo sapiens

<400> SEQUENCE: 161

Lys Val Ile Asn Glu Thr Trp Ala Trp Lys Asn
 1               5                  10

<210> SEQ ID NO 162
<211> LENGTH: 20
<212> TYPE: PRT
<213> ORGANISM: Homo sapiens

<400> SEQUENCE: 162

Lys Val Ile Asn Glu Thr Trp Ala Trp Lys Asn Ala Thr Leu Ala Glu
 1               5                  10                  15

Gln Ala Lys Leu
             20

<210> SEQ ID NO 163
<211> LENGTH: 25
<212> TYPE: PRT
<213> ORGANISM: Homo sapiens

<400> SEQUENCE: 163

Arg Leu Pro Gln Val Ser Pro Ala Asp Ser Gly Glu Tyr Val Cys Arg
 1               5                  10                  15

Val Glu Asn Gly Ser Gly Pro Lys Glu
             20                  25

<210> SEQ ID NO 164
<211> LENGTH: 21
<212> TYPE: PRT
<213> ORGANISM: Homo sapiens

<400> SEQUENCE: 164

Lys Phe Leu Asn Asp Ser Ile Val Asp Pro Val Asp Ser Glu Trp Phe
 1               5                  10                  15

Gly Phe Tyr Arg Ser
             20

<210> SEQ ID NO 165
<211> LENGTH: 23
<212> TYPE: PRT
<213> ORGANISM: Homo sapiens

<400> SEQUENCE: 165

Arg Met His Ile Phe Gln Asn Gly Ser Leu Val Ile His Asp Val Ala
 1               5                  10                  15

Pro Glu Asp Ser Gly Arg Tyr
             20

<210> SEQ ID NO 166
```

<211> LENGTH: 27
<212> TYPE: PRT
<213> ORGANISM: Homo sapiens

<400> SEQUENCE: 166

Lys Asp Val Val Thr Ala Ala Gly Asp Met Leu Lys Asp Asn Ala Thr
1               5                   10                  15

Glu Glu Glu Ile Leu Val Tyr Leu Glu Lys Thr
            20                  25

<210> SEQ ID NO 167
<211> LENGTH: 19
<212> TYPE: PRT
<213> ORGANISM: Homo sapiens

<400> SEQUENCE: 167

Arg Asn Leu Glu Lys Asn Ser Thr Lys Gln Glu Ile Leu Ala Ala Leu
1               5                   10                  15

Glu Lys Gly

<210> SEQ ID NO 168
<211> LENGTH: 23
<212> TYPE: PRT
<213> ORGANISM: Homo sapiens

<400> SEQUENCE: 168

Lys Gly Gln Thr Ala Leu Gly Phe Leu Tyr Ala Ser Gly Leu Gly Val
1               5                   10                  15

Asn Ser Ser Gln Ala Lys Ala
            20

<210> SEQ ID NO 169
<211> LENGTH: 26
<212> TYPE: PRT
<213> ORGANISM: Homo sapiens

<400> SEQUENCE: 169

Arg Asp Ala Gly Val Leu Asn Asp Thr Leu Val Ile Phe Thr Ser Asp
1               5                   10                  15

Asn Gly Ile Pro Phe Pro Ser Gly Arg Thr
            20                  25

<210> SEQ ID NO 170
<211> LENGTH: 34
<212> TYPE: PRT
<213> ORGANISM: Homo sapiens

<400> SEQUENCE: 170

Arg Asn Ala Leu Leu Leu Leu Ala Asp Asp Gly Gly Phe Glu Ser Gly
1               5                   10                  15

Ala Tyr Asn Asn Ser Ala Ile Ala Thr Pro His Leu Asp Ala Leu Ala
            20                  25                  30

Arg Arg

<210> SEQ ID NO 171
<211> LENGTH: 27
<212> TYPE: PRT
<213> ORGANISM: Homo sapiens

<400> SEQUENCE: 171

Arg Tyr Pro Gln Asp Tyr Gln Phe Tyr Ile Gln Asn Phe Thr Ala Leu
1               5                   10                  15

Pro Leu Asn Thr Val Val Pro Pro Gln Arg Gln
            20                  25

<210> SEQ ID NO 172
<211> LENGTH: 40
<212> TYPE: PRT
<213> ORGANISM: Homo sapiens

<400> SEQUENCE: 172

Lys Ala Gly Tyr Phe Asn Phe Thr Ser Ala Thr Ile Thr Tyr Leu Ala
 1               5                  10                  15
Gln Glu Asp Gly Pro Val Val Ile Gly Ser Thr Ser Ala Pro Gly Gln
            20                  25                  30
Gly Gly Ile Leu Ala Gln Arg Glu
        35                  40

<210> SEQ ID NO 173
<211> LENGTH: 40
<212> TYPE: PRT
<213> ORGANISM: Homo sapiens

<400> SEQUENCE: 173

Arg Ile Ala Pro Ala Ser Asn Val Ser His Thr Val Val Leu Arg Pro
 1               5                  10                  15
Leu Lys Ala Lys Phe Leu Ser Ser Ser Pro His Leu Pro Pro Ser Ser
            20                  25                  30
Tyr Phe Asn Ala Ser Gly Arg Ala
        35                  40

<210> SEQ ID NO 174
<211> LENGTH: 16
<212> TYPE: PRT
<213> ORGANISM: Homo sapiens

<400> SEQUENCE: 174

Arg Leu Ala Val Thr Asn Thr Thr Met Thr Gly Thr Val Leu Lys Met
 1               5                  10                  15

<210> SEQ ID NO 175
<211> LENGTH: 19
<212> TYPE: PRT
<213> ORGANISM: Homo sapiens

<400> SEQUENCE: 175

Lys Phe Asn Leu Thr Glu Thr Ser Glu Ala Glu Ile His Gln Ser Phe
 1               5                  10                  15
Gln His Leu

<210> SEQ ID NO 176
<211> LENGTH: 17
<212> TYPE: PRT
<213> ORGANISM: Homo sapiens

<400> SEQUENCE: 176

Phe Leu Ser Leu Gly Ala His Asn Thr Thr Leu Thr Glu Ile Leu Lys
 1               5                  10                  15
Gly

<210> SEQ ID NO 177
<211> LENGTH: 25
<212> TYPE: PRT

<213> ORGANISM: Homo sapiens

<400> SEQUENCE: 177

Leu Ser Ile Ser Thr Ala Leu Ala Phe Leu Ser Leu Gly Ala His Asn
1               5                   10                  15
Thr Thr Leu Thr Glu Ile Leu Lys Gly
            20                  25

<210> SEQ ID NO 178
<211> LENGTH: 15
<212> TYPE: PRT
<213> ORGANISM: Homo sapiens

<400> SEQUENCE: 178

Arg Gln Leu Ala His Gln Ser Asn Ser Thr Asn Ile Phe Phe Ser
1               5                   10                  15

<210> SEQ ID NO 179
<211> LENGTH: 24
<212> TYPE: PRT
<213> ORGANISM: Homo sapiens

<400> SEQUENCE: 179

Lys Ala Ala Leu Ala Ala Phe Asn Ala Gln Asn Asn Gly Ser Asn Phe
1               5                   10                  15
Gln Leu Glu Glu Ile Ser Arg Ala
            20

<210> SEQ ID NO 180
<211> LENGTH: 17
<212> TYPE: PRT
<213> ORGANISM: Homo sapiens

<400> SEQUENCE: 180

Phe Asn Leu Thr Glu Thr Ser Glu Ala Glu Ile His Gln Ser Phe Gln
1               5                   10                  15
His

<210> SEQ ID NO 181
<211> LENGTH: 23
<212> TYPE: PRT
<213> ORGANISM: Homo sapiens

<400> SEQUENCE: 181

Arg Gly Phe Gly Val Ala Ile Val Gly Asn Tyr Thr Ala Ala Leu Pro
1               5                   10                  15
Thr Glu Ala Ala Leu Arg Thr
            20

<210> SEQ ID NO 182
<211> LENGTH: 18
<212> TYPE: PRT
<213> ORGANISM: Homo sapiens

<400> SEQUENCE: 182

Tyr Val Leu Asp Tyr Leu Asn Glu Thr Gln Gln Leu Thr Pro Glu Ile
1               5                   10                  15
Lys Ser

<210> SEQ ID NO 183
<211> LENGTH: 19
<212> TYPE: PRT

<213> ORGANISM: Homo sapiens

<400> SEQUENCE: 183

Asn Leu Val Pro Val Pro Ile Thr Asn Ala Thr Leu Asp Gln Ile Thr
1               5                   10                  15
Gly Lys Trp

<210> SEQ ID NO 184
<211> LENGTH: 18
<212> TYPE: PRT
<213> ORGANISM: Homo sapiens

<400> SEQUENCE: 184

Lys Tyr Leu Gly Asn Ala Thr Ala Ile Phe Phe Leu Pro Asp Glu Gly
1               5                   10                  15
Lys Leu

<210> SEQ ID NO 185
<211> LENGTH: 15
<212> TYPE: PRT
<213> ORGANISM: Homo sapiens

<400> SEQUENCE: 185

Arg Gln Leu Ala His Gln Ser Asn Ser Thr Asn Ile Phe Phe Ser
1               5                   10                  15

<210> SEQ ID NO 186
<211> LENGTH: 18
<212> TYPE: PRT
<213> ORGANISM: Homo sapiens

<400> SEQUENCE: 186

Lys Tyr Thr Gly Asn Ala Ser Ala Leu Phe Ile Leu Pro Asp Gln Asp
1               5                   10                  15
Lys Met

<210> SEQ ID NO 187
<211> LENGTH: 15
<212> TYPE: PRT
<213> ORGANISM: Homo sapiens

<400> SEQUENCE: 187

Asn His Met Gly Asn Val Thr Phe Thr Ile Pro Ala Asn Arg Glu
1               5                   10                  15

<210> SEQ ID NO 188
<211> LENGTH: 18
<212> TYPE: PRT
<213> ORGANISM: Homo sapiens

<400> SEQUENCE: 188

Arg Phe Ser Asp Gly Leu Glu Ser Asn Ser Ser Thr Gln Phe Glu Val
1               5                   10                  15
Lys Lys

<210> SEQ ID NO 189
<211> LENGTH: 18
<212> TYPE: PRT
<213> ORGANISM: Homo sapiens

<400> SEQUENCE: 189

Lys Val Val Leu His Pro Asn Tyr Ser Gln Val Asp Ile Gly Leu Ile

```
                1               5                  10                 15
Lys Leu

<210> SEQ ID NO 190
<211> LENGTH: 15
<212> TYPE: PRT
<213> ORGANISM: Homo sapiens

<400> SEQUENCE: 190

Lys Asn Leu Phe Leu Asn His Ser Glu Asn Ala Thr Ala Lys Asp
 1               5                  10                 15

<210> SEQ ID NO 191
<211> LENGTH: 21
<212> TYPE: PRT
<213> ORGANISM: Homo sapiens

<400> SEQUENCE: 191

Arg Val Leu Ser Asn Asn Ser Asp Ala Asn Leu Glu Leu Ile Asn Thr
 1               5                  10                 15

Trp Val Ala Lys Asn
            20

<210> SEQ ID NO 192
<211> LENGTH: 14
<212> TYPE: PRT
<213> ORGANISM: Homo sapiens

<400> SEQUENCE: 192

His Phe Phe Ala Pro Gln Asn Leu Thr Asn Met Asn Lys Asn
 1               5                  10

<210> SEQ ID NO 193
<211> LENGTH: 16
<212> TYPE: PRT
<213> ORGANISM: Homo sapiens

<400> SEQUENCE: 193

Lys Gly Ala Phe Ile Ser Asn Phe Ser Met Thr Val Asp Gly Lys Thr
 1               5                  10                 15

<210> SEQ ID NO 194
<211> LENGTH: 14
<212> TYPE: PRT
<213> ORGANISM: Homo sapiens

<400> SEQUENCE: 194

Asn Gln Leu Val Asp Ala Leu Thr Thr Trp Gln Asn Lys Thr
 1               5                  10

<210> SEQ ID NO 195
<211> LENGTH: 14
<212> TYPE: PRT
<213> ORGANISM: Homo sapiens

<400> SEQUENCE: 195

Lys Phe Leu Asn Asp Thr Met Ala Val Tyr Glu Ala Lys Leu
 1               5                  10

<210> SEQ ID NO 196
<211> LENGTH: 15
<212> TYPE: PRT
<213> ORGANISM: Homo sapiens
```

```
<400> SEQUENCE: 196

Arg Ile Tyr Ser Gly Ile Leu Asn Leu Ser Asp Ile Thr Lys Asp
 1               5                  10                  15

<210> SEQ ID NO 197
<211> LENGTH: 14
<212> TYPE: PRT
<213> ORGANISM: Homo sapiens

<400> SEQUENCE: 197

Lys Leu Asn Ala Glu Asn Asn Ala Thr Phe Tyr Phe Lys Ile
 1               5                  10

<210> SEQ ID NO 198
<211> LENGTH: 25
<212> TYPE: PRT
<213> ORGANISM: Artificial Sequence
<220> FEATURE:
<223> OTHER INFORMATION: synthetic peptide standards

<400> SEQUENCE: 198

Gly Val Thr Ser Val Ser Gln Ile Phe His Ser Pro Asp Leu Ala Ile
 1               5                  10                  15

Arg Asp Thr Phe Val Asp Ala Ser Arg
            20                  25

<210> SEQ ID NO 199
<211> LENGTH: 21
<212> TYPE: PRT
<213> ORGANISM: Artificial Sequence
<220> FEATURE:
<223> OTHER INFORMATION: synthetic peptide standards

<400> SEQUENCE: 199

Val Tyr Ile His Pro Phe His Leu Val Ile His Asp Glu Ser Thr Cys
 1               5                  10                  15

Glu Gln Leu Ala Lys
            20

<210> SEQ ID NO 200
<211> LENGTH: 22
<212> TYPE: PRT
<213> ORGANISM: Artificial Sequence
<220> FEATURE:
<223> OTHER INFORMATION: synthetic peptide standards

<400> SEQUENCE: 200

Val Thr Gln Asp Leu Thr Leu Ile Glu Glu Ser Leu Thr Ser Glu Phe
 1               5                  10                  15

Ile His Asp Ile Asp Arg
            20

<210> SEQ ID NO 201
<211> LENGTH: 25
<212> TYPE: PRT
<213> ORGANISM: Artificial Sequence
<220> FEATURE:
<223> OTHER INFORMATION: synthetic peptide standards

<400> SEQUENCE: 201

Ser Arg Val Tyr Leu Gln Gly Leu Ile Asp Tyr Tyr Leu Phe Gly Asp
 1               5                  10                  15

Ser Ser Thr Val Leu Glu Asp Ser Lys
            20                  25
```

```
<210> SEQ ID NO 202
<211> LENGTH: 18
<212> TYPE: PRT
<213> ORGANISM: Artificial Sequence
<220> FEATURE:
<223> OTHER INFORMATION: synthetic peptide standards

<400> SEQUENCE: 202

Ala Val Asp Ile Thr Ser Glu Asn Leu Ile Asp Val Val Ser Leu
  1               5                  10                  15
Ile Arg

<210> SEQ ID NO 203
<211> LENGTH: 18
<212> TYPE: PRT
<213> ORGANISM: Artificial Sequence
<220> FEATURE:
<223> OTHER INFORMATION: synthetic peptide standards

<400> SEQUENCE: 203

Tyr Gln Phe Asn Thr Asn Val Val Phe Ser Asn Asp Gly Thr Leu Val
  1               5                  10                  15
Asp Arg

<210> SEQ ID NO 204
<211> LENGTH: 21
<212> TYPE: PRT
<213> ORGANISM: Artificial Sequence
<220> FEATURE:
<223> OTHER INFORMATION: synthetic peptide standards

<400> SEQUENCE: 204

His Gly Val Ile Ile Ser Ser Thr Val Asp Thr Tyr Glu Asp Gly Ser
  1               5                  10                  15
Ser Val Glu Tyr Arg
         20

<210> SEQ ID NO 205
<211> LENGTH: 15
<212> TYPE: PRT
<213> ORGANISM: Artificial Sequence
<220> FEATURE:
<223> OTHER INFORMATION: synthetic peptide standards

<400> SEQUENCE: 205

Gln Asn Gln Cys Phe Tyr Asp Ser Ser Tyr Leu Asn Val Gln Arg
  1               5                  10                  15

<210> SEQ ID NO 206
<211> LENGTH: 21
<212> TYPE: PRT
<213> ORGANISM: Artificial Sequence
<220> FEATURE:
<223> OTHER INFORMATION: synthetic peptide standards

<400> SEQUENCE: 206

Val Val Gly Val Pro Tyr Gln Gly Asp Ala Thr Ala Leu Phe Ile Leu
  1               5                  10                  15
Pro Ser Glu Gly Lys
         20

<210> SEQ ID NO 207
<211> LENGTH: 22
```

```
<212> TYPE: PRT
<213> ORGANISM: Artificial Sequence
<220> FEATURE:
<223> OTHER INFORMATION: synthetic peptide standards

<400> SEQUENCE: 207

Gly Pro Ser Thr Pro Leu Pro Glu Asp Pro Asn Trp Asp Val Thr Glu
1               5                   10                  15

Phe His Thr Thr Pro Lys
            20

<210> SEQ ID NO 208
<211> LENGTH: 19
<212> TYPE: PRT
<213> ORGANISM: Artificial Sequence
<220> FEATURE:
<223> OTHER INFORMATION: synthetic peptide standards

<400> SEQUENCE: 208

Ser Leu Thr Phe Asp Glu Thr Tyr Gln Asp Ile Ser Glu Leu Val Tyr
1               5                   10                  15

Gly Ala Lys

<210> SEQ ID NO 209
<211> LENGTH: 20
<212> TYPE: PRT
<213> ORGANISM: Artificial Sequence
<220> FEATURE:
<223> OTHER INFORMATION: synthetic peptide standards

<400> SEQUENCE: 209

Thr Asp Asn Ser Leu Leu Asp Gln Ala Leu Gln Asp Asp Thr Val Phe
1               5                   10                  15

Leu Asn Met Arg
            20

<210> SEQ ID NO 210
<211> LENGTH: 13
<212> TYPE: PRT
<213> ORGANISM: Homo sapiens

<400> SEQUENCE: 210

Ile Tyr Ser Gly Ile Leu Asn Leu Ser Asp Ile Thr Lys
1               5                   10
```